United States Patent
Hsu et al.

(10) Patent No.: US 6,268,531 B1
(45) Date of Patent: Jul. 31, 2001

(54) CONTINUOUS HYDROLYSIS PROCESS FOR PREPARING 2-HYDROXY-4-METHYLTHIOBUTANOIC ACID OR SALTS THEREOF

(75) Inventors: Yung C. Hsu; Thomas F. Blackburn, both of Chesterfield; Paul F. Pellegrin, St. Louis; Allen H. Kranz, St. Charles; James M. Willock, Ballwin, all of MO (US)

(73) Assignee: Novus International, Inc., St. Louis, MO (US)

( * ) Notice: Subject to any disclaimer, the term of this patent is extended or adjusted under 35 U.S.C. 154(b) by 0 days.

(21) Appl. No.: 09/165,819

(22) Filed: Oct. 2, 1998

Related U.S. Application Data

(60) Division of application No. 08/647,161, filed on May 21, 1996, now Pat. No. 5,856,567, which is a continuation-in-part of application No. 08/477,768, filed on Jun. 7, 1995, now abandoned.

(51) Int. Cl.[7] ............................. C07C 51/42; C07C 51/08
(52) U.S. Cl. ............................. 562/580; 562/581
(58) Field of Search ..................... 562/581, 580

(56) References Cited

U.S. PATENT DOCUMENTS

| 2,432,429 | 12/1947 | Lecky | 260/534 |
|---|---|---|---|
| 2,432,478 | 12/1947 | Lecky | 260/534 |

(List continued on next page.)

FOREIGN PATENT DOCUMENTS

| 4236058 | 4/1994 | (DE) . | |
|---|---|---|---|
| 0 143 100 | 11/1984 | (EP) | C07C/149/20 |
| 915193 | 9/1960 | (GB) . | |
| 57-82339 | 5/1982 | (JP) | C07C/57/04 |
| 72031 | 3/1981 | (RO) . | |
| 104950 | 8/1992 | (RO) | C08F/20/56 |
| 96/01809 | 6/1995 | (WO) | C07C/319/28 |
| 96/01808 | 7/1995 | (WO) | C07C/319/20 |
| 96/05173 | 8/1995 | (WO) | C07C/319/28 |

OTHER PUBLICATIONS

Denbigh, "Chemical Reactor Theory," 1965, pp. 38–124.
Trambouze et al., A.I.Ch.E. Journal, "Continuous Stirred Tank Reactors," Sep. 1959, vol. 5, pp. 384–390.
A. Cholette & J. Blanchet, "Optimum . . . Conditions," The Can. J. of Chem. Eng., pp. 192–198, Oct. 1961.
Cholette et al., "Performance of Flow Reactors . . . Mixing," The Can. J. of Chem. Eng., pp. 1–18, Feb. 1960.

*Primary Examiner*—Rosalynd Keys
(74) *Attorney, Agent, or Firm*—Senniger, Powers, Leavitt & Roedel

(57) ABSTRACT

A continuous process for the preparation of 2-hydroxy-4-methylthiobutanoic acid or a salt thereof which includes introducing an aqueous mineral acid into a nitrile hydrolysis reactor including a continuous stirred tank reactor and introducing 2-hydroxy-4-methylthiobutanenitrile into the nitrile hydrolysis reactor. 2-hydroxy-4-methylthiobutanenitrile is continually hydrolyzed within the nitrile hydrolysis reactor to produce a nitrile hydrolysis reactor product stream containing 2-hydroxy-4-methylthiobutanamide. The nitrile hydrolysis reactor product stream is continuously introduced into an amide hydrolysis flow reactor. 2-hydroxy-4-methylthiobutanamide is continually hydrolyzed within the amide hydrolysis flow reactor to produce an aqueous hydrolyzate product containing 2-hydroxy-4-methylthiobutanoic acid. 2-hydroxy-4-methylthiobutanoic acid is recovered from the aqueous hydrolyzate product.

105 Claims, 9 Drawing Sheets

U.S. PATENT DOCUMENTS

| | | | |
|---|---|---|---|
| 2,443,391 | 6/1948 | Kirkpatrick | 260/534 |
| 2,485,236 | 10/1949 | Gresham et al. | 465/5 |
| 2,542,768 | 2/1951 | Gresham et al. | 260/465.6 |
| 2,557,920 | 6/1951 | White | 260/319 |
| 2,564,105 | 8/1951 | Gresham et al. | 260/465.5 |
| 2,642,459 | 6/1953 | White | 260/534 |
| 2,676,190 | 4/1954 | Bernard et al. | 260/601 |
| 2,688,038 | 8/1954 | Merner | 260/534 |
| 2,745,745 | 5/1956 | Blake et al. | 99/4 |
| 2,938,053 | 5/1960 | Blake et al. | 260/561 |
| 2,946,818 | 7/1960 | Anagnostopoulos | 260/535 |
| 3,272,860 | 9/1966 | Nufer | 260/525 |
| 3,773,927 | 11/1973 | Cummins | 424/166 |
| 3,968,152 | 7/1976 | Sze et al. | 260/515 P |
| 4,064,159 | 12/1977 | Labat et al. | 260/465.5 |
| 4,233,235 | 11/1980 | Camden et al. | 260/502 R |
| 4,310,690 | 1/1982 | Cummins | 562/581 |
| 4,311,803 | 1/1982 | Smith et al. | 525/53 |
| 4,335,257 | 6/1982 | Cummins et al. | 562/581 |
| 4,524,077 | 6/1985 | Ruest et al. | 514/557 |
| 4,579,962 | 4/1986 | Takano | 556/131 |
| 4,677,224 | 6/1987 | Commeyras et al. | 562/557 |
| 4,855,495 | 8/1989 | Takano | 562/581 |
| 4,912,257 | 3/1990 | Hernandez et al. | 562/581 |
| 5,068,383 | 11/1991 | Bourgoin et al. | 556/452 |
| 5,244,590 | 9/1993 | Chung et al. | 252/43 |
| 5,250,611 | 10/1993 | Baumgartner et al. | 525/52 |
| 5,420,304 | 5/1995 | Verser et al. | 549/274 |
| 5,583,243 | 12/1996 | Abdel-Monem | 556/49 |

US 6,268,531 B1

CONTINUOUS HYDROLYSIS PROCESS FOR PREPARING 2-HYDROXY-4-METHYLTHIOBUTANOIC ACID OR SALTS THEREOF

REFERENCE TO RELATED APPLICATIONS

This application is a divisional of application Ser. No. 08/647,161, filed May 21, 1996 which issued as U.S. Pat. No. 5,856,567 as a continuaution-in-part of Ser. No. 08/477,768, filed Jun. 7, 1995 now abandoned.

BACKGROUND OF THE INVENTION

This invention relates to the preparation of 2-hydroxy-4-methylthiobutanoic acid or salts thereof and more particularly to an improved process for preparing an aqueous product comprising 2-hydroxy-4-methylthiobutanoic acid.

2-hydroxy-4-methylthiobutanoic acid, commonly referred to as the hydroxy analog of methionine and also known as 2-hydroxy-4-methylthiobutyric acid or HMBA, is an analog of the essential amino acid methionine. Methionine analogs such as HMBA are effective in supplying methionine for nutritional uses, particularly as a poultry feed supplement. To efficiently produce feed supplements containing HMBA, the hydrolysis must be sufficiently complete.

HMBA has been manufactured by various processes involving hydrolysis of 2-hydroxy-4-methylthiobutanenitrile (also known as HMBN or 2-hydroxy-4-methylthiobutyronitrile and hereinafter "HMBN" or "nitrile"). HMBA has been produced as a racemic D,L-mixture by hydrolyzing HMBN with a mineral acid, precipitating the acid residue by addition of an alkaline earth hydroxide or carbonate, and recovering a salt of HMBA from the aqueous phase by evaporative crystallization, as described, for example, in Blake et al U.S. Pat. No. 2,745,745.

British Patent No. 915,193 describes a process for the preparation of the calcium salt of HMBA in which HMBN is hydrolyzed to HMBA in a continuous back-mixed reactor using a dilute sulfuric acid solution, and HMBA is separated from the reaction liquor by extraction with an ether. Because of the use of a continuous back-mixed reaction system, the process of the British patent may not achieve complete conversion of HMBN or amide intermediate to HMBA. The presence of significant unreacted material is undesirable where a liquid HMBA product is to be made.

Recently, HEBA has been commercially produced by hydrolyzing HMBN with sulfuric acid to form a high quality hydrolyzate containing HMBA, extracting HMBA from the hydrolyzate, and recovering the HMBA from the extract as described by Ruest et al. U.S. Pat. No. 4,524,077. In the process, HMBN is mixed with sulfuric acid having a strength of between about 50% and about 70% by weight on an organic-free basis at a temperature of between about 25° C. and about 65° C. To control the rate of reaction, the HMBN is preferably added to the acid over a period of about 30 to about 60 minutes. Under the preferred conditions, substantial conversion of the nitrile to 2-hydroxy-4-methylthiobutanamide (also known as 2-hydroxy-4-methylthiobutyramide and hereinafter "amide") takes place in a period of between about one-half hour and about one and one-half hours. Thereafter, the amide is converted to HMBA by further hydrolysis at a temperature within the range of between about 70° C. and 120° C. Final hydrolysis of the amide to the acid is carried out in sulfuric acid having an initial strength of between about 30% and about 50% by weight on a organic-free basis. To provide the preferred acid strength, the acid phase is diluted by adding water before heating the reaction mixture. Under conditions of relatively dilute acid strength and increased temperature, the amide is converted to the acid within a period of approximately one and one-half to three hours. In carrying out the hydrolysis, approximately one mole of sulfuric acid per mole of the HMBN feed is used, with an acid excess of 0 to 10%, preferably 0 to 5%, providing satisfactory results. Ruest et al. describe a batch process and state that a batch process is preferred to ensure that the hydrolysis reaction is carried substantially to completion. If a continuous reaction system is utilized, Ruest et al. describe that it should be designed and operated to assure essentially complete conversion. For example, continuous operation could be implemented in a plug flow tubular reactor or cascaded stirred tank system. A single back-mixed reactor is described by Ruest et al. as providing adequate conversion only at residence times that would generally be considered unacceptable for commercial production.

Hernandez et al. U.S. Pat. No. 4,912,257 describes a process in which HMBA is produced by sulfuric acid hydrolysis of HMBN in a single step. HMBN is fed to an acidification vessel where it is mixed with 98% sulfuric acid at an acid/nitrile molar ratio between 0.5 and 2 to form a reaction mixture containing 20–50% by weight sulfuric acid. The mixture is agitated and cooled to 50° C. in a continuous addition loop for 30–60 minutes as the reaction mixture is produced batchwise. The reaction mixture is then fed to a hydrolysis reactor and heated to a temperature of between 60° C. and 140° C. for five minutes to six hours while applying a slight vacuum to the reactor. The process described by Hernandez et al. is said to produce HMBA by hydrolysis of the acidified HMBN solution in a single step unlike the two step hydrolysis processes known in the art.

In order to provide a high quality hydrolyzate product containing maximum HMBA and minimal nitrile and amide components, high conversion of HMBN and 2-hydroxy-4-methylthiobutyramide to HMBA must be obtained. Batch production of HMBA generally provides high conversion. However, conventional batch processes for producing HMBA have several drawbacks. The productivity of a batch process is limited by batch turnaround time. Additionally, the quality of HMBA hydrolyzate can deviate between batches because reaction conditions can vary as each batch is produced. Filling and emptying of the batch reactor and non-steady state conditions cause vapor emissions that must be treated before release. The equipment required for the prior art processes is costly. Sulfuric acid and water are mixed in an acid dilution tank to form diluted sulfuric acid feed. A heat exchanger is required to remove the heat of dilution that is generated within the tank. The tank, heat exchanger, pump and recirculation loop must be of corrosion resistant construction.

SUMMARY OF THE INVENTION

Among the several objects of the present invention are the provision of an improved process for the preparation of HMBA; the provision of such a process that can be operated in a continuous mode; the provision of such a process that can be operated with high productivity; the provision of such a process that can significantly reduce capital and maintenance costs as compared to conventional processes; the provision of such a process that affords improved control of reaction conditions as compared to conventional batch hydrolysis systems; the provision of such a process that reduces the vapor emissions as compared to conventional batch systems; the provision of such a process that eliminates the need for separate sulfuric acid dilution, in particular, the provision of such a process that can be operated using a concentrated sulfuric acid feed stream without prior dilution; the provision of such a process that effects essentially complete conversion of HMBN to HMBA; and the provision of such a process that can produce HMBA of consistent quality for use in the preparation of animal feed supplements.

These and other objects are obtained through a process for the preparation of HMBA or a salt thereof including introducing a mineral acid into a nitrile hydrolysis reactor comprising a continuous stirred tank reactor, and introducing 2-hydroxy-4-methylthiobutanenitrile into the nitrile hydrolysis reactor. 2-hydroxy-4-methylthiobutanenitrile is continually hydrolyzed within the nitrile hydrolysis reactor to produce a nitrile hydrolysis reactor product stream containing 2-hydroxy-4-methylthiobutanamide. The nitrile hydrolysis reactor product stream is continuously introduced into an amide hydrolysis flow reactor. 2-hydroxy-4-methylthiobutanamide is continuously hydrolyzed within the amide hydrolysis flow reactor to produce a finished aqueous hydrolyzate product containing 2-hydroxy-4-methylthiobutanoic acid. 2-hydroxy-4-methylthiobutanoic acid is recovered from the finished aqueous hydrolyzate product.

In another embodiment of the invention, 2-hydroxy-4-methylthiobutanoic acid or a salt thereof is produced by a process in which 2-hydroxy-4-methylthiobutanenitrile, concentrated sulfuric acid having a strength of between about 70% by weight and about 99% by weight, and water are concurrently introduced into a vessel in which 2-hydroxy-4-methylthiobutanenitrile is hydrolyzed. 2-hydroxy-4-methylthiobutanenitrile is hydrolyzed within the vessel to produce an aqueous hydrolysis mixture containing 2-hydroxy-4-methylthiobutanamide. 2-hydroxy-4-methylthiobutanamide is hydrolyzed to produce a finished aqueous hydrolyzate product containing 2-hydroxy-4-methylthiobutanoic acid. 2-hydroxy-4-methylthiobutanoic acid is recovered from the finished aqueous hydrolyzate product.

Yet another embodiment of the present invention is directed to an apparatus for use in a process for the preparation of HMBA. The apparatus includes a first continuous stirred tank reactor for the continuous hydrolysis of 2-hydroxy-4-methylthiobutanenitrile in the presence of a mineral acid to produce an aqueous hydrolysis mixture containing 2-hydroxy-4-methylthiobutanamide. The apparatus also includes an amide hydrolysis flow reactor for the continuous hydrolysis of 2-hydroxy-4-methylthiobutanamide with sulfuric acid to produce a finished aqueous hydrolyzate product containing 2-hydroxy-4-methylthiobutanoic acid.

Another embodiment of the invention is directed to a process for the preparation of 2-hydroxy-4-methylthiobutanoic acid or a salt thereof that includes introducing 2-hydroxy-4-methylthiobutanenitrile and an aqueous mineral acid into an aqueous hydrolysis mixture comprising 2-hydroxy-4-methylthiobutanamide, mineral acid, and unreacted 2-hydroxy-4-methylthiobutanenitrile. The 2-hydroxy-4-methylthiobutanenitrile in the aqueous hydrolysis mixture is hydrolyzed in a continuous nitrile hydrolysis reactor comprising a back-mixed reaction zone and a circulation zone in fluid flow communication with the back-mixed reaction zone. The circulation zone comprises a circulating line. The aqueous hydrolysis mixture is continuously circulated in a circulating stream that is withdrawn from the back-mixed reaction zone, passed through the circulation zone and returned to the back-mixed reaction zone. The circulating stream as withdrawn from the back-mixed reaction zone contains unreacted 2-hydroxy-4-methylthiobutanenitrile. A portion of the aqueous hydrolysis mixture is removed from a forward flow port in the circulation zone to form a nitrile hydrolysis reactor product stream. The nitrile hydrolysis reactor product stream is transferred to an amide hydrolysis flow reactor. The nitrile hydrolysis reactor product stream is diluted with water at a point downstream of the forward flow port to provide a finishing reaction stream. The 2-hydroxy-4-methylthiobutanamide contained in the finishing reaction stream is hydrolyzed in the amide hydrolysis flow reactor to produce a finished aqueous hydrolyzate product containing 2-hydroxy-4-methylthiobutanoic acid. The sum of the residence time of the circulating stream in the circulation zone upstream of the forward flow port and the residence time of the nitrile hydrolysis reactor product stream downstream of the forward flow port prior to dilution is sufficient to substantially extinguish residual 2-hydroxy-4-methylthiobutanenitrile prior to the dilution of the nitrile hydrolysis reactor product stream.

DETAILED DESCRIPTION OF THE PREFERRED EMBODIMENT

Figure 1:
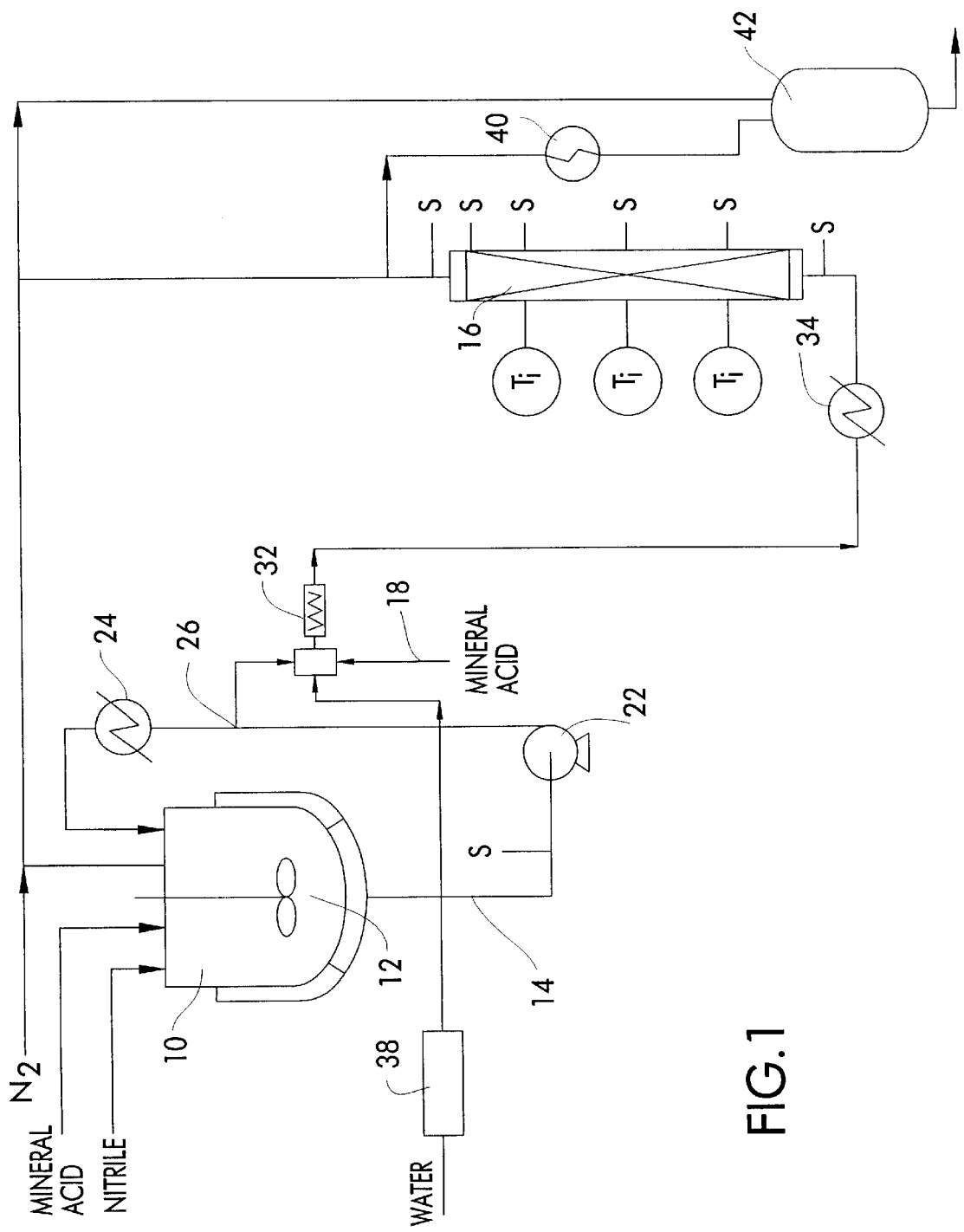
FIG. 1 is a schematic flowsheet of the process of the invention, illustrating continuous manufacture of HMBA from HMBN, water and a mineral acid.

In accordance with the present invention, a process for the preparation of HMBA is provided in which HMBN is continuously hydrolyzed in an aqueous mineral acid to form 2-hydroxy-4-methylthiobutanamide (hereinafter referred to as "nitrile hydrolysis"), and the amide is continuously hydrolyzed to form HMBA (hereinafter "amide hydrolysis"). The process is implemented utilizing an apparatus that comprises a first continuous stirred tank reactor (hereinafter "CSTR") for nitrile hydrolysis and an amide hydrolysis flow reactor, preferably a plug flow reactor (hereinafter "PFR"), for subsequent amide hydrolysis. The nitrile hydrolysis is very exothermic and is, therefore, most efficiently conducted in a CSTR back mixed for heat transfer and temperature control. The amide hydrolysis is less exothermic yet must be brought to substantial completion in order to achieve desired product quality and yield. A PFR has been found to be well suited for the amide hydrolysis because it can be configured to operate without substantial back-mixing, yet provide adequate residence time for the reaction without requiring excessive pressure drop. For example, it has been found that an industrial scale pipeline reactor can be operated at a Reynolds number in excess of about 5000 without excessive pressure drop through the reactor, while producing a hydrolyzate containing less than about 0.1. amide and less than about 0.1% nitrile on an HMBA basis.

More particularly, the invention is directed to an apparatus including a nitrile hydrolysis reactor comprising a CSTR for receiving aqueous mineral acid and HMBN feed streams. For purposes of the present invention, an aqueous mineral acid is comprised of water and up to 99 wt. % mineral acid. The aqueous mineral acid is generally sulfuric acid or hydrochloric acid. Sulfuric acid is particularly preferred. As the HMBN reacts with water within the CSTR, an aqueous hydrolysis mixture containing 2-hydroxy-4-methylthiobutanamide is formed. The amide typically hydrolyzes to some extent in the nitrile hydrolysis reactor, resulting in formation of ammonium salts and HMBA in the aqueous hydrolysis mixture. The aqueous hydrolysis mixture is continuously removed from the CSTR, cooled, and returned to the CSTR. A portion of the circulating aqueous hydrolysis mixture is removed from a forward flow port to form a nitrile hydrolysis reactor product stream. This stream is diluted to form a finishing reaction stream before being introduced to the flow reactor for completion of amide hydrolysis. Since the amide hydrolysis proceeds to some degree during the nitrile hydrolysis, it is generally preferable to dilute the nitrile hydrolysis reactor product solution as soon as practicable to provide water for amide hydrolysis and prevent liquid phase separation. Dilution also prevents precipitation of ammonium bisulfate when sulfuric acid is used. However, when the point of dilution is closely coupled to the point of withdrawal of aqueous hydrolysis solution from the CSTR, it has been found that residual nitrile may be introduced into the finishing reaction stream. Since the rate of nitrile hydrolysis is reduced by addition of dilution water, residual nitrile may be increased in the product.

It has further been discovered that residual nitrile can be reduced to very low levels by providing a modest but critical flow regime residence time for substantial completion of the nitrile hydrolysis reaction before dilution. More particularly, it has been discovered that residual nitrile is substantially extinguished by providing a nitrile hydrolysis flow regime residence time of at least about 20 seconds and, depending upon the degree of back mixing, preferably between about 30 seconds and about 5 minutes, as constituted, e.g., by the sum of the residence time of the circulating aqueous hydrolysis solution between the point of withdrawal from the CSTR and a forward flow port plus the residence time of the nitrile hydrolysis reactor product stream between the forward flow port and the point of dilution. For purposes of the present invention, residual nitrile is substantially extinguished when not more than about 0.05% by weight nitrile remains in the finishing reaction stream.

It has also been discovered that concentrated sulfuric acid, water, and HMBN can be concurrently and directly introduced into the first CSTR in order to produce within the CSTR a more dilute effective sulfuric acid strength suitable for hydrolysis of HMBN. HMBN, water and concentrated sulfuric acid can be simultaneously fed into the first CSTR without hindering the hydrolysis of HMBN despite the disparate density and viscosity of sulfuric acid and HBMN and the high heat of dilution released when sulfuric acid is diluted with water. The dilution of sulfuric acid within the reactor eliminates the need for separate acid dilution as used in a conventional process, reducing cost and maintenance of the hydrolysis system. Water and acid required for the hydrolysis reaction can be introduced in any practical combination of concentrated acid, dilute acid, and water to achieve the required concentration and proportion of mineral acid for the first hydrolysis.

Figure 3:
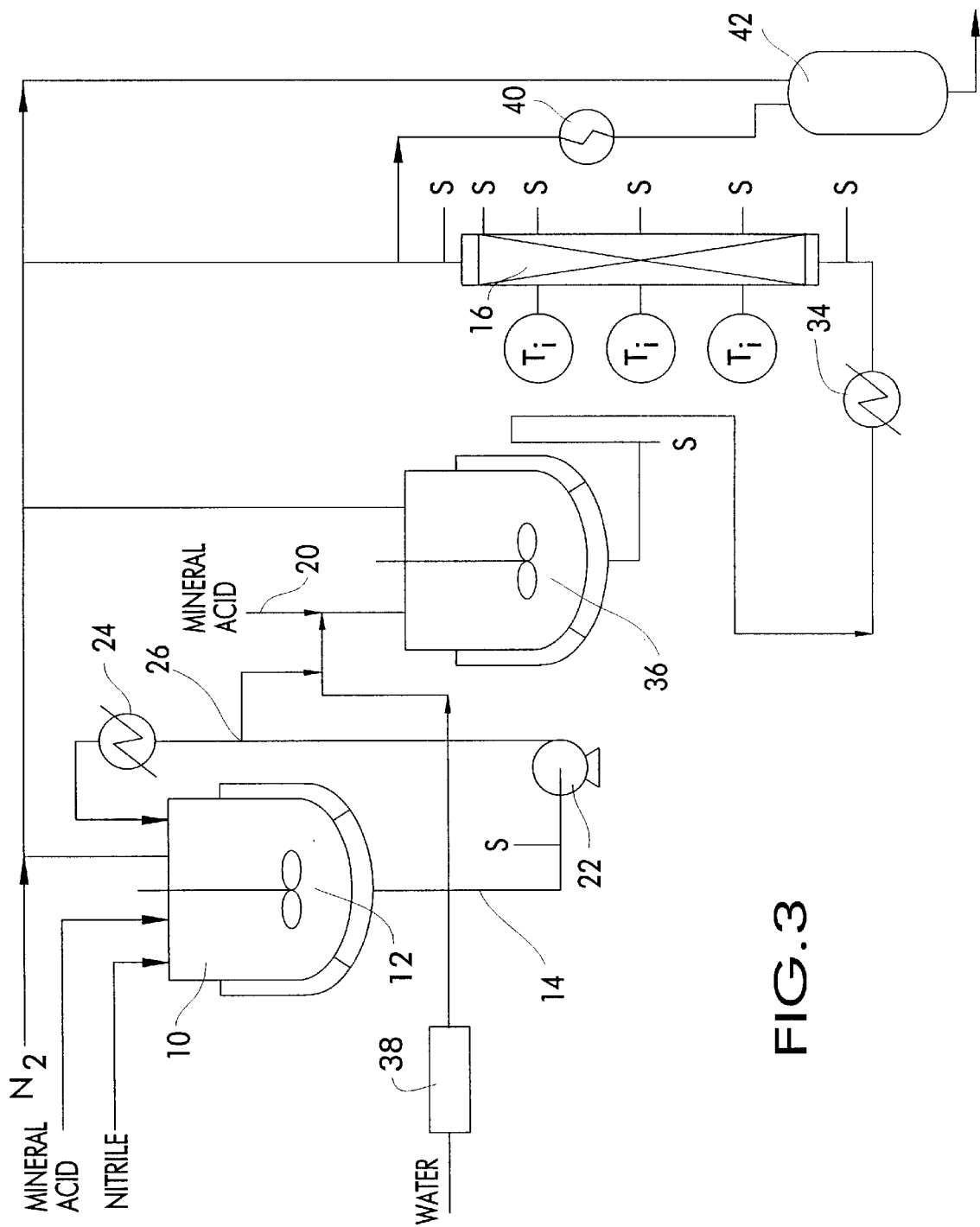
FIG. 3 is a schematic flowsheet of a process of the invention in which 2-hydroxy-4-methylthiobutanamide exiting a nitrile hydrolysis reactor is converted to HMBA in a continuous stirred tank reactor and an amide hydrolysis flow reactor operated in series.

In one embodiment of the invention illustrated in FIG. 3, the nitrile hydrolysis reactor product stream removed from the nitrile hydrolysis reactor is diluted with water to form an amide hydrolysis stream that is fed to a second CSTR before being transferred to the amide hydrolysis flow reactor. Alternatively, the nitrile hydrolysis reactor product stream and the water stream can be introduced directly to the second CSTR. A substantial portion of the amide is converted to HMBA in the second CSTR by further hydrolysis to form the finishing reaction stream. The finishing reaction stream is further hydrolyzed in an amide hydrolysis flow reactor located downstream of the second CSTR to form a finished aqueous hydrolyzate product containing HMBA. Alternatively, the second CSTR can be bypassed such that the finishing reaction stream is continuously fed directly to the amide hydrolysis flow reactor and hydrolyzed to form the hydrolyzate product. It has been discovered that the process of the invention can be operated at high productivity in one or more CSTRs in series together with a flow finishing reactor. Thus, the capital costs of implementing the process are significantly reduced as compared to the batch processes previously considered necessary in the art to provide adequate conversion at high productivity.

It has been found that such a continuous hydrolysis process can provide efficient conversion of HMBN to HMBA to produce a high quality hydrolyzate product containing very low amounts of HMBN and 2-hydroxy-4-methylthiobutanamide. In order to produce quality feed supplements containing HMBA, the process of the invention may be operated at high productivity to produce a finished aqueous hydrolyzate product comprising at least about 36 wt. % HMBA, at least about 18 wt. % ammonium salt, at least about 20 wt. % water, up to about 0.05 wt. % amide and up to about 0.05 wt. % nitrile. The HMBA within the finished aqueous hydrolyzate product includes HMBA monomer as well as dimers and other oligomers. When the mineral acid used in the hydrolysis is sulfuric acid, the finished aqueous hydrolyzate product comprises at least about 36 wt. % HMBA, at least about 30 wt. % ammonium salt, such as ammonium bisulfate or ammonium sulfate, at least about 25 wt. % water, up to about 0.05 wt. % amide and up to about 0.05 wt. % nitrile. When hydrochloric acid is used in the hydrolysis, the finished aqueous hydrolyzate product comprises at least about 50 wt. % HMBA, at least about 18 wt. % ammonium chloride, at least about 20 wt. % water, up to about 0.05 wt. % amide and up to about 0.05 wt. % nitrile. In a particularly preferred embodiment of the invention, substantially complete conversion is achieved during start up with sulfuric acid as well as at steady state so that the preferred hydrolyzate product composition may be consistently produced throughout all process operations.

An aqueous hydrolyzate product of lesser purity can also be prepared according to the process of the present invention by using a lower acid to nitrile ratio for the hydrolysis. Such an aqueous hydrolyzate product comprises at least about 30 wt. % 2-hydroxy-4-methylthiobutanoic acid, at least about 20 wt. % ammonium salt, such as ammonium sulfate or ammonium bisulfate, at least about 25 wt. % water, up to about 5 wt. % amide and up to about 0.1 wt. % nitrile, and has a color of not more than about 10 on the Gardner scale.

Ordinarily, the hydrolyzate product produced before steady state conditions are established, for example, during start up, could contain more amide and nitrile than is desired in a high quality HMBA product. It has been discovered that such composition fluctuations can be prevented by operating at a higher mineral acid to nitrile molar ratio during start up in order to establish steady state conditions very rapidly. Presumably, all of the mineral acid and HMBN are introduced into the first CSTR reactor, but the mineral acid stream can be divided to introduce one portion directly into the amide hydrolysis flow reactor. Broadly speaking, therefore, the mineral acid to nitrile molar ratio is based on the cumulative rates at which mineral acid and nitrile are introduced into the process as a whole. Operation at a higher mineral acid to nitrile ratio is achieved by controlling the rate of mineral acid flowing into the amide hydrolysis flow reactor so that it is at least stoichiometrically equivalent to the sum of the nitrile and amide flowing into that reactor. When sulfuric acid is used for the hydrolysis, the sulfuric acid to nitrile molar ratio is between about 1.0 and about 2.0 from start up of the process until steady state is established, preferably between about 1.0 and about 1.5, and more preferably between about 1.15 and about 1.25. After steady state is reached, the sulfuric acid to nitrile molar ratio is between about 0.6 and about 1.5, preferably between about 0.9 and about 1.2, and more preferably between about 0.95 and about 1.05. When hydrochloric acid is used for the hydrolysis, the steady state hydrochloric acid to nitrile molar ratio is between about 1.0 and about 1.5, preferably between about 1.05 and about 1.3, and more preferably between about 1.15 and about 1.2. The above-described preferred acid to nitrile ratios are optimal for a high productivity process. For most effective control at high productivity, the mineral acid rate is preferably at least 5% in excess of the rate equivalent to the sum of nitrile and amide. Decreasing acid to nitrile ratios can reduce color of a finished aqueous hydrolyzate product and reduce operating costs. Operation at the lower acid to nitrile ratios described herein can be preferred if low cost, low productivity production of a finished aqueous hydrolyzate product is desired.

Referring to FIG. 1, 2-hydroxy-4-methylthiobutanamide is continuously generated by the hydrolysis of HMBN in a CSTR 10. At start up of the process, a mineral acid feed stream is introduced into the reactor 10 and mixed in a back-mixed reaction zone 12 therein. HMBN is then introduced into the mineral acid stream where it reacts with water to form the amide within the aqueous hydrolysis mixture. Continuous nitrile hydrolysis occurs as the HMBN and mineral acid streams are continuously fed to the aqueous hydrolysis mixture within the reactor 10.

The mineral acid is preferably sulfuric acid having a strength of between about 50% by weight and about 70% by weight, preferably between about 60% by weight and about 70% by weight. Sulfuric acid serves as a catalyst and is not consumed in the nitrile hydrolysis reaction. However, acid is consumed by the amide hydrolysis reaction that generally occurs to some extent in the nitrile hydrolysis reactor, resulting in formation of ammonium bisulfate when sulfuric acid is used in the nitrile hydrolysis reaction. The reaction is carried out at a temperature between about 40° C. and about 70° C., preferably between about 60° C. and about 65° C., and at a total pressure of between about 0 and about 15 psig. The residence time during which the aqueous hydrolysis mixture is contained within the reactor 10 is between about 20 minutes and about 60 minutes, preferably between about 25 minutes and about 45 minutes. The residence time within the CSTR 10 is computed by dividing the volume of the aqueous hydrolysis mixture in the CSTR 10 and in the circulating line 14 by the volumetric flow rate of nitrile hydrolysis reactor product stream transferred downstream via forward flow port 26. The aqueous hydrolysis mixture produced in the CSTR 10 comprises up to about 16 wt. % HMBA, up to about 12 wt. % ammonium salt, at least about 6 wt. % water, at least about 30 wt. % amide and up to about 2 wt. % nitrile. When sulfuric acid is used, the aqueous hydrolysis mixture produced in the CSTR 10 comprises up to about 16 wt. % HMBA, up to about 12 wt. % ammonium salt, such as ammonium bisulfate or ammonium sulfate, at least about 6 wt. % water, at least about 35 wt. % amide and up to about 2 wt. % nitrile, preferably between about 5 and about 12 wt. % HMBA, between about 4 and about 9 wt. % ammonium salt, between about 10 and about 15 wt. % water, between about 35 and about 50 wt. % amide and up to about 2 wt. % nitrile, and more preferably, comprises between about 5 and about 11 wt. % HMBA, between about 4 and about 8 wt. % ammonium salt, between about 11 and about 13 wt. % water, between about 40 and about 50 wt. % amide and up to about 1 wt. % nitrile.

When hydrochloric acid is selected as the mineral acid for the nitrile hydrolysis reaction, the acid preferably has a strength of between about 30% by weight and about 40% by weight, more preferably between about 35% by weight and about 376 by weight. Hydrochloric acid serves as a catalyst and is not consumed in the nitrile hydrolysis reaction. However, hydrochloric acid is consumed by the amide hydrolysis reaction that generally occurs to some extent in the nitrile hydrolysis reactor, resulting in formation of ammonium chloride in the aqueous hydrolysis mixture. Any ammonium chloride solids can be dissolved after the finished aqueous hydrolyzate product is obtained. The reaction is carried out at a temperature between about 25° C. and about 60° C., preferably between about 45° C. and about 55° C., and at a total pressure of between about 2 and about 15 psig. The residence time during which the aqueous hydrolysis mixture is contained within the reactor 10 is between about 25 minutes and about 60 minutes, preferably between about 40 minutes and about 50 minutes. When hydrochloric acid is used, the aqueous hydrolysis mixture produced in the CSTR 10 comprises up to about 10 wt. % HMBA, up to about 5 wt. % ammonium chloride, at least about 20 wt. % water, at least about 40 wt. % amide and up to about 2 wt. % nitrile, preferably between about 2 and about 10 wt. % HMBA, between about 0.5 and about 5 wt. % ammonium chloride, between about 20 and about 30 wt. % water, between about 40 and about 60 wt. % amide and up to about 0.5 wt. % nitrile, and more preferably, comprises between about 5 and about 9 wt. % HMBA, between about 0.5 and about 4 wt. % ammonium chloride, between about 25 and about 30 wt. % water, between about 45 and about 60 wt. % amide and up to about 0.1 wt. % nitrile.

Figure 2:
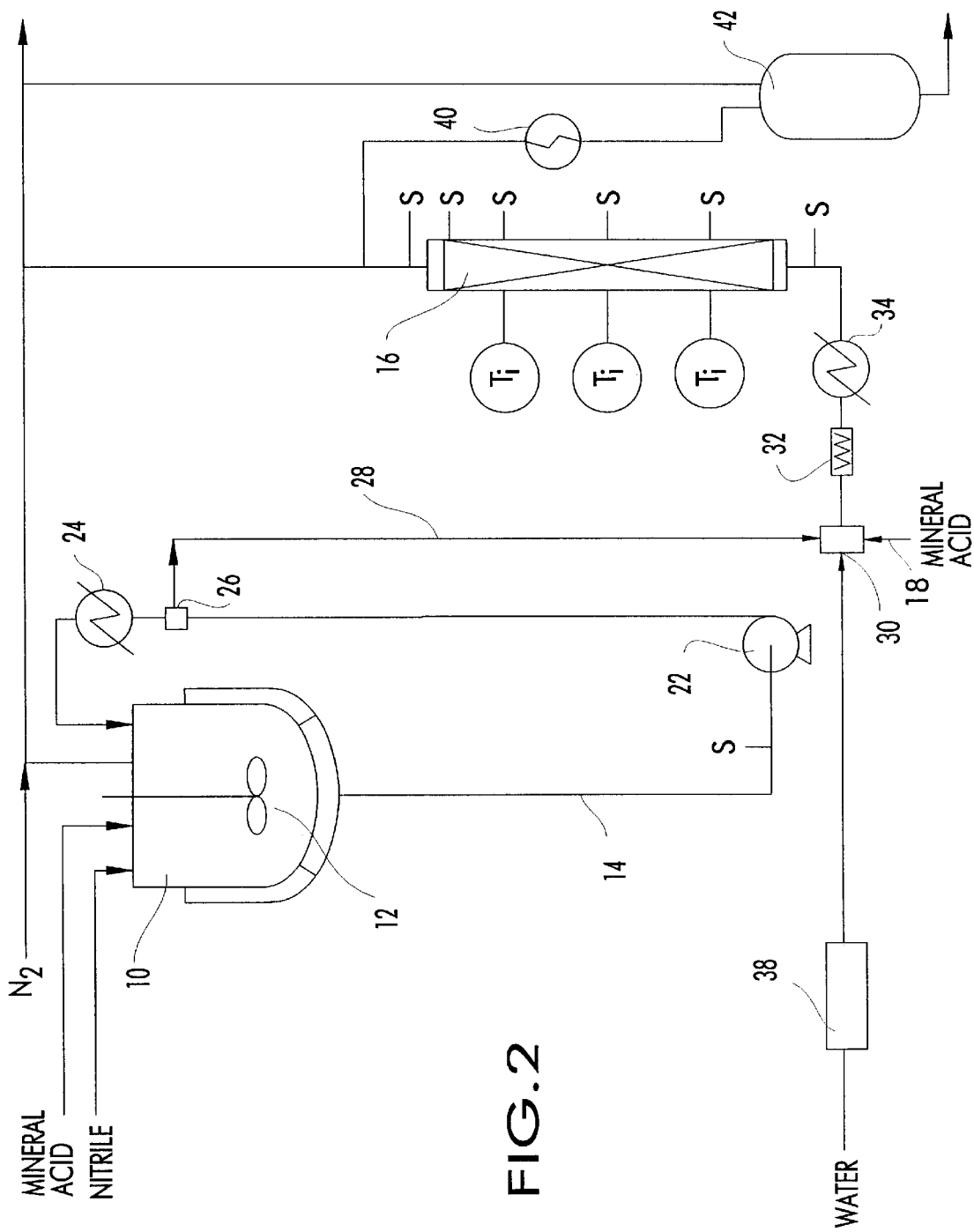
FIG. 2 is a schematic flowsheet of a preferred process of the type illustrated in FIG. 1 as modified to assure that residual HMBN is substantially extinguished.
Figure 4:
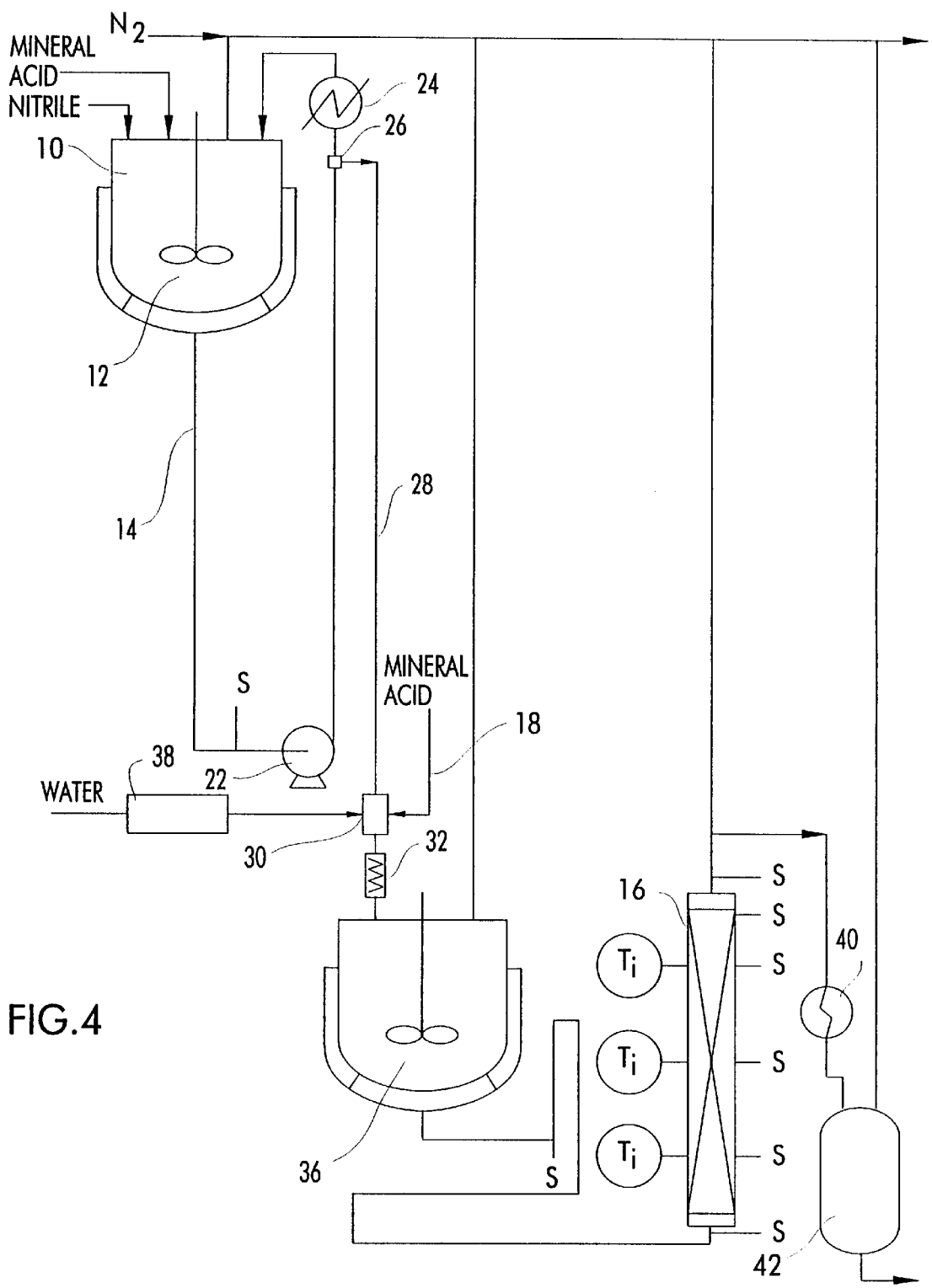
FIG. 4 is a schematic flowsheet of a preferred process of the type illustrated in FIG. 3 as modified to assure that residual HMBN is substantially extinguished.

In an alternative embodiment of the invention, the mineral acid stream can be divided such that a portion is fed to the CSTR 10 and the remainder is fed via line 18 upstream of the inlet of the in-line mixer 32 as shown in FIGS. 1, 2 and 4, or via line 20 into the amide hydrolysis mixture fed to a continuous amide hydrolysis reactor, second CSTR 36, as shown in FIG. 3. The acid to nitrile molar ratio into the CSTR 10 is between about 0.6 and about 1.5 and, preferably between about 0.8 and about 1.2. The overall molar acid to nitrile ratio is between about 0.7 and about 1.5, preferably between about 0.9 and about 1.2 and, more preferably, between about 0.95 and about 1.05. The overall molar acid to nitrile ratio, for purposes of the present invention, is the sum of any mineral acid feed streams divided by the nitrile fed to the nitrile hydrolysis reactor.

Lower acid to nitrile molar ratios are preferred when low cost, low productivity production of a finished aqueous hydrolyzate product is desired. The acid to nitrile molar ratio into the CSTR 10 under these conditions is between about 0.5 and It about 0.95 and, preferably between about 0.8 and about 0.95. The overall molar acid to nitrile ratio is between about 0.6 and about 0.95, and preferably between about 0.85 and about 0.95.

In FIG. 1, the continuous nitrile hydrolysis reactor also includes a circulation zone in fluid flow communication with the back-mixed reaction zone 12. The circulation zone comprises a circulating line 14 through which the aqueous hydrolysis mixture withdrawn from the back-mixed reaction zone 12 is continuously circulated via a pump 22. An external heat exchanger 24 is preferably included in the circulating line to remove exothermic heat of reaction by transfer to a coolant. After passing through the pump 22 and the heat exchanger 24, the aqueous hydrolysis mixture is returned to the back-mixed reaction zone 12. A portion of the aqueous hydrolysis mixture is removed from a forward flow port 26 in the circulation zone to form a nitrile hydrolysis reactor product stream which is transferred to an amide hydrolysis flow reactor 16.

The temperature of the circulating aqueous hydrolysis mixture is at least 30° C., preferably between about 40° C. and about 60° C. throughout the circulation zone. When sulfuric acid is used, the temperature is at least about 50° C., preferably between about 55° C. and about 60° C. throughout the circulation zone, and when hydrochloric acid is used, the temperature is at least about 30° C., preferably between about 40° C. and about 50° C. throughout the circulation zone. The reactor 10 can be jacketed to provide additional cooling capacity, and also to provide for heating the contents of the reactor if required during start up.

The liquid level within the reactor 10 is maintained constant by a level controller. Although the liquid level can also be controlled by gravity overflow from the reactor, the hydrolysis system is more easily designed if positive level control is utilized. A level controller is also preferred because the aqueous hydrolysis mixture is viscous. Moreover the availability of a level controller allows the working volume and residence time of the reactor to be varied at the operator's selection, e.g., to adapt to changes in throughput.

In a particularly preferred embodiment of the invention, a flow regime residence time of at least about 20 seconds is provided to effectively complete the nitrile hydrolysis before dilution of the reaction solution for carrying out the amide hydrolysis. FIG. 2 illustrates such an arrangement. The aqueous hydrolysis mixture leaving the back-mixed reaction zone 12 is preferably not removed from the suction side of a pump 22, but is instead transferred through the circulating line 14 via the pump 22 to a forward flow port 26 located on the circulating line a distance sufficiently downstream of the pump to provide a flow reaction regime, preferably a plug flow section in which a portion of residual nitrile is consumed. Advantageously, the forward flow port 26 is so located to provide a residence time of at least about 3 seconds, generally between about 3 seconds to about 15 seconds, and preferably between about 5 seconds and about 10 seconds in the circulating line 14 upstream of port 26 to promote reaction of residual nitrile. Because of the substantial volume of the aqueous hydrolysis mixture that is circulated through the heat exchanger 24 for removal of the heat of reaction, the flow regime in the circulating line is readily maintained in a turbulent regime, so that the portion of the circulating line 14 between the point of withdrawal from CSTR 10 and port 26 functions essentially as a plug flow reactor.

A portion of the circulating aqueous hydrolysis mixture is removed as a nitrile hydrolysis reactor product stream from forward flow port 26, while the remainder of the circulating stream flows back to CSTR 10. In order to assure that residual nitrile is most effectively reduced, a flow regime residence time of at least about 30 seconds, preferably between about 30 seconds and about 5 minutes, more preferably between about 30 seconds and about 3 minutes and, more preferably between about 2 minutes and about 3 minutes is provided for completion of the nitrile hydrolysis reaction in a flow regime nitrile extinction reaction region constituted of the portion of the circulation line between the exit of the CSTR 10 and the forward flow port 26 together with the nitrile hydrolysis reactor product transfer line 28 upstream of dilution point 30. Since, as discussed above, a residence time of between about 3 seconds and about 15 seconds is advantageously provided between the point of withdrawal from the CSTR 10 and the port 26, the transfer line 28 is preferably configured to provide a residence time of between about 10 seconds and about 5 minutes, more preferably between about 30 seconds and about 5 minutes and, most preferably, between about 1 minute and about 3 minutes. In order to provide the requisite residence time without excessive flow velocity and pressure drop, transfer line 28 may be configured for laminar flow but, whatever the flow conditions, at least one equivalent back-mixed reaction zone is provided in this transport line. The transfer line 28 can also be configured for turbulent flow. Preferably, the velocity is such as to provide the equivalent of at least about two equivalent back-mixed reaction zones, more preferably between about 3 and about 5 sequential back mixed reaction zones in the aforesaid nitrile extinction reaction region. In a preferred embodiment, the residual HMBN in the nitrile hydrolysis reactor product stream at the point of dilution 30 is at least about 0.05 wt. % based on the sum of the HMBA and amide contained in the nitrile hydrolysis reactor product stream. In a particularly preferred embodiment, the residual HMBN in the nitrile hydrolysis reactor product stream at the point of dilution 30 is not greater than about 0.01 wt. % based on the sum of the HMBA and amide contained in the nitrile hydrolysis reactor product stream.

The transfer line 28 is preferably configured as a vertical downcomer so that nitrogen or other gases that may become entrained in the aqueous hydrolyzate mixture in the CSTR 10 can be disengaged from the downward flowing liquid and vented through the top of the downcomer transfer line 28. Although a horizontal configuration can be used, any gases could disengage from forward flow in a horizontal line and accumulate, reducing effective liquid volume in the line.

As the nitrile hydrolysis reactor product stream is transferred downstream of the forward flow port 26, it is mixed with a water stream and any divided portion of the mineral acid flow in an in-line mixer 32 to form a finishing reaction stream. The nitrile hydrolysis reactor product stream is mixed with the water stream and any acid stream to assure that a homogeneous liquid mixture is introduced to the amide hydrolysis flow reactor 16. Any water stream also further dilutes mineral acid within the finishing reaction stream, provides reaction water to be consumed during amide hydrolysis, and reduces the viscosity of the finishing reaction stream. When sulfuric acid is used, dilution of the nitrile hydrolysis reactor product stream may avoid liquid phase separation or precipitation of ammonium bisulfate within the amide hydrolysis flow reactor 16. Ammonium chloride will typically precipitate when hydrochloric acid is used for hydrolysis. The water stream is typically introduced at a rate that provides sulfuric acid strength in the finishing reaction stream of between about 30% and about 50% by weight on an organic-free basis, preferably between about 35% to about 45% by weight, more preferably about 43% by weight. If about 30% to about 38% by weight hydrochloric acid is used, water addition is not required. The hydrochloric acid strength in the finishing reaction stream is between about 30% and about 40% by weight on an organic-free basis, preferably between about 35% to about 38% by weight, more preferably about 36% by weight.

The water stream can be heated before being mixed with the nitrile hydrolysis reactor product stream to form the finishing reaction stream, or the finishing reaction stream can be heated before being fed to the amide hydrolysis flow reactor 16 to provide the desired reactor operating temperature. Typically, the water stream is heated to a temperature of between about 60° C. and about 100° C., preferably between about 70° C. and about 90° C., and, more preferably between about 75° C. and about 80° C. If the water is not preheated or the temperature of the finishing reaction stream is too low, the water stream can be brought to the requisite temperature in a preheater 34. The residence time of the finishing reaction stream between the point of dilution 30 and the inlet to the amide hydrolysis flow reactor is not critical. The finishing reaction stream is well mixed within this region and then enters the amide hydrolysis flow reactor 16.

In the amide hydrolysis flow reactor, some of the residual HMBN is hydrolyzed to form additional amide and amide is substantially hydrolyzed to form HMBA. Preferably, the molar ratio of water to amide fed to the amide hydrolysis flow reactor is between about 5 and about 10. The flow rate of the finishing reaction stream is preferably operated to maintain suitable velocity within the amide hydrolysis flow reactor to maintain turbulence and minimize axial back mixing therein. Preferably the equivalent of at least about two sequential back-mixed reaction zones, more preferably at least about 35 sequential back-mixed reaction zones, is provided in aforesaid amide hydrolysis flow reactor.

As indicated above, at a given residence time in the amide hydrolysis flow reactor, it has been found that conversion may be substantially increased by increasing the mineral acid/nitrile molar ratio in the feed. Experience has shown that in some instances steady state is obtained in about two hours during start up when the sulfuric acid/nitrile molar ratio is 1.0, yet steady state conditions, and complete conversion, may be obtained almost immediately when the sulfuric acid/nitrile molar ratio is 1.2. Rapid establishment of steady state conditions enables consistent production of a high quality hydrolyzate product that comprises up to about 0.05 wt. % amide and up to about 0.05 wt. % nitrile upon leaving the amide hydrolysis flow reactor 16.

The expense of the excess mineral acid, however, may be prohibitive if an increased mineral acid/nitrile molar ratio is maintained during routine operation of the process after steady state conditions are established. Thus, it is preferable to use a sulfuric acid/nitrile molar ratio of between about 1.0 and about 1.5, preferably between about 1.15 and about 1.25, only from initial start up until steady state conditions are established in the amide hydrolysis flow reactor in order to avoid preparation of off-specification hydrolyzate product during start-up. Such a molar ratio is obtained when the molar excess of sulfuric acid added to the amide hydrolysis flow reactor 16 is between about 0 and about 50%, preferably between about 15 and about 25%, over that stoichiometrically equivalent to the amide and HMBN introduced to the amide hydrolysis flow reactor. After steady state is established, the sulfuric acid/nitrile molar ratio can then be adjusted to, and maintained at, a more cost effective molar ratio of between about 0.9 and about 1.2, preferably between about 0.95 and about 1.05. The water feed rate into the mixer 32 may be increased to avoid liquid phase separation of organic and aqueous phases when a sulfuric acid/nitrile molar ratio below 1.0 is used. When hydrochloric acid is used for the hydrolysis, the hydrochloric acid to nitrile molar ratio during steady state is between about 1.0 and about 1.5, preferably between about 1.05 and about 1.3, and more preferably between about 1.1 and about 1.2. Such a molar ratio is obtained when the molar excess of hydrochloric acid added to the amide hydrolysis flow reactor 16 is between about 0 and about 50%, preferably between about 5 and about 30%, more preferably between about 10 and about 20%, over that stoichiometrically equivalent to the amide and HMBN introduced to the amide hydrolysis flow reactor.

It has been discovered that operation of the amide hydrolysis flow reactor at a high mineral acid/nitrile molar ratio during start up improves conversion of amide to HMBA within the amide hydrolysis flow reactor 16 without darkening the color of the hydrolyzate product. Despite the increased severity of reaction conditions provided by a high acid/nitrile ratio, it has unexpectedly been discovered that acid/nitrile molar ratio does not significantly affect hydrolyzate color. Moreover, the high acid to nitrile molar ratio also allows amide hydrolysis flow reactor operation at a lower temperature during steady state operation, therefore producing a light colored hydrolyzate product.

The hydrolyzate product leaving the amide hydrolysis flow reactor 16 has a light color of between about 5 to about 10, preferably between about 5 to about 7, as measured using a Gardner calorimeter. Color is adversely affected by excessive amide hydrolysis flow reactor temperatures and residence time within the amide hydrolysis flow reactor 16. The amide hydrolysis flow reactor operates at a temperature between about 70° C. and about 120° C. When the amide hydrolysis flow reactor is operated adiabatically, the temperature rises along the flow path as the reaction product absorbs the adiabatic heat of reaction, reaching a point on the flow path (hot spot) at which the temperature reaches a plateau, and beyond which it may drop slightly if conditions are less than perfectly adiabatic. The peak temperature in the amide hydrolysis flow reactor is preferably between about 900C and about 120° C., more preferably between about 90° C. and about 105° C. The residence time of the finishing reaction stream within the amide hydrolysis flow reactor is between about 30 minutes and about 100 minutes, preferably between about 50 minutes and about 70 minutes. When the amide hydrolysis flow reactor is operated at a temperature above 110° C., a darker hydrolyzate may be produced. However, an amide hydrolysis flow reactor temperature below 90° C. may result in incomplete amide hydrolysis unless a higher acid to nitrile molar ratio is employed. Darkening of the hydrolyzate product can also occur if the residence time exceeds about 120 minutes. A light colored hydrolyzate product is produced when an acid/nitrile molar ratio of between about 1.1 and about 1.5 is used during start up and normal operation when the amide hydrolysis flow reactor 16 is operated at a moderate temperature of between about 70 and about 95° C., preferably between about 80° C. and about 90° C. The amide hydrolysis flow reactor temperature can be reduced when it is operated adiabatically by lowering the temperature of the water stream entering the mixer 32. If the finishing reaction stream is introduced into the preheater 34 (FIG. 1) before it is introduced to the amide hydrolysis flow reactor, the heat applied to the preheater can be reduced to lower the amide hydrolysis flow reactor operating temperature. Alternatively, cooling and/or heating may be provided to control the amide hydrolysis flow reactor temperature when the amide hydrolysis flow reactor is operated isothermally. When a second CSTR 36 precedes the amide hydrolysis flow reactor 16 as shown in FIG. 3, a darkened hydrolyzate product may be produced if the operating temperature of the second CSTR is too high. A light colored hydrolyzate product is produced when the above described acid/nitrile molar ratio is used and the second CSTR is operated at a moderate temperature of between about 70 and about 95° C., preferably between about 80° C. and about 90° C.

The flow reactors best suited for use in the amide hydrolysis process of the invention are plug flow reactors configured for operation at a Peclet number of at least 50 at a PFR operating temperature of at least 90° C. The Peclet number (Pe) is a measure of axial back mixing within the PFR as defined by the following equation:

$$Pe = uL/D$$

where: u=velocity, L=length, and D=axial dispersion coefficient. The Peclet number of a PFR is inversely proportional to axial back-mixing. Axial back mixing is effectively minimized when the Peclet number is at least 50, preferably between about 50 and about 200 or more, and residence time is between about 40 and about 100 minutes, preferably between about 50 and about 60 minutes.

The PFR 16 of the present invention may be a pipeline PFR or a packed column PFR filled with a packing material. The amide hydrolysis reaction is non-zero order, but the kinetics of reaction have been found sufficiently favorable that high conversion may be realized within the relatively modest residence times noted above, and without substantial pressure drop. More particularly, it has been found that, where the nitrile has been substantially converted to amide, and the nitrile concentration is not greater than about 2% by weight in the stream entering the plug flow reactor, the residual amide and nitrile concentrations may each be reduced to not greater than about 0.2% by weight on an HMBA basis in a pipeline reactor that is operated with a velocity of the reacting stream in the turbulent flow range regime, for example, at a Reynolds number of at least about 3000, preferably at least about 5000. Provided that the nitrile/amide ratio of the finishing reaction stream entering the reactor is not greater than about 1% by weight in the stream entering the PFR, the amide and nitrile concentrations in the reaction product may each be reduced to not greater than about 0.1% by weight, HMBA basis. For the relatively modest residence time required to achieve such conversion, a PFR reactor can be operated at turbulent velocity without excessive pressure drop. Moreover, it has been found that the desired conversion may be attained at a modest operating temperature, in the range of between 90° C. and about 105° C., which does not require a high pressure reactor, and which allows the preparation of a product having a light color.

Alternatively, a packed column PFR may be used to carry out the final hydrolysis reaction. By use of structured packing, a packed column reactor may be operated at a significantly lower velocity than a pipeline reactor without significant back mixing due to wall effects or channeling. The packing promotes turbulence and radial mixing, and minimizes axial back mixing, dead spots and channelling of flow so that all fluid elements travel through the PFR in about the same residence time. Thus, a packed column reactor may have a substantially greater diameter and a more compact configuration than a pipeline reactor. It is particularly advantageous where reactants or products are of high viscosity.

However, for the process of the invention, it has been found that a pipeline reactor, i.e., an elongate tubular reactor substantially devoid of internal packing or other internal flow obstructions, is preferred. While a slightly greater degree of axial back mixing per unit length may be incurred in a pipeline reactor, the kinetics of the nitrile and amide hydrolysis have been discovered to allow nearly quantitative conversion with the modest residence times and low pressure drops described above. Because of low pressure drop incurred even at high velocity in a reactor suitable for the process of the invention, a pipeline reactor may be configured, i.e., with a high L/D (length to diameter) ratio, to operate at a very high Peclet number, typically in excess of 200, and readily in excess of 2000. Additionally, a pipeline reactor for the process of the invention can be constructed of relatively inexpensive materials of construction, e.g., teflon-lined carbon steel pipe. For a packed column reactor, more exotic materials of construction may be required. A pipeline reactor also affords greater flexibility since it can be operated at a much greater turndown ratio than a packed column, in the latter of which conversion declines sharply below a well defined threshold velocity. Threshold velocity in a packed column is attained in the transition between laminar and turbulent flow.

The amide hydrolysis flow reactor 16 is insulated to compensate for heat losses to the atmosphere. The heat of reaction generated during the amide hydrolysis is sufficient for autothermal operation under adiabatic conditions. Advantageously, the finishing reaction stream can enter the amide hydrolysis flow reactor at a temperature below the reaction temperature for the amide hydrolysis. During autothermal operation, the heat of reaction generated by amide hydrolysis increases the temperature within the amide hydrolysis flow reactor, lessening the likelihood that a hot spot will form therein. The temperature profile in the amide hydrolysis flow reactor can be measured through several temperature sensors $T_i$ (FIGS. 1–4) along the length of the reactor. The water feed temperature can be adjusted to achieve the desired temperature profile in the amide hydrolysis flow reactor by increasing or decreasing the heat supplied to the water feed stream by the water heater 38 before it enters the mixer 32 to form the finishing reaction stream. Additionally, the temperature of the finishing reaction stream exiting the mixer 32 can be raised through the use of preheater 34 to increase the amide hydrolysis flow reactor operating temperature.

Although residual nitrile hydrolyzes in the inlet portion of the amide hydrolysis flow reactor, the nitrile hydrolysis should proceed sufficiently to completion in the CSTR 10 and in the nitrile extinction reaction region comprising the portion of the circulation zone upstream of the forward flow port and the zone within which the nitrile hydrolysis reactor product stream flows between the forward flow port 26 and the point of dilution 30. Heat of reaction from hydrolysis of substantial quantities of nitrile in the amide hydrolysis flow reactor potentially creates hot spots within the reactor. Although hot spot temperatures of as much as 110° C. to about 120° C. can be tolerated within the amide hydrolysis flow reactor, the hydrolyzate product can darken significantly under such conditions. Substantially extinguishing the nitrile within the nitrile hydrolysis reactor product stream allows for operation of the amide hydrolysis flow reactor at a lower temperature to provide a light colored finished aqueous hydrolyzate product.

The amide hydrolysis flow reactor operates at a total pressure of between about 0 and about 15 psig. A pressure control valve at the outlet of the amide hydrolysis flow reactor provides up to 15 psig back pressure to avoid boiling in the reactor system when the amide hydrolysis flow reactor operates at a temperature higher than 105° C.

Advantageously, amide hydrolysis samples may be withdrawn from sample valves S (FIGS. 1–4) and analyzed via gas chromatography to determine the amide hydrolysis composition profile along the length of the amide hydrolysis flow reactor. Once steady state conditions are established, a hydrolyzate sample can be removed from the amide hydrolysis flow reactor outlet every eight to twelve hours and quantitatively analyzed to monitor product quality.

The finished aqueous hydrolyzate product exiting the amide hydrolysis flow reactor 16 flows through a cooler 40 before being stored in a hydrolyzate product surge tank 42. The nitrile hydrolysis reactor, the amide hydrolysis reactors and the hydrolyzate product surge tank utilized in the processes of the present invention are operated under the same overhead pressure (preferably about 10 psig) by employing a common vent header that is blanketed with nitrogen and controlled by a pressure controller that relieves pressure by venting gases to an incinerator header when pressure exceeds about 15 psig. Venting may remove volatile organic sulfur compounds such as methyl sulfide, methyl disulfide, and methyl mercaptan, which are by-products of the reaction. The vapor emissions are less than 0.5 scf per 1000 lbs. HMBA product, usually less than 0.3 scf per 1000 lbs. product. Emissions of 0.2 scf/1000 lbs. HMBA and even lower are readily achievable, especially where only a single CSTR is used.

HMBA, or a salt or derivative thereof, can be recovered from the aqueous hydrolyzate product for use in making animal feed supplements. For example, the HMBA in the hydrolyzate can be recovered for use in a liquid phase animal feed supplement comprising between about 80% and about 98% by weight, preferably between about 80% and about 95% by weight, of the total of weight proportions of HMBA, and between about 2% and about 20% by weight, preferably between about 5% and about 20% by weight water, and having a color of not greater than about 8 as measured on the Gardner scale, a kinematic viscosity at 25° C. as measured by a Cannon-Fenske viscometer of not greater than about 500 centistokes, preferably 90centistokes, and which, upon subjection to accelerating rate colorimetry exhibits neither exothermic nor endothermic thermochemical effects at any temperature less than about 150° C.

The HMBA can be recovered from the finished aqueous hydrolyzate product by neutralization with ammonium hydroxide as described by Hernandez et al. U.S. Pat. No. 4,912,257, which is incorporated herein by reference, or by extraction methods such as that described by Ruest et al. U.S. Pat. No. 4,524,077, which is incorporated herein by reference.

WO 96/01808, WO 96/01809, and WO 96/05173, which are incorporated herein by reference, describe methods for preparation of an ammonium salt of HMBA, for preparation of concentrated HMBA by sulfuric acid hydrolysis of nitrile, and for recovery of HMBA by thin film evaporation with solvent recovery, respectively. More particularly, WO 96/01808 describes preparation of an ammonium salt by neutralizing the finished aqueous hydrolyzate product and using solvent extraction to form an organic phase containing HMBA and an ammonium acid salt aqueous phase. The application states that the organic phase is then treated with ammonia to form a second aqueous phase containing an ammonium salt of HMBA and an organic solvent phase, and the ammonium salt of HMBA is recovered from the second aqueous phase. Ammonia is said to be recovered by treating the ammonium acid salt solution with sodium hydroxide to form sodium chloride or sodium sulfate which may be more easily disposed of. WO 96/01809 describes formation of concentrated HMBA by extracting a finished aqueous sulfuric acid hydrolyzate product with an organic solvent to form an HMBA-containing organic phase and an aqueous phase, and evaporating the HMBA-containing organic phase to provide concentrated 98% HMBA containing less than 4 wt. % water. WO 96/05173 describes recovery of HMBA by evaporating a finished aqueous sulfuric acid hydrolyzate product to obtain a practically water-free, HMBA-containing salt residue, treating the residue with an organic solvent to form a suspension, separating the solids from the suspension to form an HMBA-containing solution, removing the organic solvent from the HMBA-containing solution to obtain an HMBA residue, and adding water to the HMBA residue to form an HMBA solution.

The prior art includes various other methods for recovery of an HMBA or HMBA salt product, including at least several which have been practiced commercially. Whatever process may be selected by one skilled in the art for recovery of HMBA product from a hydrolyzate, advantages accrue from initial preparation of the aqueous hydrolyzate product according to the processes of the present invention. The hydrolyzate produced in accordance with the invention is highly suited for use in any operative process for recovery of the product acid or salt.

Salts of HMBA can also be prepared from the finished aqueous hydrolyzate product by methods described by Cummins et al, U.S. Pat. No. 4,310,690, Nufer U.S. Pat. No. 3,272,860, and Blake et al, U.S. Pat. Nos. 2,938,053 and 2,745,745, which are incorporated herein by reference. Cummins describes preparation of a calcium salt of HMBA by mixing an aqueous hydrolyzate containing HMBA and ammonium chloride with a mixture of sodium chloride and a calcium salt, reacting the mixture with sodium hydroxide, reacting the resulting solution with a calcium hydroxide slurry to form the calcium salt of HMBA, and separating the calcium salt of HMBA. Blake et al. describe formation of ammonium and calcium salts of HMBA by neutralizing sulfuric acid in an aqueous hydrolyzate containing HMBA and ammonium sulfate by adding calcium hydroxide, filtering the mixture to remove calcium sulfate, reacting the filtrate with a calcium hydroxide slurry, filtering the mixture to remove calcium sulfate, and drying the filtrate to recover a composition containing a calcium salt of HMBA, an ammonium salt of HMBA, and small amounts of calcium sulfate and water. Blake et al. also describe preparation of the calcium salt of HMBA by reacting calcium carbonate with an aqueous hydrolyzate containing HMBA, sulfuric acid, and ammonium sulfate to form the ammonium salt of HMBA and calcium sulfate, separating the calcium sulfate, reacting the remaining liquid with calcium hydroxide to form the calcium salt of HMBA and ammonium hydroxide, heating the mixture to decompose ammonium hydroxide and drive off ammonia, filtering the resulting mixture to remove calcium sulfate and calcium hydroxide, and evaporating water from the mixture to form a concentrated slurry of the calcium salt of HMBA, filtering the slurry and drying the filter cake to obtain the calcium salt of HMBA. Nufer describes formation of a calcium salt of HMBA by mixing HMBA with a monoalkyl ether of ethylene glycol, reacting the mixture with a calcium oxide-ethylene glycol ether slurry, filtering the resulting slurry, and drying the filter cake to recover the calcium salt of HMBA. Other methods of forming salts or derivatives of HMBA are well known, and include methods of preparing salts of HMBA by direct reaction of a metal oxide or other base with isolated or partially isolated HMBA as described in U.S. Pat. Nos. 4,855,495, 4,579,962 and 4,335,257, which are incorporated herein by reference.

FIG. 3 illustrates an embodiment of the present invention wherein the amide hydrolysis reaction is conducted in the amide hydrolysis flow reactor 16 and a second CSTR 36 upstream of the amide hydrolysis flow reactor. The second CSTR enables easy handling of the viscous amide, thoroughly mixes the amide hydrolysis mixture with the dilution water and any divided portion of the mineral acid stream within the second CSTR and controls the temperature of the finishing reaction stream, resulting in a relatively low viscosity of the latter stream as introduced into the amide hydrolysis flow reactor. The nitrile hydrolysis reaction takes place in CSTR 10 and the nitrile hydrolysis reactor product stream exiting the CSTR 10, a water feed stream, and any divided portion of a mineral acid stream via line 20 are introduced into the second CSTR 36 wherein a substantial portion of the amide is hydrolyzed to HMBA. For purposes of the present invention, a substantial portion of the amide is hydrolyzed when more than 50% by weight, preferably between about 50% and about 80% by weight, of the amide is hydrolyzed to HMBA. The residence time during which the amide hydrolysis mixture is contained within the second CSTR 36 is between about 30 minutes and about 80 minutes, preferably between about 40 minutes and about 60 minutes. The residence time within the second CSTR 36 is computed by dividing the liquid volume of the second CSTR by the volumetric flow rate of the finishing reaction stream exiting the second CSTR. The liquid level in the second CSTR can be controlled by gravity overflow to the amide hydrolysis flow reactor 16 or preferably by positive level control as previously described.

The amide hydrolysis reaction is initiated in the second CSTR at a temperature between about 70° C. and about 120° C., preferably between about 90° C. and about 105° C., and at a total pressure of between about 0 and about 15 psig. Conversion to HMBA is generally improved by operating the second CSTR at an elevated temperature between about 90° C. and about 110° C. The second CSTR 36 is typically provided with a steam heated jacket in order to maintain the operating temperature. If the temperature sensors $T_i$ (FIG. 3) detect a hot spot within the amide hydrolysis flow reactor, the operating temperature of the second CSTR can be lowered.

The amide hydrolysis reaction is substantially carried out in the second CSTR, producing a finishing reaction stream that is introduced into the amide hydrolysis flow reactor 16. The finishing reaction stream comprises at least about 30 wt. % HMBA, at least about 17 wt. % ammonium salt, at least about 15 wt. % water, up to about 10 wt. % amide and up to about 1 wt. % nitrile. Preferably, the finishing reaction stream comprises between about 30 and about 50 wt. % HMBA, between about 17 and about 30 wt. % ammonium salt, between about 15 and about 30 wt. % water, between about 1 and about 6 wt. % amide and up to about 0.1 wt. % nitrile. When sulfuric acid is used, the finishing reaction stream comprises at least about 31 wt. % HMBA, at least about 20 wt. % ammonium salt, such as ammonium bisulfate or ammonium sulfate, at least about 20 wt. % water, up to about 5 wt. % amide and up to about 1 wt. % nitrile, and preferably between about 32 and about 42 wt. % HMBA, between about 20 and about 30 wt. % ammonium salt, between about 22 and about 30 wt. % water, between about 2 and about 4 wt. % amide and up to about 0.1 wt. % nitrile. When hydrochloric acid is used, the finishing reaction stream comprises at least about 45 wt. % HMBA, at least about 17 wt. % ammonium chloride, at least about 15 wt. % water, up to about 8 wt. % amide and up to about 1 wt. % nitrile and, preferably between about 45 and about 50 wt. % HMBA, between about 17 and about 19 wt. % ammonium chloride, between about 18 and about 22 wt. % water, between about 2 and about 6 wt. % amide and up to about 0.1 wt. % nitrile. The amide hydrolysis is then completed within the amide hydrolysis flow reactor as described above for FIG. 1.

FIG. 4 is a preferred, modified process of the process shown in FIG. 3. Residence time of the nitrile hydrolysis reactor product stream is prolonged between the hydrolysis reactor outlet and the second CSTR to extinguish residual nitrile as described above regarding FIG. 2. When the nitrile hydrolysis reactor product stream is diluted with water and/or any divided portion of the mineral acid, an amide hydrolysis stream is formed which is fed to the second CSTR. Amide hydrolysis occurs in the second CSTR to produce a finishing reaction stream to be transferred to the amide hydrolysis flow reactor.

Figure 5:
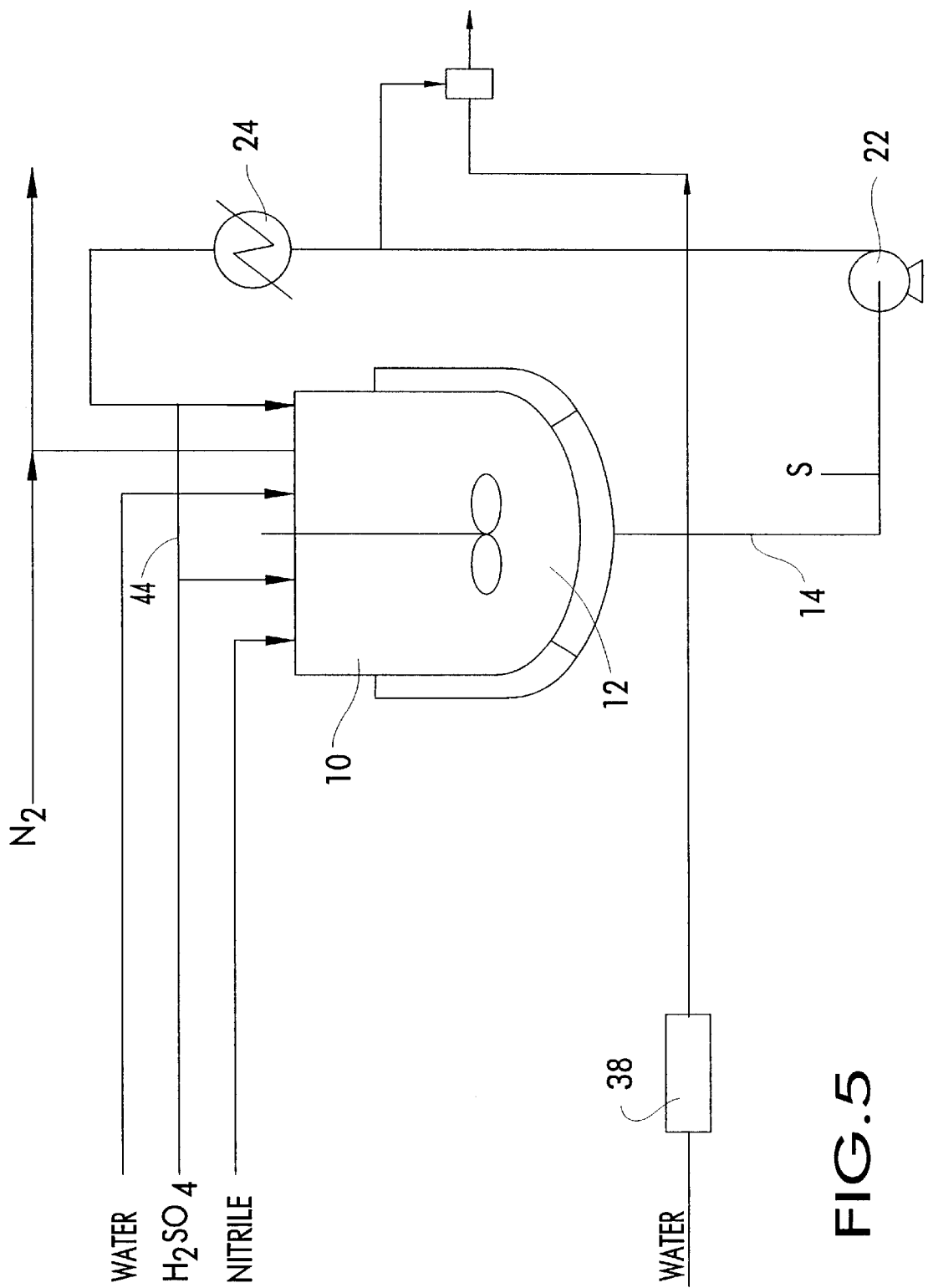
FIG. 5 is a schematic illustration of a continuous stirred tank reactor adapted for conversion of HMBN to 2-hydroxy-4-methylthiobutanamide while a concentrated sulfuric acid stream is introduced into the reactor.
Figure 6:
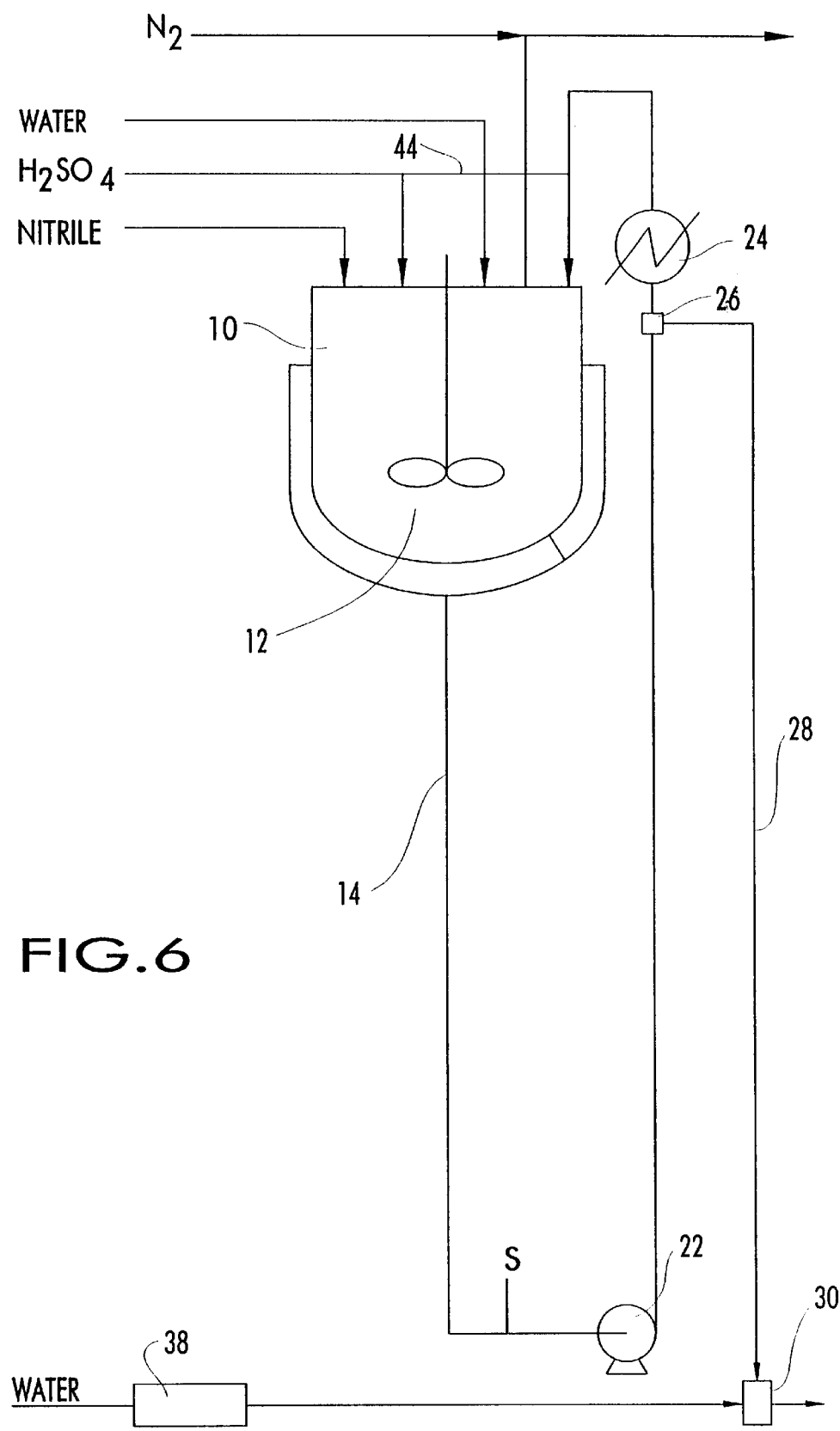
FIG. 6 is a schematic illustration of a continuous stirred tank reactor adapted for the HMBN to amide conversion as shown in FIG. 5 while extinguishing HMBN prior to dilution.

FIGS. 5 and 6 illustrate a preferred embodiment of the invention wherein the CSTR 10 can be adapted in the processes shown in FIGS. 1 through 4 to receive concentrated sulfuric acid, HMBN, and water feed streams. The HMBN and water feed stream are fed directly to the CSTR. The concentrated sulfuric acid stream is either mixed with the circulating stream in the circulating line or is fed directly to the CSTR. The concentrated sulfuric acid stream may be fed directly to CSTR 10 but is preferably fed via line 44 to the circulating line downstream of the heat exchanger 24 so that the concentrated acid stream is thoroughly mixed with the aqueous hydrolysis mixture before it is returned to the CSTR 10. When all streams are simultaneously fed to the CSTR, sulfuric acid is diluted in the reactor as the nitrile hydrolysis reaction occurs. In either case, a separate acid dilution system is not required and associated installation and maintenance costs are avoided. The concentrated sulfuric acid introduced into the aqueous hydrolysis mixture has a strength of between about 70% by weight and about 99% by weight, preferably between about 90% by weight and about 98% by weight. The aqueous hydrolysis mixture within the CSTR 10 has a strength of between about 50% by weight and about 70% by weight, preferably between about 60% by weight and about 70% by weight of sulfuric acid on an organic-free basis. The aqueous hydrolysis mixture is continuously pumped through an external heat exchanger 24 at a high circulation rate to remove heat of reaction. A pump 22 circulates the aqueous hydrolysis mixture between CSTR 10 and an external heat exchanger 24, in which exothermic heat of reaction is removed by transfer to a coolant. The heat exchanger also removes the heat generated by dilution of sulfuric acid when concentrated sulfuric acid is fed directly to reactor 10.

The process of the present invention provides an improved method for preparing HMBA. High productivity can be achieved using such a process because it can be operated continuously to provide greater throughput than a conventional batch process. The process significantly reduces capital and maintenance costs associated with batch processes, for example, by eliminating the need for separate sulfuric acid dilution when concentrated sulfuric acid is introduced to a reactor without prior dilution. The process also affords improved control of reaction conditions as compared to conventional batch hydrolysis systems. Such improved control of the hydrolysis reactions enables production of a hydrolyzate product of consistently high quality. The process vent emissions are significantly reduced as compared to conventional batch systems because filling and emptying of tanks and operation at non-steady state conditions is eliminated.

The following examples are presented to describe preferred embodiments and utilities of the present invention and are not meant to limit the present invention unless otherwise stated in the claims appended hereto.

EXAMPLE 1

Figure 7:
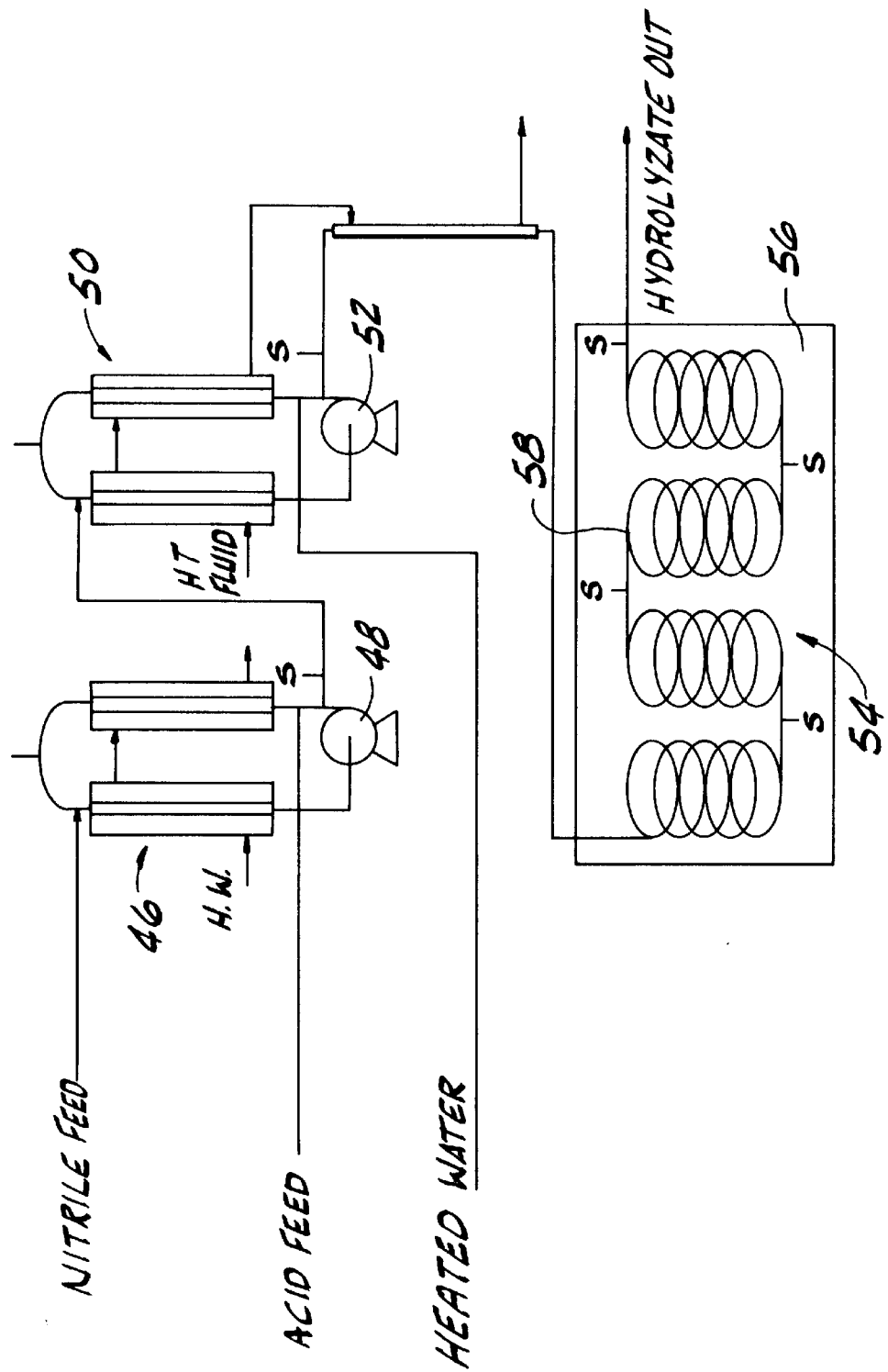
FIG. 7 is a schematic flowsheet of a bench-scale continuous hydrolysis process in which 2-hydroxy-4-methylthiobutanamide exiting a first recirculating reactor is converted to HMBA in a second recirculating reactor and a plug flow reactor operated in series.

Bench scale equipment as shown in FIG. 7 was used to demonstrate the continuous hydrolysis process.

Nitrile (2-hydroxy-4-methylthiobutanenitrile) and 65% aqueous sulfuric acid were continuously pumped at rates of 1.01 g/min and 1.167 g/min, respectively, into a well-mixed recirculating reactor 46 having a liquid volume of 42.1 milliliters. The reaction temperature was controlled at 65° C. through cooling jackets provided on the recirculating reactor loop, which removed the heat released from the nitrile hydrolysis reaction. A pump 48 recirculated the aqueous hydrolysis mixture in the reactor loop. The residence time of the reactor 46 based on the total feed rate was 25.4 minutes. At the outlet of the reactor, a sample was periodically removed during steady state conditions. All sampling ports are designated with an S in FIG. 7. The sample was analyzed by a gas chromatographic method to determine the hydrolyzate product composition leaving the reactor. The gas chromatography result showed that practically all nitrile feed was hydrolyzed and converted to amide and approximately 15% of the formed amide was further hydrolyzed in this reactor to form HMBA, the final hydrolysis product.

The amide rich hydrolyzate leaving the recirculating reactor 46 was fed continuously into the second recirculating reactor 50 which is similar to the first recirculating reactor 46 but has a liquid volume of 119.3 milliliters. A water feed at 0.57 g/min was also introduced into the second well-mixed reactor that provided a residence time of 52.6 minutes. The temperature of this reactor loop was maintained at 102° C. via a heating fluid jacket provided on the recirculating reactor loop. A pump 52 recirculated the hydrolyzate in the reactor loop. An outlet sample from the reactor 50 was obtained and analyzed by gas chromatography which revealed that approximately 94.5% of the feed amide was hydrolyzed to HMBA.

The outlet from the second recirculating reactor 50 continuously entered the final finishing reactor that was constructed of a series of four coils 54 of Teflon tubing. The finishing reactor was placed inside a constant temperature oven 56 for preventing heat losses to the ambient, thus maintaining a temperature of 102° C. throughout the reactor coils 54. This isothermal PFR having a total liquid volume of 91 milliliters and a corresponding 43 minutes residence time was designed to assure completion of the amide hydrolysis. In this case, the hydrolysis of amide was completed at the outlet of the third coil 58. The hydrolyzate product taken from the outlet of the PFR was analyzed and contained 35% HMBA, with the remaining material being water and by-product ammonium bisulfate. The color of the hydrolyzate product was 6–7 on the Gardner color scale.

EXAMPLES 2–9

The same continuous bench scale equipment as used in Example 1 was also used to determine the effect of residence time and reaction temperature on conversion. The acid to nitrile feed ratio of each example was maintained at approximately a 1.0 molar stoichiometric ratio. At the outlet of each recirculating reactor and the end of each coil of the PFR, a sample (indicated as RECIRC and S, respectively, in Tables 1–8 below) was removed during steady state conditions and was analyzed by a gas chromatographic method to determine the hydrolysis mixture composition leaving the reactor or coil. The hydrolysis mixture composition and the temperature and residence time in each reactor or coil are shown in Tables 1–8 below. The remainder of the product included water and ammonium bisulfate. The results, based on various feed rates (1.01–2.33 grams/min. nitrile feed) and temperatures (60–65° C. for nitrile hydrolysis and 90–120° C. for amide hydrolysis) illustrate that increasing residence time and reaction temperatures improves the conversion of both hydrolysis reactions. However, increasing temperatures also resulted in an increase in product color.

EXAMPLE 2

Nitrile at 1.01 g/min was fed to the first recirculating reactor, along with 1.15 g/min 64.7% sulfuric acid, giving a 0.99 acid/nitrile molar ratio. A water feed at 0.55 g/min was also introduced into the second recirculating reactor. The hydrolysis mixture composition and the temperature and residence time in each reactor or coil are shown in Table 1 below.

TABLE 1

|  | RECIRC-I | RECIRC-II | S1 | S2 | S3 |
|---|---|---|---|---|---|
| Temperature (° C.) | 64 | 103 | 104 | 104 | 104 |
| Residence Time (min) | 25 | 53 | 11 | 11 | 11 |
| Hydrolysis Mixture Composition (wt. %) | | | | | |
| Nitrile | 0.11 | trace | trace | trace | trace |
| HMBA | 8.3 | 34 | 33 | 35 | 33 |
| Amide | 38 | 2.7 | 0.70 | 0.12 | 0.03 |

Hydrolyzate Product Color: 6–7 on Gardner scale

EXAMPLE 3

Nitrile at 1.01 g/min was fed to the first recirculating reactor, along with 1.16 g/min 64.7% sulfuric acid, giving a 0.99 acid/nitrile molar ratio. A water feed at 0.54 g/min was also introduced into the second recirculating reactor. The hydrolysis mixture composition and the temperature and residence time in each reactor or coil are shown in Table 2 below.

TABLE 2

|  | RECIRC-I | RECIRC-II | S1 | S2 | S3 |
|---|---|---|---|---|---|
| Temperature (° C.) | 62 | 98 | 102 | 102 | 102 |
| Residence Time (min) | 25 | 53 | 11 | 11 | 11 |
| Hydrolysis Mixture Composition (wt. %) | | | | | |
| Nitrile | 0.22 | 0.05 | 0.05 | trace | 0.035 |
| HMBA | 7.8 | 33 | 38 | 38 | 39 |
| Amide | 35 | 3.5 | 0.81 | 0.18 | 0.09 |

Hydrolyzate Product Color: 5–6 on Gardner scale

EXAMPLE 4

Nitrile at 1.43 g/min was fed to the first recirculating reactor, along with 1.65 g/min 64.7% sulfuric acid, giving a 0.99 acid/nitrile molar ratio. A water feed at 0.76 g/min was also introduced into the second recirculating reactor. The hydrolysis mixture composition and the temperature and residence time in each reactor or coil are shown in Table 3 below.

TABLE 3

|  | RECIRC-I | RECIRC-II | S1 | S2 | S3 |
|---|---|---|---|---|---|
| Temperature (° C.) | 65 | 105 | 105 | 105 | 105 |
| Residence Time (min) | 18 | 36 | 7.7 | 7.7 | 7.7 |
| Hydrolysis Mixture Composition (wt. %) | | | | | |
| Nitrile | 0.36 | 0.06 | 0.05 | trace | trace |
| HMBA | 6.7 | 34 | 36 | 37 | 38 |
| Amide | 39 | 3.1 | 0.79 | 0.28 | trace |

Hydrolyzate Product Color: 6–7 on Gardner scale

EXAMPLE 5

Nitrile at 1.45 g/min was fed to the first recirculating reactor, along with 1.69 g/min 64.7% sulfuric acid, giving a 1.0 acid/nitrile molar ratio. A water feed at 0.78 g/min was also introduced into the second recirculating reactor. The hydrolysis mixture composition and the temperature and residence time in each reactor or coil are shown in Table 4 below.

TABLE 4

|  | RECIRC-I | RECIRC-II | S1 | S2 | S3 | S4 |
|---|---|---|---|---|---|---|
| Temperature (° C.) | 65 | 90 | 90 | 90 | 90 | 90 |
| Residence Time (min) | 18 | 37 | 7.7 | 7.7 | 7.7 | 7.3 |
| Hydrolysis Mixture Composition (wt. %) | | | | | | |
| Nitrile | 0.37 | trace | trace | trace | trace | trace |
| HMBA | 6.1 | 32 | 36 | 37 | 36 | 37 |
| Amide | 40 | 5.8 | 2.1 | 0.99 | 0.60 | 0.40 |

Hydrolyzate Product Color: 4 on Gardner scale

EXAMPLE 6

Nitrile at 2.0 g/min was fed to the first recirculating along with 2.33 g/min 65% sulfuric acid, giving a 1.01 acid/nitrile molar ratio. A water feed at 1.09 g/min was also introduced into the second recirculating reactor. The hydrolysis mixture composition and the temperature and residence time in each reactor or coil are shown in Table 5 below.

TABLE 5

|  | RECIRC-I | RECIRC-II | S1 | S2 | S3 | S4 |
|---|---|---|---|---|---|---|
| Temperature (° C.) | 65 | 105 | 105 | 105 | 105 | 105 |
| Residence Time (min) | 13 | 26 | 5.4 | 5.4 | 5.4 | 5.2 |
| Hydrolysis Mixture Composition (wt. %) | | | | | | |
| Nitrile | 0.45 | 0.09 | trace | 0.04 | trace | 0.06 |
| HMBA | 5.3 | 34 | 36 | 36 | 36 | 37 |
| Amide | 40 | 3.3 | 0.84 | 0.28 | 0.12 | 0.07 |

Hydrolyzate Product Color: 6–7 on Gardner scale

EXAMPLE 7

Nitrile at 1.42 g/min was fed to the first recirculating reactor, along with 1.65 g/min 650 sulfuric acid, giving a 1.01 acid/nitrile molar ratio. A water feed at 0.795 g/min was also introduced into the second recirculating reactor. The hydrolysis mixture composition and the temperature and residence time in each reactor or coil are shown in Table 6 below.

TABLE 6

|  | RECIRC-I | RECIRC-II | S1 | S2 | S3 |
|---|---|---|---|---|---|
| Temperature (° C.) | 60 | 120 | 120 | 120 | 120 |
| Residence Time (min) | 18 | 36 | 7.5 | 7.5 | 7.5 |
| Hydrolysis Mixture Composition (wt. %) | | | | | |
| Nitrile | 0.23 | 0.05 | trace | trace | trace |
| HMBA | 5.2 | 36 | 35 | 36 | 36 |
| Amide | 39 | 1.5 | trace | trace | trace |

Hydrolyzate Product Color: 17 on Gardner scale

EXAMPLE 8

Nitrile at 1.43 g/min was fed to the first recirculating reactor, along with 1.66 g/min 65% sulfuric acid, giving a 1.0 acid/nitrile molar ratio. A water feed at 0.78 g/min was also introduced into the second recirculating reactor. The hydrolysis mixture composition and the temperature and residence time in each reactor or coil are shown in Table 7 below.

TABLE 7

|  | RECIRC-I | RECIRC-II | S1 | S2 | S4 |
|---|---|---|---|---|---|
| Temperature (° C.) | 65 | 100 | 100 | 100 | 100 |
| Residence Time (min) | 18 | 36 | 7.6 | 7.6 | 7.3 |
| Hydrolysis Mixture Composition (wt. %) | | | | | |
| Nitrile | 0.26 | 0.10 | NA | NA | trace |
| HMBA | 7.0 | 34 | NA | NA | 37 |
| Amide | 36 | 3.7 | NA | NA | 0.05 |

Hydrolyzate Product Color: 6 on Gardner scale

EXAMPLE 9

Nitrile at 1.04 g/min was fed to the first recirculating reactor, along with 1.15 g/min 65% sulfuric acid, giving a 0.96 I acid/nitrile molar ratio. A water feed at 0.57 g/min was also introduced into the second recirculating reactor. The hydrolysis mixture composition and the temperature and residence time in each reactor or coil are shown in Table 8 below.

TABLE 8

|  | RECIRC-I | RECIRC-II | S1 | S2 | S3 | S4 |
|---|---|---|---|---|---|---|
| Temperature (° C.) | 65 | 100 | 100 | 100 | 100 | 100 |
| Residence Time (min) | 25 | 52 | 11 | 11 | 11 | 11 |
| Hydrolysis Mixture Composition (wt. %) | | | | | | |
| Nitrile | 0.36 | 0.08 | 0.05 | 0.05 | 0.04 | trace |
| HMBA | 8.7 | 35 | 37 | 36 | 35 | 34 |
| Amide | 39 | 3.6 | 0.89 | 0.37 | 0.17 | 0.05 |

Hydrolyzate Product Color: 6 on Gardner scale

EXAMPLES 10–20

Figure 8:
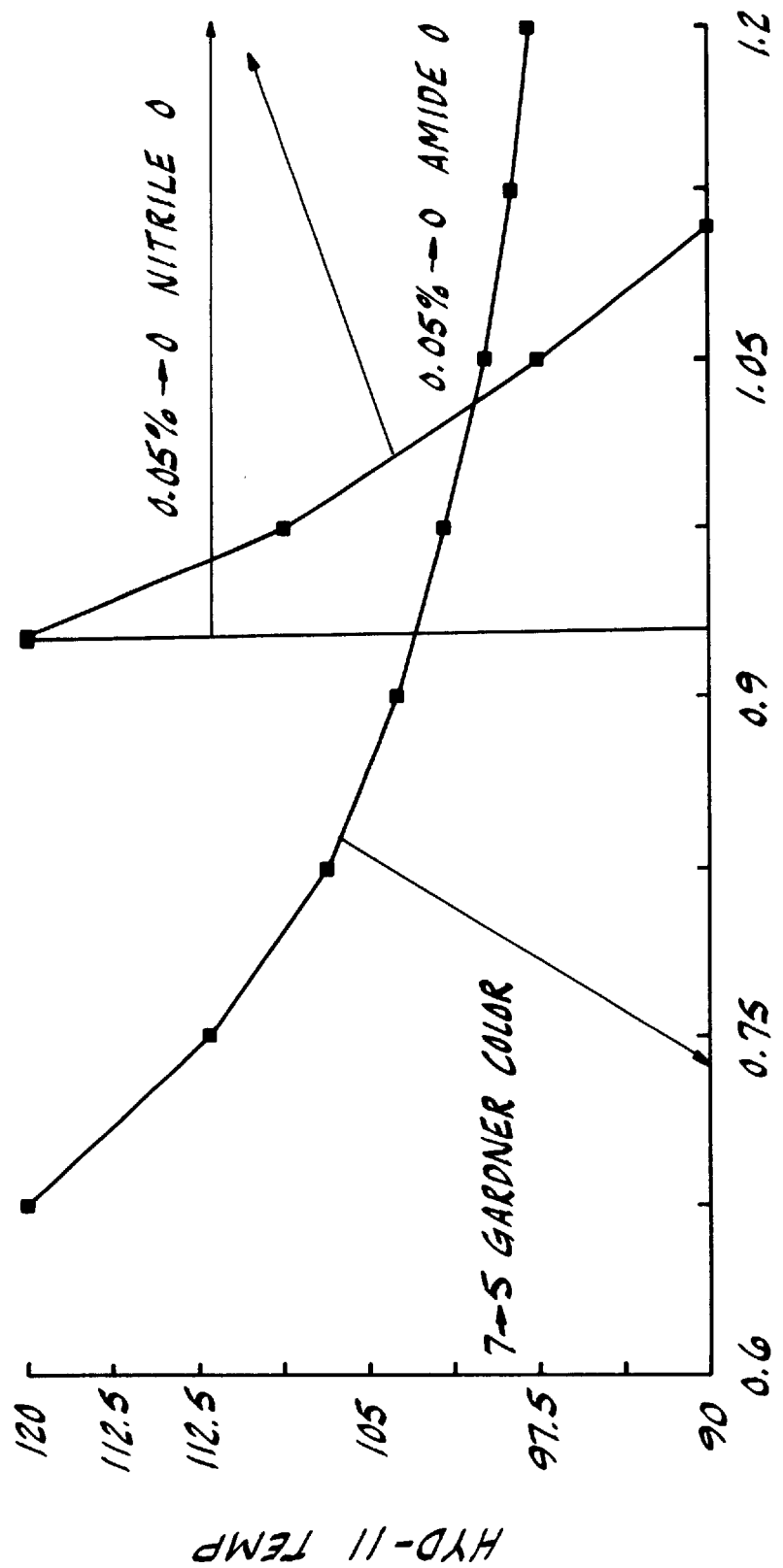
FIG. 8 is a plot showing amide concentration, nitrile concentration, and Gardner color for the hydrolyzate product as a function of acid/nitrile molar ratio fed to the first reactor and temperature within the plug flow reactor based on bench scale experiments.

The effect of acid/nitrile feed molar ratio on the reaction conversion, as well as the coupling effect of this ratio with reaction temperature was determined. In these examples, the nitrile feed rate was essentially constant and the water feed rate was adjusted for various 65% sulfuric acid feeds to assure the same water content of the final hydrolyzate from each run. At the outlet of each reactor and the end of each coil of the PFR, a sample was removed during steady state conditions and was analyzed a gas chromatographic method to determine the hydrolyzate product composition leaving the reactor or coil. The hydrolysis mixture composition and the temperature and residence time in each reactor or coil are shown below. The remainder of the hydrolyzate included water and ammonium bisulfate. Based on the range of the variables that were analyzed, i.e., acid/nitrile molar ratio from 0.6 to 1.2 and amide hydrolysis temperature from 90–120° C., an optimum range of conditions were derived as shown in FIG. 8 for the fixed residence (or nitrile feed rate) tested. Within the range of 90–101° C. and 1.0–1.2 acid/nitrile ratio, any combination of temperature and acid/nitrile molar ratio will result in a satisfactory product containing up to 0.05% by weight amide, up to 0.05% by weight nitrile and having a color of between 5 and 7 on a Gardner scale.

EXAMPLE 10

Nitrile at 1.02 g/min was fed to the first recirculating reactor, along with 1.03 g/min 64.75% sulfuric acid, giving a 0.88 acid/nitrile molar ratio. A water feed at 0.53 g/min was also introduced into the second recirculating reactor. The hydrolysis mixture composition and the temperature and residence time in each reactor or coil are shown in Table 9 below.

TABLE 9

|  | RECIRC-I | RECIRC-II | S1 | S2 | S3/S4 |
|---|---|---|---|---|---|
| Temperature (° C.) | 65 | 105 | 105 | 105 | 105 |
| Residence Time (min) | 27 | 53 | 11 | 11 | 11 |
| Hydrolysis Mixture Composition (wt. %) | | | | | |
| Nitrile | 0.80 | 0.31 | 0.35 | 0.40 | NA |
| HMBA | 8.3 | 35 | 41 | 49 | NA |
| Amide | 41 | 3.7 | 1.7 | 0.96 | NA |

Hydrolyzate Product Color: 6–7 on Gardner scale

EXAMPLE 11

Nitrile at 0.99 g/min was fed to the first recirculating reactor, along with 0.70 g/min 65% sulfuric acid, giving a 0.62 acid/nitrile molar ratio. A water feed at 0.94 g/min was also introduced into the second recirculating reactor. The hydrolysis mixture composition and the temperature and residence time in each reactor or coil are shown in Table 10 below.

TABLE 10

|  | RECIRC-I | RECIRC-II | S1 | S2 | S3 | S4 |
|---|---|---|---|---|---|---|
| Temperature (° C.) | 65 | 90 | 90 | 90 | 90 | 90 |
| Residence Time (min) | 32 | 53 | 11 | 11 | 11 | 11 |
| Hydrolysis Mixture Composition (wt. %) | | | | | | |
| Nitrile | 5.2 | 2.2 | 2.4 | 2.5 | 2.5 | 2.5 |
| HMBA | 7.9 | 25 | 27 | 29 | 30 | 30 |
| Amide | 45 | 9.5 | 7.4 | 5.9 | 5.2 | 4.6 |

Hydrolyzate Product Color: 5 on Gardner scale

EXAMPLE 12

Nitrile at 1.01 g/min was fed to the first recirculating reactor, along with 1.37 g/min 64.75% sulfuric acid, giving a 1.19 acid/nitrile molar ratio. A water feed at 0.53 g/min was also introduced into the second recirculating reactor. The hydrolysis mixture composition and the temperature and residence time in each reactor or coil are shown in Table 11 below.

TABLE 11

|  | RECIRC-I | RECIRC-II | S1 | S2 | S3 | S4 |
|---|---|---|---|---|---|---|
| Temperature (° C.) | 65 | 90 | 90 | 90 | 90 | 90 |
| Residence Time (min) | 23 | 50 | 10 | 10 | 10 | 10 |
| Hydrolysis Mixture Composition (wt. %) | | | | | | |
| Nitrile | trace | trace | trace | trace | trace | trace |
| HMBA | 7.7 | 31 | 35 | 34 | 35 | 35 |
| Amide | 33 | 2.8 | 0.72 | 0.17 | 0.03 | trace |

Hydrolyzate Product Color: 5 on Gardner scale

EXAMPLE 13

Nitrile at 1.01 g/min was fed to the first recirculating reactor, along with 0.70 g/min 65% sulfuric acid, giving a 0.60 acid/nitrile molar ratio. A water feed at 0.90 g/min was also introduced into the second recirculating reactor. The hydrolysis mixture composition and the temperature and residence time in each reactor or coil are shown in Table 12 below.

TABLE 12

|  | RECIRC-I | RECIRC-II | S1 | S2 | S3 | S4 |
|---|---|---|---|---|---|---|
| Temperature (° C.) | 65 | 120 | 120 | 120 | 120 | 120 |
| Residence Time (min) | 32 | 52 | 11 | 11 | 11 | 10 |
| Hydrolysis Mixture Composition (wt. %) | | | | | | |
| Nitrile | 6.0 | 2.6 | 2.7 | 2.2 | 2.7 | 2.3 |
| HMBA | 7.7 | 27 | 32 | 29 | 34 | 31 |
| Amide | 44 | 5.4 | 4.0 | 1.4 | 1.8 | 1.4 |

Hydrolyzate Product Color: 10 on Gardner scale

EXAMPLE 14

Nitrile at 1.0 g/min was fed to the first recirculating reactor, along with 1.37 g/min 64.75% sulfuric acid, giving a 1.19 acid/nitrile molar ratio. A water feed at 0.513 g/min was also introduced into the second recirculating reactor. The hydrolysis mixture composition and the temperature and residence time in each reactor or coil are shown in Table 13 below.

TABLE 13

|  | RECIRC-I | RECIRC-II | S1 | S2 | S3 | S4 |
|---|---|---|---|---|---|---|
| Temperature (° C.) | 65 | 120 | 120 | 120 | 120 | 120 |
| Residence Time (min) | 23 | 50 | 10 | 10 | 10 | 10 |
| Hydrolysis Mixture Composition (wt. %) | | | | | | |
| Nitrile | trace | trace | trace | trace | trace | trace |
| HMBA | 8.5 | 34 | 34 | 35 | 35 | 34 |
| Amide | 31 | 0.44 | trace | trace | trace | trace |

Hydrolyzate Product Color: 12+ on Gardner scale

EXAMPLE 15

Nitrile at 1.0 g/min was fed to the first recirculating reactor, along with 1.05 g/min 64.75% sulfuric acid, giving a 0.91 acid/nitrile molar ratio. A water feed at 0.67 g/min was also introduced into the second recirculating reactor. The hydrolysis mixture composition and the temperature and residence time in each reactor or coil are shown in Table 14 below.

TABLE 14

|  | RECIRC-I | RECIRC-II | S1 | S2 | S3 | S4 |
|---|---|---|---|---|---|---|
| Temperature (° C.) | 65 | 105 | 105 | 105 | 105 | 105 |
| Residence Time (min) | 27 | 53 | 11 | 11 | 11 | 11 |
| Hydrolysis Mixture Composition (wt. %) | | | | | | |
| Nitrile | 0.39 | 0.11 | 0.11 | 0.11 | 0.10 | 0.09 |
| HMBA | 8.9 | 34 | 34 | 37 | 38 | 38 |
| Amide | 37 | 4.0 | 1.5 | 0.71 | 0.32 | 0.20 |

Hydrolyzate Product Color: 6 on Gardner scale

EXAMPLE 16

Nitrile at 1.02 g/min was fed to the first recirculating reactor, along with 0.71 g/min 64.75% sulfuric acid, giving a 0.6 acid/nitrile molar ratio. A water feed at 0.93 g/min was also introduced into the second recirculating reactor. The hydrolysis mixture composition and the temperature and residence time in each reactor or coil are shown in Table 15 below.

TABLE 15

|  | RECIRC-I | RECIRC-II | S1 | S2 | S3 | S4 |
|---|---|---|---|---|---|---|
| Temperature (° C.) | 65 | 120 | 120 | 120 | 120 | 120 |
| Residence Time (min) | 32 | 52 | 11 | 11 | 11 | 10 |
| Hydrolysis Mixture Composition (wt. %) | | | | | | |
| Nitrile | 5.7 | 2.5 | 2.7 | 2.6 | 2.6 | 2.5 |
| HMBA | 8.5 | 29 | 33 | 34 | 35 | 35 |
| Amide | 45 | 6.2 | 4.3 | 2.6 | 2.0 | 1.5 |

Hydrolyzate Product Color: 6 on Gardner scale

EXAMPLE 17

Nitrile at 1.02 g/min was fed to the first recirculating reactor, along with 0.69 g/min 65% sulfuric acid, giving a 0.59 acid/nitrile molar ratio. A water feed at 0.90 g/min was also introduced into the second recirculating reactor. The hydrolysis mixture composition and the temperature and residence time in each reactor or coil are shown in Table 16 below.

TABLE 16

|  | RECIRC-I | RECIRC-II | S1 | S2 | S3 | S4 |
|---|---|---|---|---|---|---|
| Temperature (° C.) | 65 | 90 | 90 | 90 | 90 | 90 |
| Residence Time (min) | 32 | 53 | 11 | 11 | 11 | 10 |
| Hydrolysis Mixture Composition (wt. %) | | | | | | |
| Nitrile | 6.0 | 3.4 | 3.2 | 3.2 | 3.3 | 3.3 |
| HMBA | 8.2 | 25 | 27 | 28 | 29 | 30 |
| Amide | 44 | 12 | 8.0 | 7.5 | 6.6 | 5.7 |

Hydrolyzate Product Color: 5 on Gardner scale

EXAMPLE 18

Nitrile at 1.02 g/min was fed to the first recirculating reactor, along with 1.38 g/min 65% sulfuric acid, giving a 1.18 acid/nitrile molar ratio. A water feed at 0.54 g/min was also introduced into the second recirculating reactor. The hydrolysis mixture composition and the temperature and residence time in each reactor or coil are shown in Table 17 below.

TABLE 17

|  | RECIRC-I | RECIRC-II | S1 | S2 | S3 | S4 |
|---|---|---|---|---|---|---|
| Temperature (° C.) | 65 | 90 | 90 | 90 | 90 | 90 |
| Residence Time (min) | 23 | 50 | 10 | 10 | 10 | 10 |
| Hydrolysis Mixture Composition (wt. %) | | | | | | |
| Nitrile | trace | trace | trace | trace | trace | trace |
| HMBA | 7.2 | 31 | 35 | 35 | 35 | 36 |
| Amide | 34 | 2.9 | 0.15 | 0.24 | trace | trace |

Hydrolyzate Product Color: 5 on Gardner scale

EXAMPLE 19

Nitrile at 1.03 g/min was fed to the first recirculating reactor, along with 1.39 g/min 65% sulfuric acid, giving a 1.17 acid/nitrile molar ratio. A water feed at 0.52 g/min was also introduced into the second recirculating reactor. The hydrolysis mixture composition and the temperature and residence time in each reactor or coil are shown in Table 18 below.

TABLE 18

|  | RECIRC-I | RECIRC-II | S1 | S2 | S3 | S4 |
|---|---|---|---|---|---|---|
| Temperature (° C.) | 65 | 120 | 120 | 120 | 120 | 120 |
| Residence Time (min) | 23 | 50 | 10 | 10 | 10 | 10 |
| Hydrolysis Mixture Composition (wt. %) | | | | | | |
| Nitrile | trace | trace | trace | trace | trace | trace |
| HMBA | 7.1 | 33 | 33 | 34 | 34 | 48 |
| Amide | 35 | 0.39 | trace | trace | trace | trace |

Hydrolyzate Product Color: >18 on Gardner scale

EXAMPLE 20

Nitrile at 1.02 g/min was fed to the first recirculating reactor, along with 1.05 g/min 65% sulfuric acid, giving a 0.90 acid/nitrile molar ratio. A water feed at 0.63 g/min was also introduced into the second recirculating reactor. The hydrolysis mixture composition and the temperature and residence time in each reactor or coil are shown in Table 19 below.

TABLE 19

|  | RECIRC-I | RECIRC-II | S1 | S2 | S3 | S4 |
|---|---|---|---|---|---|---|
| Temperature (° C.) | 65 | 105 | 105 | 105 | 105 | 105 |
| Residence Time (min) | 27 | 53 | 11 | 11 | 11 | 11 |
| Hydrolysis Mixture Composition (wt. %) | | | | | | |
| Nitrile | 0.38 | 0.06 | 0.09 | 0.06 | 0.09 | 0.09 |
| HMBA | 8.9 | 28 | 39 | 31 | 41 | 38 |
| Amide | 40 | 2.5 | 0.97 | 0.31 | 0.18 | 0.10 |
| Hydrolyzate Product Color: 7 on Gardner scale | | | | | | |

EXAMPLE 21

Figure 9:
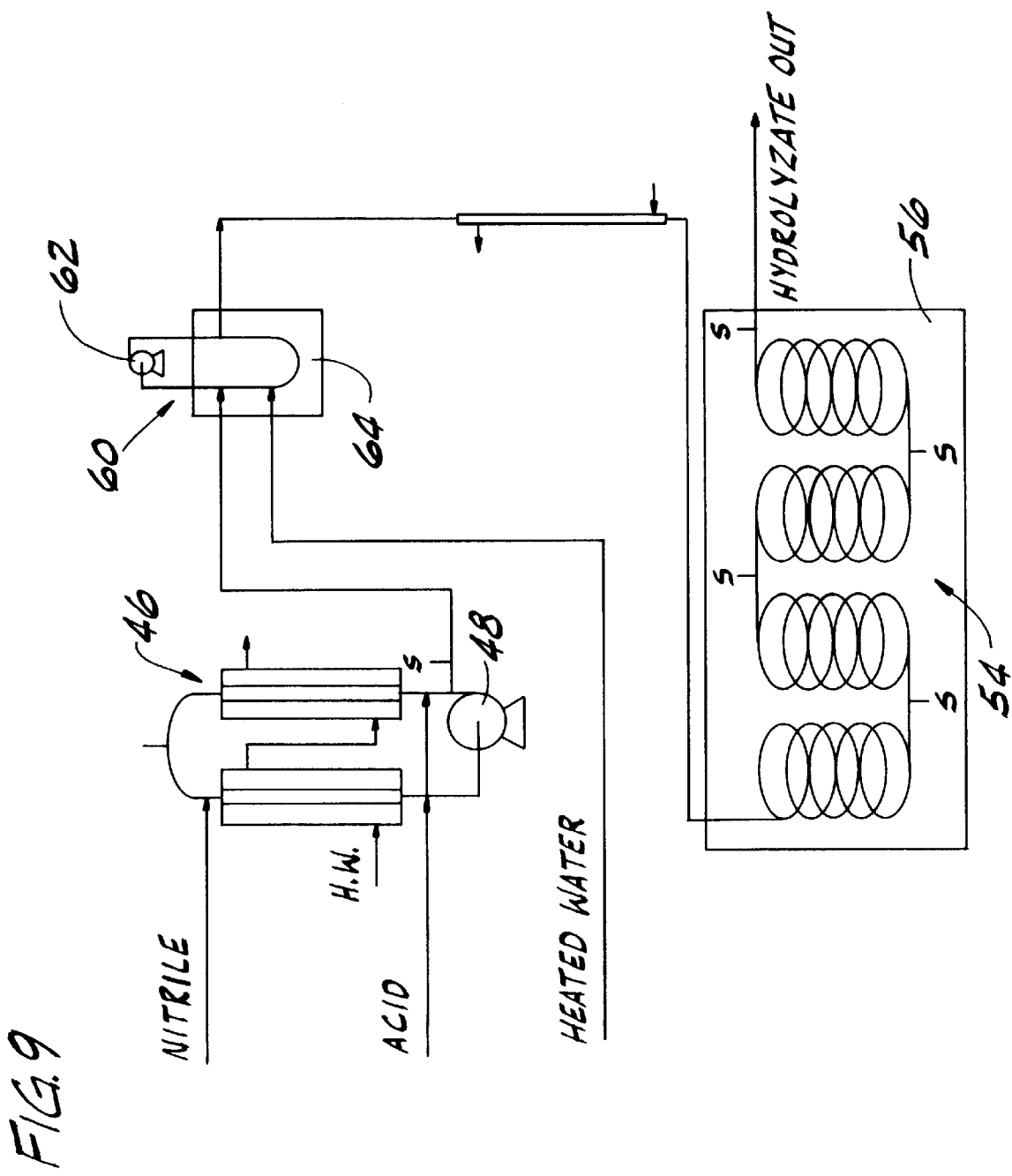
FIG. 9 is a schematic flowsheet of a bench-scale continuous hydrolysis process in which 2-hydroxy-4-methylthiobutanamide exiting a first reactor is introduced into a plug flow reactor and hydrolyzed to produce HMBA.

The bench scale equipment used in the preceding examples was modified by replacing the second recirculating reactor 30 with a small mixing loop 60 with negligible volume used for mixing the water feed and the hydrolysis mixture leaving the first loop reactor 46. The finishing reaction stream was recirculated through the mixing loop by a pump 62. The mixer loop 60 was heated in a hot water bath 64 in order to heat the finishing reaction stream before it entered the PFR in which the amide hydrolysis reaction occurred. The modified bench scale equipment is shown in FIG. 9.

Nitrile at 0.73 g/min was fed to the first recirculating reactor, along with 0.83 g/min 65% sulfuric acid, giving a 0.99 acid/nitrile molar ratio. Tile temperature in the reactor loop was 60° C. and the residence time was estimated as 36.8 minutes. Analysis of the reactor outlet sample revealed that nitrile was essentially hydrolyzed to amide with less than 0.1% unreacted nitrile remaining in the outlet stream. The temperature of the hydrolysis mixture at the outlet of the mixer loop was 75° C. and the residence time in the mixer loop was 1.5 minutes. The PFR coils were maintained at 100 to 101° C. The residence time in each of the first three coils was 16 minutes and that in the last coil was 15.2 minutes. Amide hydrolysis was completed in the last PFR coil.

EXAMPLE 22

The equipment used in the continuous hydrolysis process as shown in FIG. 3 consists of two CSTRs and one packed column type PFR. The first CSTR was devoted for the nitrile hydrolysis while the second CSTR and PFR were for the amide hydrolysis. The PFR is an 8 inch diameter teflon lined carbon steel pipe packed with Koch SMVP Teflon packing. The PFR was manufactured by Koch Engineering. The threshold velocity for the SMVP packing is 0.95 mm/sec.

105 lbs/hr of nitrile and 121 lbs/hr of 659 sulfuric acid were continuously fed to the first 20 gallon CSTR in which 13 gallons of liquid were maintained by a level controller controlling the reactor outlet flow. The reactor was maintained at 65° C. by an external cooler in a product recirculating loop. The residence time based on the total feed rate and the reactor liquid volume was 38 minutes. The outlet hydrolyzate sample, based on a gas chromatographic analysis, was found to contain less than 0.1% nitrile, 34.9% amide, and 11.2% HMBA. The outlet stream was introduced to the second 30 gallon CSTR having a liquid volume of 27.7 gallons. An 80° C. hot water stream was also fed to the second CSTR at a rate of 60.5 lbs/hr. The reactor temperature was 105° C. and the residence time was 91 minutes. The hydrolyzate from the reactor contained 1.9% amide, indicating that more than 90% of incoming amide was converted to HMBA in this vessel. The second CSTR outlet stream then entered the packed column reactor containing structure packing and having a total liquid volume of 25 gallons. From the various samples obtained along the length of the column reactor, the amide hydrolysis reaction was found to have approached completion at 70% of the length of the reactor. The temperature profile of the adiabatic column reactor ranged from 100 to 102° C. and the residence time in the PFR was 52.9 minutes. The final product contained less than 0.1% nitrile, less than 0.1% amide, and 48% HMBA. The major by-product of the hydrolysis process, ammonium bisulfate, can be separated from the product by conventional means.

EXAMPLE 23

The equipment as used in Example 22 was used for the following hydrolysis process except that the second CSTR was bypassed such that the packed column reactor was the sole reactor for the amide hydrolysis reaction.

The feed rates to the first CSTR were as described in Example 22. However, the temperature in the first CSTR was 60° C. Analysis of the outlet sample revealed that the intermediate hydrolysis mixture contained 0.2% nitrile, 39.46 amide, and 9.5% HMBA. The lower CSTR operating temperature resulted in a slightly higher nitrile concentration but a lower HMBA concentration. The intermediate hydrolysis mixture was mixed with a hot water stream (60.5 lbs/hr) in an in-line static mixer. The finishing reaction stream entered the PFR that maintained a steady state temperature profile from 80° C. at the inlet, reaching a peak temperature of 105° C. at the middle and dropping to 102° C. at the outlet of the packed column. Although the column walls were heat traced and insulated, some heat losses were encountered. The residence time in the column reactor was 52.9 minutes. The final hydrolyzate at the outlet of the column reactor contained less than 0.1% nitrile, 0.1% amide and 40.8% HMBA, the balance being by-product ammonium bisulfate and water.

EXAMPLE 24

The equipment as utilized in Example 23 was used in the following hydrolysis except that concentrated sulfuric acid was fed directly to the first CSTR (FIG. 5) without predilution to 65% sulfuric acid with water. A water stream was also fed to the reactor. Thus, both the heat of dilution of the acid and the heat of hydrolysis were removed via the external circulating cooler. The second CSTR was by-passed.

Nitrile (72 lbs/hr), 96% sulfuric acid (56.2 lbs/hr) and dilution water (26.7 lbs/hr) were simultaneously fed to the first CSTR where nitrile hydrolysis was occurring. The operating liquid volume was 10 gallons, which provided 42.5 minutes of residence time based on the total sum of the three feed rates. The reaction temperature was controlled at 55° C. The gas chromatographic analysis of the aqueous hydrolysis mixture showed that it contained 0.5% nitrile, 40.6% amide, and 5.7% HMBA. The aqueous hydrolysis mixture was mixed with 41.3 lbs/hr hot water in the in-line static mixer. The finishing reaction stream entered the packed column reactor in the same fashion as described in Example 23, except that the adiabatic reaction temperatures in the column reactor were slightly higher, probably due to additional heat release from the higher unreacted nitrile content leaving the CSTR that was operated at a lower temperature. From the samples withdrawn from the column reactor, the amide hydrolysis was determined to have been completed at 70% of the column height from the bottom inlet.

EXAMPLES 25–38

Hydrolysis mixture samples were taken at the outlet of each CSTR, the PFR inlet (S1), the PFR outlet (S6), and at four sampling ports along the length of the PFR (S2 through S5) as shown in FIG. 3. The samples were removed during steady state conditions and were analyzed by a gas chromatographic method to determine the hydrolysis mixture composition when leaving the CSTRs and when flowing through the PFR. The hydrolysis mixture composition and the temperature and residence time in each CSTR and within each section of the PFR are shown below. The remainder of the hydrolysis mixture included water and ammonium bisulfate. Examples that do not indicate CSTR-II data involved equipment wherein the second CSTR was bypassed such that a diluted aqueous hydrolysis mixture flowed from the in-line mixer directly to the PFR.

The data demonstrate that conversion is affected by temperature, acid/nitrile ratio and the degree of axial back mixing in the plug flow reactor. Back mixing is in turn a function of the velocity at which the reacting mixture flows through the reactor. In the instances in which back mixing affected conversion, the reactor was operated at less than its threshold velocity of 1.0 mm/sec., resulting in a lower average driving force, i.e., amide concentration integrated along the length of the reactor, for this non-zero order reaction. In some instances, it was possible to compensate for operation below threshold velocity using relatively higher temperature and/or acid/nitrile ratio. Further discussion of the relationship of velocity to axial back mixing and the resultant effect on conversion is set forth at the end of Example 38.

EXAMPLE 25

Nitrile at 105.00 lbs/hr was fed to the first CSTR, along with 120.95 lbs/hr 65% sulfuric acid, giving a 1.03 acid/nitrile molar ratio. A water feed at 60.50 lbs/hr was also introduced into the second CSTR. The hydrolysis mixture composition for each sample and the temperature for each location are shown in Table 20 below.

TABLE 20

|  | CSTR-I | CSTR-II | S1 | S2 | S3 | S4 | S5 | S6 |
|---|---|---|---|---|---|---|---|---|
| Volume (gal) | 13 | 27.7 | | | 17.5 (total PFR) | | | |
| Temperature (° C.) | 65 | 104 | 101 | 103 | 102 | 103 | 103 | 102 |
| PFR Velocity = 1.0 mm/sec. | | | | | | | | |
| Hydrolysis Mixture Composition (wt. %) | | | | | | | | |
| Nitrile | 0.02 | 0.02 | 0.01 | 0.01 | 0.01 | trace | trace | trace |
| HMBA | 12 | 41 | 34 | 39 | 39 | 39 | 41 | 40 |
| Amide | 34 | 2.0 | 0.5 | 0.27 | 0.04 | 0.02 | 0.02 | 0.02 |
| Hydrolyzate Product Color: 11–12 on Gardner scale | | | | | | | | |

EXAMPLE 26

Nitrile at 105.00 lbs/hr was fed to the first CSTR, along with 120.95 lbs/hr 65% sulfuric acid, giving a 1.00 acid/nitrile molar ratio. A water feed at 60.50 lbs/hr was also introduced into the second CSTR. The hydrolysis mixture composition for each sample and the temperature for each location are shown in Table 21 below.

TABLE 21

|  | CSTR-I | CSTR-II | S1 | S2 | S3 | S4 | S5 | S6 |
|---|---|---|---|---|---|---|---|---|
| Volume (gal) | 13 | 27.7 | | | 17.5 (total PFR) | | | |
| Temperature (° C.) | 65 | 105 | 101 | 102 | 102 | 102 | 102 | 101 |
| PFR Velocity = 1.0 mm/sec. | | | | | | | | |
| Hydrolysis Mixture Composition (wt. %) | | | | | | | | |
| Nitrile | 0.01 | trace | trace | trace | trace | trace | trace | 0.01 |
| HMBA | 11 | 36 | 37 | 29 | 26 | 30 | 31 | 47 |
| Amide | 35 | 1.9 | 1.1 | 0.21 | 0.05 | 0.05 | 0.05 | 0.05 |
| Hydrolyzate Product Color: 6–7 on Gardner scale | | | | | | | | |

EXAMPLE 27

Nitrile at 105.00 lbs/hr was fed to the first CSTR, along with 145.14 lbs/hr 65% sulfuric acid, giving a 1.21 acid/nitrile molar ratio. A water feed at 57.4 lbs/hr was also introduced into the second CSTR. The hydrolysis mixture composition for each sample and the temperature for each location are shown in Table 22 below.

TABLE 22

|  | CSTR-I | CSTR-II | S1 | S2 | S3 | S4 | S5 | S6 |
|---|---|---|---|---|---|---|---|---|
| Volume (gal) | 13 | 27.7 | | | 17.5 (total PFR) | | | |
| Temperature (° C.) | 65 | 93 | 90 | 93 | 92 | 92 | 92 | 91 |
| PFR Velocity = 1.0 mm/sec. | | | | | | | | |
| Hydrolysis Mixture Composition (wt. %) | | | | | | | | |
| Nitrile | trace | trace | trace | trace | trace | trace | trace | trace |
| HMBA | 11 | 33 | 34 | 35 | 36 | 36 | 38 | 33 |
| Amide | 31 | 1.8 | 1.3 | 0.14 | 0.02 | 0.01 | 0.01 | 0.01 |
| Hydrolyzate Product Color: 9–10 on Gardner scale | | | | | | | | |

EXMAPLE 28

Nitrile at 72.00 lbs/hr was fed to the first CSTR, along with 82.94 lbs/hr 65% sulfuric acid, giving a 1.0 acid/nitrile molar ratio. A water feed at 41.30 lbs/hr was also introduced into the second CSTR. The hydrolysis mixture composition for each sample and the temperature for each location are shown in Table 23 below.

TABLE 23

|  | CSTR-I | S1 | S2 | S3 | S4 | S5 | S6 |
|---|---|---|---|---|---|---|---|
| Volume (gal) | 10 | | | 19.9 (total PFR) | | | |
| Temperature (° C.) | 65 | 80 | 96 | 97 | 97 | 97 | 97 |
| PFR Velocity = 0.69 mm/sec. | | | | | | | |
| Hydrolysis Mixture Composition (wt. %) | | | | | | | |
| Nitrile | 0.13 | 0.03 | 0.02 | 0.01 | 0.01 | 0.01 | 0.02 |
| HMBA | 14 | 22 | 28 | 24 | 27 | 25 | 44 |
| Amide | 40 | 19 | 3.3 | 1.6 | 1.7 | 1.4 | 1.2 |
| Hydrolyzate Product Color: 3 on Gardner scale | | | | | | | |

EXAMPLE 29

Nitrile at 72.00 lbs/hr was fed to the first CSTR, along with 82.94 lbs/hr 65% sulfuric acid, giving a 1.0 acid/nitrile molar ratio. A water feed at 41.30 lbs/hr was also introduced into the second CSTR. The hydrolysis mixture composition for each sample and the temperature for each location are shown in Table 24 below.

TABLE 24

|  | CSTR-I | S1 | S2 | S3 | S4 | S5 | S6 |
|---|---|---|---|---|---|---|---|
| Volume (gal) | 10 | | | 19.9 (total PFR) | | | |
| Temperature (° C.) | 60 | 81 | 103 | 103 | 101 | 101 | 100 |
| PFR Velocity = 0.69 mm/sec | | | | | | | |
| Hydrolysis Mixture Composition (wt. %) | | | | | | | |
| Nitrile | 0.19 | 0.01 | trace | trace | trace | trace | trace |
| HMBA | 8.8 | 20 | 38 | 37 | 39 | 47 | 54 |
| Amide | 38 | 22 | 1.4 | 0.59 | 0.34 | 0.33 | 0.06 |
| Hydrolyzate Product Color: 6–7 on Gardner scale | | | | | | | |

EXAMPLE 30

Nitrile at 150.00 lbs/hr was fed to the first CSTR, along with 172.79 lbs/hr 65% sulfuric acid, giving a 1.04 acid/nitrile molar ratio. A water feed at 86.40 lbs/hr was also introduced into the second CSTR. The hydrolysis mixture composition for each sample and the temperature for each location are shown in Table 25 below.

TABLE 25

|  | CSTR-I | CSTR-II | S1 | S2 | S3 | S4 | S5 | S6 |
|---|---|---|---|---|---|---|---|---|
| Volume (gal) | 10 | 27.7 | | | 25.0 (total PFR) | | | |
| Temperature (° C.) | 65 | 104 | 100 | 102 | 102 | 102 | 102 | 101 |
| PFR Velocity = 1.4 mm/sec. | | | | | | | | |
| Hydrolysis Mixture Composition (wt. %) | | | | | | | | |
| Nitrile | 0.26 | 0.03 | 0.01 | trace | trace | trace | trace | trace |
| HMBA | 8.1 | 35 | 37 | 39 | 37 | 37 | 39 | 38 |
| Amide | 38 | 3.0 | 1.5 | 0.21 | 0.03 | 0.02 | 0.02 | 0.02 |
| Hydrolyzate Product Color: 10–11 on Gardner scale | | | | | | | | |

EXAMPLE 31

Nitrile at 150.00 lbs/hr was fed to the first CSTR, along with 172.79 lbs/hr 65% sulfuric acid, giving a 1.02 acid/nitrile molar ratio. A water feed at 86.40 lbs/hr was also introduced into the second CSTR. The hydrolysis mixture composition for each sample and the temperature for each location are shown in Table 26 below.

TABLE 26

|  | CSTR-I | CSTR-II | S1 | S2 | S3 | S4 | S5 | S6 |
|---|---|---|---|---|---|---|---|---|
| Volume (gal) | 10 | 27.7 | | | 25.0 (total PFR) | | | |
| Temperature (° C.) | 65 | 102 | 100 | 103 | 103 | 104 | 103 | 102 |
| PFR Velocity = 1.4 mm/sec. | | | | | | | | |
| Hydrolysis Mixture Composition (wt. %) | | | | | | | | |
| Nitrile | 0.13 | 0.01 | 0.03 | 0.03 | 0.02 | 0.02 | 0.02 | 0.01 |
| HMBA | 7.0 | 36 | 37 | 39 | 39 | 40 | 41 | 40 |
| Amide | 40 | 3.2 | 2.4 | 0.84 | 0.23 | 0.18 | 0.16 | 0.13 |
| Hydrolyzate Product Color: 8–9 on Gardner scale | | | | | | | | |

EXAMPLE 32

Nitrile at 105.00 lbs/hr was fed to the first CSTR, along with 120.95 lbs/hr 65% sulfuric acid, giving a 1.02 acid/nitrile molar ratio. A water feed at 60.50 lbs/hr was also introduced into the second CSTR. The hydrolysis mixture composition for each sample and the temperature for each location are shown in Table 27 below.

TABLE 27

|  | CSTR-I | CSTR-II | S1 | S2 | S3 | S4 | S5 | S6 |
|---|---|---|---|---|---|---|---|---|
| Volume (gal) | 10 | 27.7 | | | 17.5 (total PFR) | | | |
| Temperature (° C.) | 63 | 105 | 101 | 103 | 103 | 103 | 103 | 101 |
| PFR Velocity = 1.0 mm/sec. | | | | | | | | |
| Hydrolysis Mixture Composition (wt. %) | | | | | | | | |
| Nitrile | 0.36 | 0.03 | 0.01 | 0.01 | 0.01 | trace | trace | trace |
| HMBA | 9.1 | 38 | 38 | 40 | 40 | 41 | 39 | 40 |
| Amide | 39 | 2.7 | 1.8 | 0.32 | 0.08 | 0.05 | 0.05 | 0.03 |
| Hydrolyzate Product Color: 10–11 on Gardner scale | | | | | | | | |

EXAMPLE 33

Nitrile at 72.00 lbs/hr was fed to the first CSTR, along with 82.94 lbs/hr 65% sulfuric acid, giving a 1.0 acid/nitrile molar ratio. A water feed at 41.30 lbs/hr was also introduced into the second CSTR. The hydrolysis mixture composition for each sample and the temperature for each location are shown in Table 28 below.

TABLE 28

|  | CSTR-I | S1 | S2 | S3 | S4 | S5 | S6 |
|---|---|---|---|---|---|---|---|
| Volume (gal) | 10 | | | 19.9 (total PFR) | | | |
| Temperature (° C.) | 60 | 84 | 103 | 105 | 105 | 105 | 103 |
| PFR Velocity = 0.69 mm/sec. | | | | | | | |
| Hydrolysis Mixture Composition (wt. %) | | | | | | | |
| Nitrile | 0.41 | 0.02 | 0.01 | 0.01 | 0.01 | 0.01 | 0.01 |
| HMBA | 9.5 | 23 | 26 | 23 | 23 | 23 | 47 |
| Amide | 43 | 17 | 2.3 | 0.63 | 0.62 | 0.61 | 0.72 |
| Hydrolyzate Product Color: 5–6 on Gardner scale | | | | | | | |

EXAMPLE 34

Nitrile at 90.60 lbs/hr was fed to the first CSTR, along with 103.80 lbs/hr 65% sulfuric acid, giving a 1.03 acid/nitrile molar ratio. A water feed at 51.90 lbs/hr was also introduced into the second CSTR. The hydrolysis mixture composition for each sample and the temperature for each location are shown in Table 29 below.

TABLE 29

|  | CSTR-I | S1 | S2 | S3 | S4 | S5 | S6 |
|---|---|---|---|---|---|---|---|
| Volume (gal) | 12.6 |  | 25.0 (total PFR) | | | | |
| Temperature (° C.) | 59 | 82 | 104 | 105 | 105 | 105 | 104 |
| PFR Velocity = 0.86 mm/sec. | | | | | | | |
| Hydrolysis Mixture Composition (wt. %) | | | | | | | |
| Nitrile | 0.39 | 0.03 | 0.01 | 0.01 | 0.01 | 0.01 | 0.01 |
| HMBA | 9.1 | 23 | 33 | 30 | 31 | 31 | 38 |
| Amide | 41 | 18 | 2.0 | 0.92 | 0.79 | 0.71 | 0.76 |
| Hydrolyzate Product Color: 8–9 on Gardner scale | | | | | | | |

EXAMPLE 35

Nitrile at 90.60 lbs/hr was fed to the first CSTR, along with 124.80 lbs/hr 65% sulfuric acid, giving a 1.20 acid/nitrile molar ratio. A water feed at 49.40 lbs/hr was also introduced into the second CSTR. The hydrolysis mixture composition for each sample and the temperature for each location are shown in Table 30 below.

TABLE 30

|  | CSTR-I | S1 | S2 | S3 | S4 | S5 | S6 |
|---|---|---|---|---|---|---|---|
| Volume (gal) | 12.6 |  | 25.0 (total PFR) | | | | |
| Temperature (° C.) | 45 | 86 | 107 | 107 | 107 | 107 | 105 |
| PFR Velocity = 0.86 mm/sec. | | | | | | | |
| Hydrolysis Mixture Composition (wt. %) | | | | | | | |
| Nitrile | 0.07 | 0.01 | trace | trace | trace | trace | trace |
| HMBA | 8.1 | 23 | 35 | 33 | 39 | 37 | 37 |
| Amide | 36 | 12 | 1.0 | trace | trace | trace | 0.01 |

Hydrolyzate Product Color: 11–12 on Gardner scale

EXAMPLE 36

Nitrile at 90.60 lbs/hr was fed to the first CSTR, along with 124.80 lbs/hr 65% sulfuric acid, giving a 1.20 acid/nitrile molar ratio. A water feed at 49.40 lbs/hr was also introduced into the second CSTR. The hydrolysis mixture composition for each sample and the temperature for each location are shown in Table 31 below.

TABLE 31

|  | CSTR-I | S1 | S2 | S3 | S4 | S5 | S6 |
|---|---|---|---|---|---|---|---|
| Volume (gal) | 12.6 |  | 25.0 (total PFR) | | | | |
| Temperature (° C.) | 58 | 82 | 105 | 103 | 103 | 103 | 101 |
| PFR Velocity = 0.86 mm/sec. | | | | | | | |
| Hydrolysis Mixture Composition (wt. %) | | | | | | | |
| Nitrile | trace | trace | trace | trace | trace | trace | trace |
| HMBA | 8.3 | 20 | 38 | 37 | 38 | 38 | 39 |
| Amide | 31 | 18 | 0.96 | trace | trace | trace | trace |

Hydrolyzate Product Color: 11–12 on Gardner scale

EXAMPLE 37

Nitrile at 90.60 lbs/hr was fed to the first CSTR, along with 103.80 lbs/hr 65% sulfuric acid, giving a 1.0 acid/nitrile molar ratio. A water feed at 51.90 lbs/hr was also introduced into the second CSTR. The hydrolysis mixture composition for each sample and the temperature for each location are shown in Table 32 below.

TABLE 32

|  | CSTR-I | S1 | S2 | S3 | S4 | S5 | S6 |
|---|---|---|---|---|---|---|---|
| Volume (gal) | 12.6 |  | 25.0 (total PFR) | | | | |
| Temperature (° C.) | 59 | 88 | 109 | 109 | 109 | 109 | 107 |
| PFR Velocity = 0.86 mm/sec. | | | | | | | |
| Hydrolysis Mixture Composition (wt. %) | | | | | | | |
| Nitrile | 0.09 | 0.01 | trace | 0.01 | trace | trace | 0.01 |
| HMBA | 8.8 | 26 | 38 | 69 | 38 | 40 | 41 |
| Amide | 37 | 13 | 0.30 | 0.02 | 0.01 | 0.01 | trace |

Hydrolyzate Product Color: 11–12 on Gardner scale

EXAMPLE 38

Nitrile at 105.00 lbs/hr was fed to the first CSTR, along with 120.95 lbs/hr 65% sulfuric acid, giving a 1.0 acid/nitrile molar ratio. A water feed at 60.50 lbs/hr was also introduced into the second CSTR. The hydrolysis mixture composition for each sample and the temperature for each location are shown in Table 33 below.

TABLE 33

|  | CSTR-I | S1 | S2 | S3 | S4 | S5 | S6 |
|---|---|---|---|---|---|---|---|
| Volume (gal) | 14.6 |  | 25.0 | (total PFR) | | | |
| Temperature (° C.) | 60 | 80 | 103 | 104 | 105 | 104 | 102 |
| Hydrolysis Mixture Composition (wt. %) | | | | | | | |
| Nitrile | 0.22 | 0.02 | 0.01 | 0.01 | 0.01 | 0.01 | 0.01 |
| HMBA | 9.5 | 24 | 39 | 45 | 45 | 42 | 41 |

TABLE 33-continued

|  | CSTR-I | S1 | S2 | S3 | S4 | S5 | S6 |
|---|---|---|---|---|---|---|---|
| Amide | 39 | 21 | 2.5 | 0.19 | 0.20 | 0.28 | 0.11 |

PFR Velocity = 1.0 mm/sec.
Hydrolyzate Product Color: 8–9 on Gardner scale

As noted above, certain of the conversions obtained in a packed column PFR were not sufficient to meet target residual amide concentrations in the product hydrolyzate. These lower conversions were attributable to lower reaction temperature or acid/nitrile ratio, excessive axial back mixing, or some combination of these factors. Based on studies conducted on reactors operated at velocity adequate to provide a Peclet number greater than about 50, it was determined that residual amide concentration in the hydrolyzate could be consistently reduced to less than about 0.03% at reaction temperatures and acid/nitrile ratios in the preferred ranges discussed above for steady state operations. But where the Peclet number was significantly below 50, lower conversions were generally found unless temperature and/or acid/nitrile ratio were increased to compensate.

To investigate the effect of velocity on back-mixing in a packed column PFR, residence time distribution tests were conducted at varying velocities using a pulse of salt as a tracer injected at the bottom of a column in which tap water was caused to flow upwardly. At the top outlet of the reactor a conductivity probe was inserted for measuring the conductivity of the outlet flow, from which tracer response data, in terms of salt (NaCl) concentration vs. time, were obtained. Following conventional methods, calculations based on the response data were made to determine the mean residence time (the first moment of distribution), the variance (the second moment of distribution), the Peclet number, and the equivalent number of stirred tanks in series. For the reactor tested, the flow rate (gpm), mean residence time (θ), dimensionless variance ($\sigma^2$), Peclet number (Pe), and number of equivalent stirred tank reactors (j), are set forth in Table 34.

TABLE 34

| gpm | θ | $\sigma^2$ | Pe | j |
|---|---|---|---|---|
| 0.95 | 29.5 | 0.0393 | 50.9 | 25.5 |
| 0.47 | 66.3 | 0.0681 | 29.4 | 14.7 |
| 0.90 | 25.1 | 0.0749 | 26.7 | 13.4* |

*Based on injection of tracer at a port spaced above the bottom of the reactor. Adjusted for this factor, j = 20.5 and Pe = 41.

These data demonstrate a critical velocity threshold in the range of 0.5 gpm for the packed column that was used in these tests.

Based on kinetic calculations on the amide hydrolysis reaction, the relationship between the number of equivalent stirred tank reactors and the residual amide concentration was calculated. Computations were also made of the correlation between the number of equivalent stirred tank reactors and: (a) the ratio of (requisite reactor length for a given degree of conversion) to (requisite length for the same degree of conversion under perfect plug flow conditions) ($L/L_p$); and (b) the ratio between (residual amide concentration for a given length of reactor) vs. (residual amide concentration for the same length reactor under perfect plug flow conditions) ($C/C_p$). These calculations are set forth in Table 35.

TABLE 35

| j | $L/L_p$ | $C/C_p$ | C(% amide out) |
|---|---|---|---|
| 15 | 1.236 | 2.66 | 0.0581% |
| 20 | 1.177 | 2.25 | 0.0491 |
| 25 | 1.141 | 2.00 | 0.0436 |
| 30 | 1.178 | 1.83 | 0.0399 |
| 40 | 1.088 | 1.62 | 0.0353 |
| ∞ | 1.000 | 1.00 | 0.0218 |

EXAMPLES 39–55

Hydrolysis mixture samples were removed during steady state conditions and were analyzed by a gas chromatographic method to determine the hydrolysis mixture composition when leaving the CSTR, entering the PFR and leaving the PFR as shown in FIG. 2 for Examples 39–48 and as shown in FIG. 1 for Examples 49–55.

The data demonstrate that conversion of HMBN to amide is improved by an additional residence time of about 3 minutes within the zone between the outlet of the CSTR and the point of dilution before transfer of the stream to the PFR. Examples 44 and 51 are directly comparable, as are Examples 45, 46 and 53 because they were run at the same flow rate and exhibited the same peak temperature in the PFR. Examples 39–48 demonstrate the hydrolyzate color improvement as flow reactor peak temperature was reduced from 105 or 106° C. to 101 or 102° C.

EXAMPLE 39

Nitrile, 96% sulfuric acid and water were fed to a CSTR as shown in FIG. 2 giving a 1.0 acid/nitrile molar ratio to form an aqueous hydrolysis mixture. After a residence time of 37 minutes in the CSTR at 60° C., the hydrolysis mixture contained 0.03% nitrile and 39% amide by weight. The residence time of the aqueous hydrolysis mixture in the circulation zone upstream of the forward flow port and in the forward flow reaction zone between the forward flow port and the point of dilution was 4 seconds and 3 minutes, respectively. After dilution, the finishing reaction stream was fed to the PFR which operated adiabatically at 81–106° C. and a residence time of 70 minutes. The finished aqueous hydrolyzate product contained 0.01% amide and less than 0.01% nitrile. The finished aqueous hydrolyzate product color was 8.5 on a Gardner scale.

EXAMPLE 40

Nitrile, 96% sulfuric acid and water were fed to a CSTR as shown in FIG. 2 giving a 1.0 acid/nitrile molar ratio to form an aqueous hydrolysis mixture. After a residence time of 37 minutes in the CSTR at 60° C., the hydrolysis mixture contained 0.01% nitrile and 38% amide by weight. The residence time of the aqueous hydrolysis mixture in the circulation zone upstream of the forward flow port and in the forward flow reaction zone between the forward flow port and the point of dilution was 4 seconds and 3 minutes, respectively. After dilution, the finishing reaction stream was fed to the PFR which operated adiabatically at 81–105° C.

and a residence time of 70 minutes. The finished aqueous hydrolyzate product contained 0.01% amide and less than 0.01% nitrile. The finished aqueous hydrolyzate product color was 8.5 on a Gardner scale.

EXAMPLE 41

Nitrile, 96% sulfuric acid and water were fed to a CSTR as shown in FIG. 2 giving a 1.0 acid/nitrile molar ratio to form an aqueous hydrolysis mixture. After a residence time of 37 minutes in the CSTR at 60° C., the hydrolysis mixture contained 0.08% nitrile and 38% amide by weight. The residence time of the aqueous hydrolysis mixture in the circulation zone upstream of the forward flow port and in the forward flow reaction zone between the forward flow port and the point of dilution was 4 seconds and 3 minutes, respectively. After dilution, the finishing reaction stream was fed to the PFR which operated adiabatically at 80–105° C. and a residence time of 70 minutes. The finished aqueous hydrolyzate product contained less than 0.01% amide and nitrile. The finished aqueous hydrolyzate product color was 8.5 on a Gardner scale.

EXAMPLE 42

Nitrile, 96% sulfuric acid and water were fed to a CSTR as shown in FIG. 2 giving a 1.0 acid/nitrile molar ratio to form an aqueous hydrolysis mixture. After a residence time of 37 minutes in the CSTR at 60° C., the hydrolysis mixture contained 0.08% nitrile and 38% amide by weight. The residence time of the aqueous hydrolysis mixture in the circulation zone upstream of the forward flow port and in the forward flow reaction zone between the forward flow port and the point of dilution was 4 seconds and 3 minutes, respectively. After dilution, the finishing reaction stream was fed to the PFR which operated adiabatically at 80–105° C. and a residence time of 70 minutes. The finished aqueous hydrolyzate product contained less than 0.01% amide and nitrile. The finished aqueous hydrolyzate product color was 7.5 on a Gardner scale.

EXAMPLE 43

Nitrile, 96% sulfuric acid and water were fed to a CSTR as shown in FIG. 2 giving a 1.0 acid/nitrile molar ratio to form an aqueous hydrolysis mixture. After a residence time of 37 minutes in the CSTR at 60° C., the hydrolysis mixture was not analyzed. The residence time of the aqueous hydrolysis mixture in the circulation zone upstream of the forward flow port and in the forward flow reaction zone between the forward flow port and the point of dilution was 4 seconds and 3 minutes, respectively. After dilution, the finishing reaction stream was fed to the PFR which operated adiabatically at 79–104° C. and a residence time of 70 minutes. The finished aqueous hydrolyzate product contained 0.01% amide and less than 0.01% nitrile. The finished aqueous hydrolyzate product color was 8.5 on a Gardner scale.

EXAMPLE 44

Nitrile, 96% sulfuric acid and water were fed to a CSTR as shown in FIG. 2 giving a 1.0 acid/nitrile molar ratio to form an aqueous hydrolysis mixture. After a residence time of 37 minutes in the CSTR at 60° C., the hydrolysis mixture was not analyzed. The residence time of the aqueous hydrolysis mixture in the circulation zone upstream of the forward flow port and in the forward flow reaction zone between the forward flow port and the point of dilution was 4 seconds and 3 minutes, respectively. After dilution, the finishing reaction stream was fed to the PFR which operated adiabatically at 79–104° C. and a residence time of 70 minutes. The finished aqueous hydrolyzate product contained less than 0.01% amide and nitrile. The finished aqueous hydrolyzate product color was 8.5 on a Gardner scale.

EXAMPLE 45

Nitrile, 96% sulfuric acid and water were fed to a CSTR as shown in FIG. 2 giving a 1.0 acid/nitrile molar ratio to form an aqueous hydrolysis mixture. After a residence time of 37 minutes in the CSTR at 60° C., the hydrolysis mixture contained 0.04% nitrile and 40% amide by weight. The residence time of the aqueous hydrolysis mixture in the circulation zone upstream of the forward flow port and in the forward flow reaction zone between the forward flow port and the point of dilution was 4 seconds and 3 minutes, respectively. After dilution, the finishing reaction stream was fed to the PFR which operated adiabatically at 77–102° C. and a residence time of 70 minutes. The finished aqueous hydrolyzate product contained 0.0% amide and less than 0.0% nitrile. The finished aqueous hydrolyzate product color was 8.5 on a Gardner scale.

EXAMPLE 46

Nitrile, 96% sulfuric acid and water were fed to a CSTR as shown in FIG. 2 giving a 1.0 acid/nitrile molar ratio to form an aqueous hydrolysis mixture. After a residence time of 37 minutes in the CSTR at 60° C., the hydrolysis mixture contained 0.03t nitrile and 40% amide by weight. The residence time of the aqueous hydrolysis mixture in the circulation zone upstream of the forward flow port and in the forward flow reaction zone between the forward flow port and the point of dilution was 4 seconds and 3 minutes, respectively. After dilution, the finishing reaction stream was fed to the PFR which operated adiabatically at 77–102° C. and a residence time of 70 minutes. The finished aqueous hydrolyzate product contained 0.01% amide and less than 0.01% nitrile. The finished aqueous hydrolyzate product color was 7.5 on a Gardner scale.

EXAMPLE 47

Nitrile, 96% sulfuric: acid and water were fed to a CSTR as shown in FIG. 2 giving a 1.0 acid/nitrile molar ratio to form an aqueous hydrolysis mixture. After a residence time of 37 minutes in the CSTR at 60° C., the hydrolysis mixture contained 0.06% nitrile and 37% amide by weight. The residence time of the aqueous hydrolysis mixture in the circulation zone upstream of the forward flow port and in the forward flow reaction zone between the forward flow port and the point of dilution was 4 seconds and 3 minutes, respectively. After dilution, the finishing reaction stream was fed to the PFR which operated adiabatically at 75–101° C. and a residence time of 70 minutes. The finished aqueous hydrolyzate product contained 0.01% amide and less than 0.01% nitrile. The finished aqueous hydrolyzate product color was 6.5 on a Gardner scale.

EXAMPLE 48

Nitrile, 96% sulfuric acid and water were fed to a CSTR as shown in FIG. 2 giving a 1.0 acid/nitrile molar ratio to form an aqueous hydrolysis mixture. After a residence time of 37 minutes in the CSTR at 60° C., the hydrolysis mixture contained 41% amide by weight and less than 0.09% nitrile. The residence time of the aqueous hydrolysis mixture in the circulation zone upstream of the forward flow port and in the forward flow reaction zone between the forward flow port and the point of dilution was 4 seconds and 3 minutes, respectively. After dilution, the finishing reaction stream was fed to the PFR which operated adiabatically at 75–101° C.

and a residence time of 70 minutes. The finished aqueous hydrolyzate product contained 0.01% amide and less than 0.01% nitrile. The finished aqueous hydrolyzate product color was 6.5 on a Gardner scale.

EXAMPLE 49

Nitrile, 96% sulfuric acid and water were fed to a CSTR as shown in FIG. 1 giving a 1.0 acid/nitrile molar ratio to form an aqueous hydrolysis mixture. After a residence time of 46 minutes in the CSTR at 62° C., the hydrolysis mixture contained 43% amide and 0.02% nitrile. The residence time of the aqueous hydrolysis mixture in the circulation zone upstream of the forward flow port and in the forward flow reaction zone between the forward flow port and the point of dilution was less than one second and less than one minute, respectively. After dilution, the finishing reaction stream was fed to the PFR which operated adiabatically at 80–104° C. and a residence time of 88 minutes. The finished aqueous hydrolyzate product contained 0.02% nitrile and less than 0.01% amide. The finished aqueous hydrolyzate product color was 8 on a Gardner scale.

EXAMPLE 50

Nitrile, 96% sulfuric acid and water were fed to a CSTR as shown in FIG. 1 giving a 1.0 acid/nitrile molar ratio to form an aqueous hydrolysis mixture. After a residence time of 49 minutes in the CSTR at 62° C., the hydrolysis mixture contained 40% amide and 0.04% nitrile. The residence time of the aqueous hydrolysis mixture in the circulation zone upstream of the forward flow port and in the forward flow reaction zone between the forward flow port and the point of dilution was less than one second and less than one minute, respectively. After dilution, the finishing reaction stream was fed to the PFR which operated adiabatically at 82–104° C. and a residence time of 92 minutes. The finished aqueous hydrolyzate product contained 0.03% nitrile and 0.01% amide. The finished aqueous hydrolyzate product color was 8.5 on a Gardner scale.

EXAMPLE 51

Nitrile, 96% sulfuric acid and water were fed to a CSTR as shown in FIG. 1 giving a 1.0 acid/nitrile molar ratio to form an aqueous hydrolysis mixture. After a residence time of 37 minutes in the CSTR at 62° C., the hydrolysis mixture contained 35% amide and 0.03% nitrile. The residence time of the aqueous hydrolysis mixture in the circulation zone upstream of the forward flow port and in the forward flow reaction zone between the forward flow port and the point of dilution was less than one second and less than one minute, respectively. After dilution, the finishing reaction stream was fed to the PFR which operated adiabatically at 82–106° C. and a residence time of 70 minutes. The finished aqueous hydrolyzate product contained 0.02% nitrile and less than 0.01% amide. The finished aqueous hydrolyzate product color was 8 on a Gardner scale.

EXAMPLE 52

Nitrile, 96% sulfuric acid and water were fed to a CSTR as shown in FIG. 1 giving a 1.0 acid/nitrile molar ratio to form an aqueous hydrolysis mixture. After a residence time of 37 minutes in the CSTR at 61° C., the hydrolysis mixture contained 43% amide and 0.05% nitrile. The residence time of the aqueous hydrolysis mixture in the circulation zone upstream of the forward flow port and in the forward flow reaction zone between the forward flow port and the point of dilution was less than one second and less than one minute, respectively. After dilution, the finishing reaction stream was fed to the PFR which operated adiabatically at 78–103° C. and a residence time of 70 minutes. The finished aqueous hydrolyzate product contained 0.02% amide and the nitrile was not measured. The finished aqueous hydrolyzate product color was 5 on a Gardner scale.

EXAMPLE 53

Nitrile, 96% sulfuric acid and water were fed to a CSTR as shown in FIG. 1 giving a 1.0 acid/nitrile molar ratio to form an aqueous hydrolysis mixture. After a residence time of 37 minutes in the CSTR at 61° C., the hydrolysis mixture contained 40% amide and 0.02% nitrile. The residence time of the aqueous hydrolysis mixture in the circulation zone upstream of the forward flow port and in the forward flow reaction zone between the forward flow port and the point of dilution was less than one second and less than one minute, respectively. After dilution, the finishing reaction stream was fed to the PFR which operated adiabatically at 77–102° C. and a residence time of 70 minutes. The finished aqueous hydrolyzate product contained 0.01% amide and 0.05% nitrile. The finished aqueous hydrolyzate product color was 6 on a Gardner scale.

EXAMPLE 54

Nitrile, 96% sulfuric acid and water were fed to a CSTR as shown in FIG. 1 giving a 1.0 acid/nitrile molar ratio to form an aqueous hydrolysis mixture. After a residence time of 37 minutes in the CSTR at 64° C., the hydrolysis mixture contained 41% amide and 0.02% nitrile. The residence time of the aqueous hydrolysis is mixture in the circulation zone upstream of the forward flow port and in the forward flow reaction zone between the forward flow port and the point of dilution was less than one second and less than one minute, respectively. After dilution, the finishing reaction stream was fed to the PFR which operated adiabatically at 79–103° C. and a residence time of 70 minutes. The finished aqueous hydrolyzate product contained 0.01% amide and 0.03% nitrile. The finished aqueous hydrolyzate product color was not measured.

EXAMPLE 55

Nitrile, 96% sulfuric acid and water were fed to a CSTR as shown in FIG. 1 giving a 1.0 acid/nitrile molar ratio to form an aqueous hydrolysis mixture. After a residence time of 37 minutes in the CSTR at 64° C., the hydrolysis mixture contained 40% amide and 0.01% nitrile. The residence time of the aqueous hydrolysis mixture in the circulation zone upstream of the forward flow port and in the forward flow reaction zone between the forward flow port and the point of dilution was less than one second and less than one minute, respectively. After dilution, the finishing reaction stream was fed to the PFR which operated adiabatically at 79–103° C. and a residence time of 70 minutes. The finished aqueous hydrolyzate product contained 0.01w amide and 0.04% nitrile. The finished aqueous hydrolyzate product color was 9 on a Gardner scale.

EXAMPLE 56

Performance of a continuous hydrolysis system was computer simulated based upon laboratory batch hydrolysis data. 36% hydrochloric acid and nitrile are fed continuously to a CSTR giving a 1.15 acid/nitrile molar ratio to form an aqueous hydrolysis mixture. After a residence time of 60 minutes in the CSTR at 50° C., the hydrolysis mixture contains 46% amide and 0.1% nitrile. The nitrile hydrolysis reactor product stream exiting the CSTR is transferred to an amide hydrolysis cascade tower type reactor that is agitated to enhance fluid mixing and suspend ammonium chloride solids in each of the cascaded compartments. A reactor temperature of 80° C. is provided by jackets surrounding the reactor shell or by passing the stream through an external feed preheater. The residence time of the stream in the amide hydrolysis reactor is 4 hours. The finished aqueous hydrolyzate product contains 0.04% amide and 0.04% nitrile.

EXAMPLE 57

Performance of a continuous hydrolysis system was computer simulated based upon laboratory batch hydrolysis data. 36% hydrochloric acid and nitrile are fed continuously to a CSTR giving a 1.15 acid/nitrile molar ratio to form an aqueous hydrolysis mixture. After a residence time of 60 minutes in the CSTR at 50° C., the hydrolysis mixture contains 46% amide and 0.1% nitrile. The nitrile hydrolysis reactor product stream exiting the CSTR is transferred to a second CSTR for completion of 80–90% of the amide hydrolysis. After a residence time of 4 hours in the second CSTR, the amide hydrolysis slurry containing ammonium chloride is cooled to 50° C. and the ammonium chloride is removed by centrifuge. The mother liquor from the centrifuge is transferred to a plug flow reactor operated at 80° C. by use of jacketing or an external preheater. The PFR is not agitated because the ammonium chloride is dissolved at the temperatures and concentrations existing within the PFR. After a residence time of 2 hours in the PFR, the finished aqueous hydrolyzate product contains 0.04% amide and 0.04% nitrile.

While the invention is susceptible to various modifications and alternative forms, specific embodiments thereof have been shown by way of example in the drawings and have been described herein in detail. It should be understood, however, that it is not intended to limit the invention to the particular form disclosed, but on the contrary, the intention is to cover all modifications, equivalents and alternatives falling within the spirit and scope of the invention as defined by the appended claims.

We claim:

1. A process for the preparation of 2-hydroxy-4-methylthiobutanoic acid or a salt thereof comprising:

introducing 2-hydroxy-4-methylthiobutanenitrile and an aqueous mineral acid into an aqueous hydrolysis mixture comprising 2-hydroxy-4-methylthiobutanamide, mineral acid, and unreacted 2-hydroxy-4-methylthiobutanenitrile;

hydrolyzing 2-hydroxy-4-methylthiobutanenitrile in said hydrolysis mixture in a continuous nitrile hydrolysis reactor comprising a back-mixed reaction zone and a circulation zone in fluid flow communication with said back-mixed reaction zone, said circulation zone comprising a circulating line;

continuously circulating said aqueous hydrolysis mixture in a circulating stream that is withdrawn from said back-mixed reaction zone, passed through said circulation zone and returned to said back-mixed reaction zone, said circulating stream as withdrawn from said back-mixed reaction zone containing unreacted 2-hydroxy-4-methylthiobutanenitrile;

removing a portion of said circulating aqueous hydrolysis mixture as a nitrile hydrolysis reactor product stream from a forward flow port in said circulation zone and transferring said nitrile hydrolysis reactor product stream to an amide hydrolysis flow reactor;

diluting said nitrile hydrolysis reactor product stream with water at a point downstream of said forward flow port to provide a finishing reaction stream;

hydrolyzing 2-hydroxy-4-methylthiobutanamide contained in said finishing reaction stream in said amide hydrolysis flow reactor to produce a finished aqueous hydrolyzate product containing 2-hydroxy-4-methylthiobutanoic acid;

the sum of the residence time of said circulating stream in said circulation zone upstream of said forward flow port and the residence time of said nitrile hydrolysis reactor product stream downstream of said forward flow port prior to dilution being sufficient to substantially extinguish residual 2-hydroxy-4-methylthiobutanenitrile prior to the dilution of said nitrile hydrolysis reactor product stream.

2. A process as set forth in claim 1 wherein the residual 2-hydroxy-4-methylthiobutanenitrile in said nitrile hydrolysis reactor product stream at said point of dilution is not greater than about 0.01 wt % based on the sum of the 2-hydroxy-4-methylthiobutanamide and 2-hydroxy-4-methylthiobutanoic acid contained in said product stream.

3. A process as set forth in claim 1 wherein the residual 2-hydroxy-4-methylthiobutanenitrile in said aqueous hydrolysis mixture exiting said nitrile hydrolysis reactor is at least about 0.05 wt % based on the sum of the 2-hydroxy-4-methylthiobutanamide and 2-hydroxy-4-methylthiobutanoic acid contained in said aqueous hydrolysis mixture.

4. A process as set forth in claim 1 wherein the flow in said circulating line is substantially turbulent, the temperature of said circulating stream is at least 50° C. throughout said circulation zone, and the residence time of said circulating stream in said circulation zone upstream of said forward flow port is at least about 3 seconds.

5. A process as set forth in claim 1 wherein between said forward flow port and said point of dilution the temperature of said nitrile hydrolysis reactor product stream is at least 50 ° C. and the residence time is at least about 30 seconds.

6. A process as set forth in claim 1 wheirin the equivalent of at least one sequential back-mixed reaction zone is provided in a nitrile extinction reaction region comprising the portion of said circulation zone upstream of said forward flow port and a forward flow reaction zone within which said nitrile reactor product stream flows between said forward flow port and said point of dilution.

7. A process as set forth in claim 1 wherein an external heat exchanger is positioned in said circulating line.

8. A process as set forth in claim 7 wherein said forward flow port is positioned in said circulating line upstream of said external heat exchanger.

9. A process as set forth in claim 7 wherein said aqueous mineral acid is introduced into said aqueous hydrolysis mixture at a port positioned in said circulating line downstream of said external heat exchanger.

10. A process as set forth in claim 1, wherein said nitrile hydrolysis reactor product stream is transferred to said point of dilution via a vertical downcomer line.

11. A process as set forth in claim 1 wherein said aqueous mineral acid, said water stream and said nitrile hydrolysis reaction product stream are mixed to form the finishing reaction stream that is introduced into the amide hydrolysis flow reactor.

12. A process as set forth in claim 11 wherein the molar ratio of mineral acid to 2-hydroxy-4-methylthiobutanenitrile added to said nitrile hydrolysis reactor being between about 0.6 and about 1.5, and the overall molar ratio of mineral acid to 2-hydroxy-4-methylthiobutanenitrile being between about 0.7 and about 1.5.

13. A process as set forth in claim 1 wherein the flow is laminar in a forward flow reaction zone within which said nitrile reactor product stream flows between said forward flow port and said point of dilution, and the equivalent of at least one sequential back-mixed reaction zone is provided in said forward flow reaction zone.

14. A process as set forth in claim 13 wherein the equivalent of between about 2 and about 3 sequential back-mixed reaction zones is provided in said forward flow reaction zone.

15. A process as set forth in claim 1 wherein the flow is turbulent in a forward flow reaction zone within which said nitrile reactor product stream flows between said forward flow port and said point of dilution, and the equivalent of at least one sequential back-mixed reaction zone is provided in said forward flow reaction zone.

16. A process as set forth in claim 5 wherein the flow in said zone between an inlet of said amide hydrolysis flow reactor and said point of dilution is turbulent.

17. A process as set forth in claim 1 wherein said finished aqueous hydrolyzate product comprises up to about 0.05 wt. % amide.

18. A process as set forth in claim 1 wherein the equivalent of at least two sequential back-mixed reaction zones is provided in said amide hydrolysis flow reactor.

19. A process as set forth in claim 1 wherein the equivalent of at least 35 sequential back-mixed reaction zones is provided in said amide hydrolysis flow reactor.

20. A process as set forth in claim 1 wherein the temperature within said amide hydrolysis flow reactor is controlled to maintain said finished aqueous hydrolyzate product at a color of less than about 10 on the Gardner scale.

21. A process for the preparation of 2-hydroxy-4-methylthiobutanoic acid or a salt thereof comprising:
  introducing 2-hydroxy-4-methylthiobutanenitrile and an aqueous mineral acid into an aqueous hydrolysis mixture comprising 2-hydroxy-4-methylthiobutanamide, mineral acid, and unreacted 2-hydroxy-4-methylthiobutanenitrile;
  hydrolyzing 2-hydroxy-4-methylthiobutanenitrile in said hydrolysis mixture in a continuous nitrile hydrolysis reactor comprising a back-mixed reaction zone and a circulation zone in fluid flow communication with said back-mixed reaction zone, said circulation zone comprising a circulating line;
  continuously circulating said aqueous hydrolysis mixture in a circulating stream that is withdrawn from said back-mixed reaction zone, passed through said circulation zone and returned to said back-mixed reaction zone, said circulating stream as withdrawn from said back-mixed reaction zone containing unreacted 2-hydroxy-4-methylthiobutanenitrile;
  removing a portion of said circulating aqueous hydrolysis mixture as a nitrile hydrolysis reactor product stream from a forward flow port in said circulation zone and transferring said nitrile hydrolysis reactor product stream to a continuous amide hydrolysis reactor;
  diluting said nitrile hydrolysis reactor product stream with water at a point downstream of said forward flow port to provide an amide hydrolysis mixture;
  feeding either said amide hydrolysis mixture, or said nitrile hydrolysis reactor product stream and water, to a continuous amide hydrolysis reactor in which a substantial portion of 2-hydroxy-4-methylthiobutanamide contained in said amide hydrolysis mixture is hydrolyzed to form a finishing reaction stream;
  transferring said finishing reaction stream to an amide hydrolysis flow reactor;
  hydrolyzing 2-hydroxy-4-methylthiobutanamide contained in said finishing reaction stream in said amide hydrolysis flow reactor to produce a finished aqueous hydrolyzate product containing 2-hydroxy-4-methylthiobutanoic acid;
  the sum of the residence time of said circulating stream in said circulation zone upstream of said forward flow port and the residence time of said nitrile hydrolysis reactor product stream downstream of said forward flow point prior to dilution being sufficient to substantially extinguish residual 2-hydroxy-4-methylthiobutanenitrile prior to the dilution of said nitrile hydrolysis reactor product stream.

22. A process as set forth in claim 21 wherein said nitrile hydrolysis reactor product stream is diluted with water in said continuous amide hydrolysis reactor.

23. A process as set forth in claim 21 wherein the residual 2-hydroxy-4-methylthiobutanenitrile in said nitrile hydrolysis reactor product stream at said point of dilution is not greater than about 0.01 wt % based on the sum of the 2-hydroxy-4-methylthiobutanamide and 2-hydroxy-4-methylthiobutanoic acid contained in said product stream.

24. A process as set forth in claim 21 wherein the residual 2-hydroxy-4-methylthiobutanenitrile in said aqueous hydrolysis mixture exiting said nitrile hydrolysis reactor is at least about 0.05 wt % based on the sum of the 2-hydroxy-4-methylthiobutanamide and 2-hydroxy-4-methylthiobutanoic acid contained in said aqueous hydrolysis mixture.

25. A process as set forth in claim 21 wherein the flow in said circulating line is substantially turbulent, the temperature of said circulating stream is at least about 50° C. throughout said circulation zone, and the residence time of said circulating stream in said circulation zone upstream of said forward flow port is at least about 3 seconds.

26. A process as set forth in claim 21 wherein between said forward flow port and said point of dilution the temperature of said nitrile hydrolysis reactor product stream is at least about 50° C. and the residence time is at least about 30 seconds.

27. A process as set forth in claim 21 wherein the equivalent of at least one sequential back-mixed reaction zone is provided in a nitrile extinction reaction region comprising the portion of said circulation zone upstream of said forward flow port and a forward flow reaction zone within which said nitrile reactor product stream flows between said forward flow port and said point of dilution or said continuous amide hydrolysis reactor.

28. A process as set forth in claim 24 wherein an external heat exchanger is positioned in said circulating line.

29. A process as set forth in claim 28 wherein said forward flow port is positioned in said circulating line upstream of said external heat exchanger.

30. A process as set forth in claim 28 wherein said aqueous mineral acid is introduced into said aqueous hydrolysis mixture at a port positioned in said circulating line downstream of said external heat exchanger.

31. A process as set forth in claim 21 wherein said nitrile hydrolysis reactor product stream is transferred to said point of dilution via a vertical downcomer line.

32. A process as set forth in claim 21 wherein said aqueous mineral acid, said water stream and said nitrile hydrolysis reaction product stream are mixed to form the finishing reaction stream that is introduced into the amide hydrolysis flow reactor.

33. A process as set forth in claim 32 wherein the molar ratio of mineral acid to 2-hydroxy-4-methylthiobutanenitrile added to said nitrile hydrolysis reactor being between about 0.6 and about 1.5, and the overall molar ratio of mineral acid to 2-hydroxy-4-methylthiobutanenitrile being between about 0.7 and about 1.5.

34. A process as set forth in claim 21 wherein the flow is laminar in a forward flow reaction zone within which said nitrile reactor product stream flows between said forward flow port and said point of dilution or said continuous amide hydrolysis reactor, and the equivalent of at least one sequential back-mixed reaction zone is provided in said forward flow reaction zone.

35. A process as set forth in claim 34 wherein the equivalent of between about 2 and about 3 sequential back-mixed reaction zones is provided in said forward flow reaction zone.

36. A process as set forth in claim 21 wherein the flow is turbulent in a forward flow reaction zone within which said nitrile reactor product stream flows between said forward flow point and said point of dilution, and the equivalent of at least one sequential back-mixed reaction zone is provided in said forward flow reaction zone.

37. A process as set forth in claim 21 wherein said finished aqueous hydrolyzate product comprises up to about 0.05 wt. % amide.

38. A process as set forth in claim 21 wherein the equivalent of at least two sequiential back-mixed reaction zones is provided in said amide hydrolysis flow reactor.

39. A process as set forth in claim 21 wherein the equivalent of at least 35 sequential back-mixed reaction zones is provided in said amide hydrolysis flow reactor.

40. A process as set forth in claim 21 wherein the temperature within said amide hydrolysis flow reactor is controlled to maintain said finished aqueous hydrolyzate product at a color of less than about 10 on the Gardner scale.

41. A process for the preparation of 2-hydroxy-4-methylthiobutanoic acid or a salt thereof comprising:

introducing 2-hydroxy-4-methylthiobutanenitrile and an aqueous mineral acid into an aqueous hydrolysis mixture comprising 2-hydroxy-4-methylthiobutanamide, mineral acid, and unreacted 2-hydroxy-4-methylthiobutanenitrile;

hydrolyzing 2-hydroxy-4-methylthiobutanenitrile in said hydrolysis mixture in a continuous nitrile hydrolysis reactor comprising a back-mixed reaction zone and a circulation zone in fluid flow communication with said back-mixed reaction zone, said circulation zone comprising a circulating line;

continuously circulating said aqueous hydrolysis mixture in a circulating stream that is withdrawn from said back-mixed reaction zone, passed through said circulation zone and returned to said back-mixed reaction zone, said circulating stream as withdrawn from said back-mixed reaction zone containing unreacted 2-hydroxy-4-methylthiobutanenitrile;

removing a portion of said circulating aqueous hydrolysis mixture as a nitrile hydrolysis reactor product stream from a forward flow port in said circulation zone and transferring said nitrile hydrolysis reactor product stream to an amide hydrolysis flow reactor;

diluting said nitrile hydrolysis reactor product stream with water at a point downstream of said forward flow port to provide a finishing reaction stream;

hydrolyzing 2-hydroxy-4-jethylthiobutanamide contained in said finishing reaction stream in said amide hydrolysis flow reactor to produce a finished aqueous hydrolyzate product containing 2-hydroxy-4-methylthiobutanoic acid;

the sum of the residence time of said circulating stream in said circulation zone upstream of said forward flow port and the residence time of said nitrile hydrolysis reactor product stream downstream of said forward flow port prior to dilution being at least about 20 seconds.

42. A process as set forth in claim 41 wherein the sum of the residence times is between about 30 seconds and about 5 minutes.

43. A process as set forth in claim 41 wherein the flow in said circulating line is substantially turbulent, and the residence time of said circulating stream in said circulation zone upstream of said forward flow port is at least about 3 seconds.

44. A process as set forth in claim 41 wherein between said forward flow port and said point of dilution the residence time is at least about 30 seconds.

45. A process as set forth in claim 41 wherein the equivalent of at least one sequential back-mixed reaction zone is provided in a nitrile extinction reaction region comprising the portion of said circulation zone upstream of said forward flow port and a forward flow reaction zone within which said nitrite reactor product stream flows between said forward flow port and said point of dilution.

46. A process as set forth in claim 41 wherein an external heat exchanger is positioned in said circulating line.

47. A process as set forth in claim 46 wherein said forward flow port is positioned in said circulating line upstream of said external heat exchanger.

48. A process as set forth in claim 46 wherein said aqueous mineral acid is introduced into said aqueous hydrolysis mixture at a port positioned in said circulating line downstream of said external heat exchanger.

49. A process as set forth in claim 41 wherein said nitrile hydrolysis reactor product stream is transferred to said point of dilution via a vertical downcomer line.

50. A process as set forth in claim 41 wherein said aqueous mineral acid, said water stream and said nitrile hydrolysis reaction product stream are mixed to form the finishing reaction stream that is introduced into the amide hydrolysis flow reactor.

51. A process as set forth in claim 50 wherein the molar ratio of mineral acid to 2-gydroxy-4-methylthiobutanenitrile added to said nitrile hydrolysis reactor being between about 0.6 and about 1.5, and the overall molar ratio of mineral acid to 2-hydroxy-4-methylthiobutanenitrile added to said amide hydrolysis flow reactor being between about 0.7 and about 1.5.

52. A process as set forth in claim 41 wherein the flow is laminar in a forward flow reaction zone within which said nitrile reactor product stream flows between said forward flow port and said point of dilution, and the equivalent of at least one sequential back-mixed reaction zone is provided in said forward flow reaction zone.

53. A process as set forth in claim 52 wherein the equivalent of between about 2 and about 3 sequential back-mixed reaction zones is provided in said forward flow reaction zone.

54. A process as set forth in claim 41 wherein the flow is turbulent in a forward flow reaction zone within which said nitrile reactor product stream flows between said forward flow port and said point of dilution, and the equivalent of at least one sequential back-mixed reaction zone is provided in said forward flow reaction zone.

55. A process as set forth in claim 41 wherein said finished aqueous hydrolyzate product comprises up to about 0.05 wt. % amide.

56. A process as set forth in claim 41 wherein the equivalent of at least two sequential back-mixed reaction zones is provided in said amide hydrolysis flow reactor.

57. A process as set forth in claim 41 wherein the equivalent of at least 35 sequential back-mixed reaction zones is provided in said amide hydrolysis flow reactor.

58. A process for the preparation of 2-hydroxy-4-methylthiobutanoic acid or a salt thereof comprising:

introducing an aqueous mineral acid into a nitrile hydrolysis reactor comprising a continuous stirred tank reactor;

introducing 2-hydroxy-4-mcthylthiobutanenitrile into said nitrile hydrolysis reactor;

continuously hydrolyzing 2-hydroxy-4-methylthiobutanenitrile within said nitrile hydrolysis reactor to produce a nitrile hydrolysis reactor product stream containing 2-hydroxy-4-metlhylthiobutanamide;

continuously introducing water and said nitrile hydrolysis reactor product stream into an amide hydrolysis flow reactor;

continuously hydrolyzing 2-hydroxy-4-methylthiobutanamide within said amide hydrolysis flow reactor to produce a finished aqueous hydrolyzate product containing 2-hydroxy-4-methylthiobutanoic acid; and recovering 2-hydroxy-4-methylthiobutanoic acid by extracting said finished aqueous hydrolyzate product with an organic solvent to form a 2-hydroxy-4-methylthiobutanoic acid-containing organic phase and an aqueous phase, and subjecting said 2-hydroxy-4-methylthiobutanoic acid-containing organic phase to evaporation to provide concentrated 2-hydroxy-4-methylthiobutanoic acid containing less than about 4 wt. % water and at least about 96 wt % 2-hydroxy-4-methylthiobutanoic acid.

59. The process as set forth in claim 58 wherein 2-hydroxy-4-methylthiobutnenitrile is continuously hydrolyzed within said first reactor while continuously removing heat of nitrile hydrolysis from the reacting mixture in said first reactor to produce an intermediate aqueous hydrolysis solution containing 2- hydroxy-4-methylthiobutanamide, the conversion of 2-hydroxy-4-methylthiobutanentrile to 2-methylthiobutanamide in said first reactor being at least about 90%.

60. A process for the preparation of 2-hydroxy-4-methylthiobutanoic acid or a salt thereof comprising:

introducing an aqueous mineral acid into a nitrile hydrolysis reactor comprising a continuous stirred tank reactor;

introducing 2-hydroxy-4-methylthiobutanenitrile into said nitrile hydrolysis reactor;

continuously hydrolyzing 2-hydroxy-4-methylthiobutanenitrile within said nitrile hydrolysis reactor to produce a nitrile hydrolysis reactor product stream containing 2-hydroxy-4-methylthiobutanamide;

continuously introducing water and said nitrile hydrolysis reactor product stream into an amide hydrolysis flow reactor;

continuously hydrolyzing 2-hydroxy-4-methylthiobutanamide within said amide hydrolysis flow reactor to produce a finished aqueous hydrolyzate product containing 2-hydroxy-4-methylthiobutanenitrile acid; and recovering 2-hydroxy-4-methylthiobutanoic acid by neutralizing said finished aqueous hydrolyzate procudt and extracting with a solvent to form an organic phase containing 2-hydroxy-4-methylthiobutanoic acid and an aqueous phase, treating said organic phase with aqueous ammonia to form a second aquesous phase contiaing an ammonium salt of 2-hydroxy-4-methylthiobutanoic acid and a second organic phase, and recovering the ammonium salt of 2-hydroxy-4-methylthiobutanoic acid from said second aqueous phase.

61. The process as set forth in claim 60 wherein 2-hydroxy-4-methylthiobutanenitrile is continuously hydrolyzed within said first reactor while continuously removing heat of nitrile hydrolysis form the reacting mixture in said first reactor to produce an intermediate aqueous hydrolysis solution containing 2-hydroxy-4-methylthiobutanamide, the conversion of 2-hydroxy-4-methylthiobutanenitrile to 2-methylthibutanamide in said first reactor being at least about 90%.

62. A process for the preparation of 2-hydroxy-4-methylthiobutanoic acid or a salt thereof comprising:

introducing an aqueous mineral acid into a nitrile hydrolysis reactor comprising a continuous stirred tank reactor;

introducing 2-hydroxy-4-methylthiobutanenitrile into said nitrile hydrolysis reactor;

continuously hydrolyzing 2-hydroxy-4-methylthiobutanenitrile within said nitrile hydrolysis reactor to produce a nitrile hydrolysis reactor product stream containing 2-hydroxy-4-methylthiobutanamide;

continuously introducing water and said nitrile hydrolysis reactor product stream into an amide hydrolysis flow reactor;

continuously hydrolyzing 2-hydroxy-4-methylthiobutanamide within said amide hydrolysis flow reactor to produce a finished aqueous hydrolyzate product containing 2-hydroxy-4-methylthiobutanoic acid; and recovering 2-hydroxy-4-methylthiobutanoic acid by subjecting said finished aqueous hydrolyzate product to evaporation to obtain an HMBA-containing salt residue, treating said residue with an organic solvent to form a suspension, separating solids from said suspension to form an HMBA-containing solution, removing said organic solvent from said HMBA-containing solution to obtain an HMBA residue, and adding water to said HMBA residue to form an HMBA solution.

63. The process as set forth in claim 62 wherein 2-hydroxy-4-methylthiobutanenitrile is continuously hydrolyzed within said first reactor while continuously removing heat of nitrile hydrolysis from the reacting mixture is said first reactor to produce an intermediate aqueous hydrolysis solution containing 2-hydroxy-4-methylthiobutanamide, the conversion of 2-hydroxy-4-methylthiobutanenitrile to 2-methylthibutanamide in said first reactor being at least about 90%.

64. A process for the preparation of 2-hydroxy-4-methylthiobutanoic acid or a salt thereof comprising:

introducing an aqueous mineral acid into a nitrile hydrolysis reactor comprising a first continuous stirred tank reactor;

introducing 2-hydroxy-4-methylthiobutanenitrile into said nitrile hydrolysis reactor;

continuously hydrolyzing 2-hydroxy-4-methylthiobutanenitrile within said nitrile hydrolysis reactor to produce a nitrile hydrolysis reactor product stream contiaing 2-hydroxy-4-methylthiobutanamide;

continuously introducing said nitrile hydrolysis reactor product stream exiting said nitrile hydrolysis reactor and water into a continuous stirred tank reactor such that a substantial portion of 2-hydroxy-4-methylthiobutanamide contained in said nitrile hydrolysis reactor product stream is hydrolyzed in said second continuous stirred tank reactor to form a finishing reactor stream;

continuously introducing said finished reactor stream into an amide hydrolysis flow reactor; continuously hydrolyzing 2-hydroxy-4-methylthiobutanamide within said amide hydrolysis flow reactor to produce a finished aqueous hydrolyzate product contianing 2-hydroxy-4-methylthiobutanoic acid; and recovering 2-hydroxy-4-methylthiobutanoic acid by extracting said finished aqueous hydrolyzate product with an organic solvent to form a 2-hydroxy-4-methylthiobutanoic acid-containing organic phase and an aqueous phase, and subjecting said 2-hydroxy-4- methylthiobutanoic acid-containing organic phase to evaporation to provide concentrated 2-hydroxy-4-methylthiobutanoic acid containing less than about 4 wt. % water and at least about 96 wt. % 2-hydroxy-4-methylthiobutanoic acid.

65. The process as set forth in claim 64 wherein 2-hydroxy-4-methylthiobutanenitrile is continuously hydrolyzed within said first reactor while continuously removing heat of nitrile hydrolysis from the reacting mixture in said first reactor to produce an intermediate aqueous hydrolysis solution containing 2-hydroxy-4-methylthiobutanamide, the conversion of 2-hydroxy-4-methylthiobutanenitrile to 2-methylthiobutanamide in said first reactor being at least about 90%.

66. A process for the preparation of 2-hydroxy-4-methylthiobutanoic acid or a salt thereof comprising:
introducing an aqueous mineral acid into a nitrile hydrolysis reactor comprising a first continuous stirred tank reactor;
introducing 2-hydroxy-4-methylthiobutanenitrile into said nitrile hydrolysis reactor;
continuously hydrolyzing 2-hydroxy-4-methylthiobutanenitrile within said nitrile hydrolysis reactor to produce a nitrile hydrolysis reactor product stream containing 2-hydroxy-4-methylthiobutanamide;
continuously introducing said nitrile hydrolysis reactor product stream exiting said nitrile hydrolysis reactor and water into a continous amide hydrolysis
reactor comprising a second continuous stirred tank reactor such that a substantial portion of 2-hydroxy-4-methylthiobutanoic contained in said nitrile hydrolysis reactor product stream is hydrolyzed in said second continuous stirred tank reactor to form a finishing reaction stream;
continuously introducing said finishing reactor stream into an amide hydrolysis flow reactor;
continuously hydrolyzing 2-hydroxy-4-methylthiobutanenitrile within said amide hydrolysis flow reactor to produce a finished aqueous hydrolyzate product containing 2-hydroxy-4-methylthiobutanoic acid; and
recovering 2-hydroxy-4-methylthiobutanoic acid by neutralizing said finished aqueous hydrolyzing product and extracting with a solvent to form an organic phase containing 2-hydroxy-4-methylthiobutanoic acid and an aqueous phase, treating said organic phase with aqueous ammonia to form a second aqueous phase contianing an ammonium salt of 2-hydroxy-4-methylthiobutanoic acid and a second organic phase, and recovering the ammonium salt of 2-hydroxy-4-methylthiobutanoic acid from said second aqueous phase.

67. The process as set forth in claim 66 wherein 2-hydroxy-4-methylthiobutanenitrile is continuously hydrolyzed within said first reactor while continuously removing heat of nitrile hydrolysis form the reacting mixture in said first reactor to produce an intermediate aqueous hydrolysis solution containing 2-hydroxy-4-methylthiobutanamide, the conversion of 2-hydroxy-4-methylthiobutanenitrile to 2-methylthiobutanamide in said first reactor being at least about 90%.

68. A process for the preparation of 2-hydroxy-4-methylthiobutanoic acid or a salt thereof comprising:
introducing an aqueous mineral acid into a nitrile hydrolysis reactor comprising a first continuous stirred tank reactor;
introducing 2-hydroxy-4-methylthiobutanenitrile into said nitrile hydrolysis reactor;
continuously hydrolyzing 2-hydroxy-4-methylthiobutanenitrile within said nitrile hydrolysis reactor to produce a nitrile hydrolysis reactor product stream containing 2-hydroxy-4-methylthiobutanamide;
continuously introducing said nitrile hydrolysis reactor product stream exiting said nitrile hydrolysis reactor and water into a continuous amide hydrolysis reactor comprising a second continuous stirred tank reactor such that a substantial portion of 2-hydroxy-4-methylthiobutanamide contained in said nitrile hydrolysis reactor product stream is hydrolyzed in said second continuous stirred tank reactor to form a finishing reactor stream;
continuously introducing said finishing reaction stream into an amide hydrolysis flow reactor;
continuously hydrolyzing 2-hydroxy-4-methylthiobutanamide within said amide hydrolysis flow reactor to produce a finished aqueous hydrolyzate product containing 2-hydroxy-4-methylthiobutanoic acid; and
recovering 2-hydroxy-4-methylthiobutanoic acid by subjecting said finshed aqueous hydrolyzate product to evaporation to obtrain an HMBA-containing salt residue, treating said residue with an organic solvent to form a suspension, separating solids from said suspension to form an HMBA-contianing solution, removing said organic solvent from said HMBA-containing solution to obtain an HMBA redidue, and adding water to said HMBA residue to form an HMBA solution.

69. The process as set forth in claim 68 wherin 2-hydroxy-4-methylthiobutanenitrile is continuously hydrolyzed within said first reactor while continuously removing heat of nitrile hydrolysis from the reacting mixture in said first reactor to produce an intermediate aqueous hydrolysis solution containing 2-hydroxy-4-methylthiobutanamide, the conversion of 2-hydroxy-4-methylthiobutanenitrile to 2-methylthiobutanamide in said first reactor being at least about 90%.

70. A process for the preparation of 2-hydroxy-4-methylthiobutanoic acid or a salt thereof compriing:
introducing an aqueous mineral acid and 2-hydroxy-4-methylthiobutanenitrile into a nitrile hydrolysis reactor;
continuously hydrolyzing 2-hydroxy-4-methylthiobutanenitrile within said nitrile hydrolysis reactor to produce a nitrile hydrolysis reactor product stream containing 2-hydroxy-4-methylthiobutanamide;
continuously introducing water, aqueous mineral acid, and said nitrile hydrolysis reactor product stream into an amide hydrolysis flow reactor;
continuously hydrolyzing 2-hydroxy-4-methylthiobutanamide within said amide hydrolysis reactor to produce a finished aqueous hydrolyzate product containing 2-hydroxy-4-methylthiobutanoic acid; and
recovering 2-hydroxy-4-methylthiobutanoic acid by extracting said finished aqueous hydrolyzate product with an organic solvent to form a 2-hydroxy-4-methylthiobutanoic acid-containing organic phase and an aqueous phase, and subjecting said 2-hydroxy-4-methylthiobutanoic acid-containing organic phase to evaporation to provide concentrated 2-hydroxy-4-methylthiobutanoic acid containing less than about 4 wt. % water and at least about 96 wt. % 2-hydroxy-4-methylthiobutanoic acid.

71. The process as set forth in claim 70 wherein the aqueous mineral acid sulfuric acid.

72. A process for the preparatino of 2-hydroxy-4-methylthiobutanoic acid or a salt thereof comprising:
introducing an aqueous mineral acid and 2-hydroxy-4-methylthiobutanenitrile into a nitrile hydrolysis reactor;
continuously hydrolyzing 2-hydroxy-4-methylthiobutanenitrile within said nitrile hydrolysis reactor to produce a nitrile hydrolysis reactor product stream contianing 2-hydroxy-4-methylthiobutanamide;
continuously introducing water, aqueous mineral acid, and said nitrile hydrolysis reactor product stream into an amide hydrolysis flow reactor;
continuously hydrolyzing 2-hydroxy-4-methylthiobutanamide within said amide hydrolysis reactor to produce a finished aqueous hydrozylate product containing 2-hydroxy-4-methylthiobutanoic; and
recovering 2-hydroxy-4-methylthiobutanoic acid by neutralizing said finished aqueous hydrolyzate product and extracting with a solvent to form an organic phase contianing 2-hydroxy-4-methylthiobutanoic acid and an aqueous phase, treating said organic phase with aqueous ammonia to form a second aqueous phase containing an ammonium salt of 2-hydroxy-4-methylthiobutanoic acid and a second organic phase, and recovering the ammonium salt of 2-hydroxy-4-methylthiobutanoic acid from said second aqueous phase.

73. The process as set forth in claim 72 wherein the aqueous mineral acid is sulfuric acid.

74. The process for the preparation of 2-hydroxy-4-methylthiobutanoic acid or a salt thereof comprising:
introducing an aqueous mineral acid and 2-hydroxy-4-methylthiobutanenitrile into a nitrile hydrolysis reactor;
continuously hydrolyzing 2-hydroxy-4-methylthiobutanenitrile within said nitrile hydrolysis reactor to produce a nitrile hydrolysis reactor product stream contianing 2-hydroxy-4-methylthiobutanamide;
continuously introducing water, aqueous mineral acid, and said nitrile hydrolysis reactor product stream into an amide hydrolysis flow reactor;
continuously hydrolyzing 2-hydroxy-4-methylthiobutanamide within said amide hydrolysis reactor to produce a finished aqueous hydrolyzate product containing 2-hydroxy-4-methylthiobutanoic acid; and
recovering 2-hydroxy-4-methylthiobutanoic acid by sujecting said finished aqueous hydrolyzate product to evaporation to obtain an HMBA-containing salt residue, treating said residue with an organic solvent to form a suspension, separating solids from said suspension to form an HMBA-containing soltuion, removing said organic solvent from said HMBA-containing solution to obtain an HMBA residue, and adding water to said HMBA residue to form an HMBA soltuion.

75. The process as set forth in claim 74 wherein the aqueous mineral acid is sulfuric acid.

76. A process for the preparation of 2-hydroxy-4-methylthiobutanoic acid or a salt thereof comprising:
concurrently introducing 2-hydroxy-4-methylthiobutanenitrile, a concentrated sulfuric acid stream having a strength of between about 70% by weight and about 99% by weight, and water into a vessel in which 2-hydroxy-4-methylthiobutanenitrile is hydrolyzed, water and sulfuric acid being added in such relative proportions so as to provide a mixture comprising sulfuric acid having a strength between about 50% and about 70% by weight on an orgainc-free basis;
hydrolyzing 2-hydroxy-4-methylthiobutanenitrile within said vessel to produce a nitrile hydrolysis product stream containing 2-hydroxy-4-methylthiobutanamide;
hydrolyzing 2-hydroxy-4-methylthiobutanamide to produce a finished aqueous hydrolyzate product containing 2-hydroxy-4-methylthiobutanoic acid; and
recovering 2-hydroxy-4-methylthiobutanoic acid by extracting said finished aqueous hydrolyzate product with an organic solvent to form a 2-hydroxy-4-methylthiobutanoic acid-containing organic phase and an aqueous phase, and subjecting said 2-hydroxy-4-methylthiobutanoic acid-containing organic phase to evaporation to provide concentrated 2-hydroxy-4-methylthiobutanoic acid containing less than about 4 wt. % water and at least about 96 wt. % 2-hydroxy-4-methylthiobutanoic acid.

77. A process for the preparation of 2-hydroxy-4-methylthiobutanoic acid or a salt thereof comprising:
concurrently introducing 2-hydroxy-4-methylthiobutanenitrile, a concentrated sulfuric acid stream having a strength of between about 70% by weight and about 99% by weight, and water into a vessel in which 2-hydroxy-4-methylthiobutanenitrile is hydrolyzed, water and sulfuric acid being added in such relative proportions so as to provide a mixture comprising sulfuric acid having a strength between about 50% and about 70% by weight on an organic-free basis;
hydrolyzing 2-hydroxy-4-methylthiobutanenitrile within said vessle to produce a nitrile hydrolysis product stream containing 2-hydroxy-4-methylthiobutanamide;
hydrolyzing 2-hydroxy-4-methylthiobutanamide to produce a finsihed aqueous hydrolyzate product containing 2-hydroxy-4-methylthiobutanoic acid; and
recovering 2-hydroxy-4-methylthiobutanoic acid by neutralizing said finished aqueous hydrolyzate product and extracting with a solvent to form an organic phase containing 2-hydroxy-4-methylthiobutanoic acid and an aqueous phase, treating said organic phase with aqueous ammonia to form a second aqueous phase containing an ammonium salt of 2-hydroxy-4-methylthiobutanoic acid and a second organic phase, and recovering the ammonium salt of 2-hydroxy-4-methylthiobutanenitrile acid from said second aqueous phase.

78. A process for the prepartion of 2-hydroxy-4-methylthiobutanoic acid or a salt thereof comprising:
concurrently introducing 2-hydroxy-4-methylthiobutanenitrile, a concentrated sulfuric acid stream having a strength of between about 70% by weight and about 99% by weight, and water into a vessel in which 2-hydroxy-4-methylthiobutanenitrile is hydrolyzed, water and sulfuric acid being added in such relative proportions so as to provide a mixture comprising sulfuric acid having a strength between about 50% and about 70% by weight on an orgainc-free basis;
hydrolyzing 2-hydroxy-4-methylthiobutanenitrile within said vessel to produce a nitrile hydrolysis product stream containing 2-hydroxy-4-methylthiobutanamide;
hydrolyzing 2-hydroxy-4-methylthiobutanamide to produce a finished aqueous hydrolyzate product containing 2-hydroxy-4-methylthiobutanoic acid; and
recovering 2-hydroxy-4-methylthiobutanoic acid by subjecting said finished aqueous hydrolyzate product to evaporation to obtain an HMBA-containing salt residue, treating said residue with an organic solvent to form a suspension, separating solids from said suspension to form an HMBA-containing solution, removing said organic solvent from said HMBA-contianing solution to obtain an HMBA residue, and adding water to said HMBA residue to form an HMBA solution.

79. The process as set forth in claim 1 wherein 2-hydroxy-4-methylthiobutanoic acid is recovered by extracting said finsihed aqueous hydrolyzate product with an organic solvent to form a 2-hydroxy-4-methylthiobutanoic acid-containing organic phase and an aqueous phase, and subjecting said 2-hydroxy-4-methylthiobutanoic acid-containing organic phase to evaporation to provide concentrated 2-hydroxy-4-methylthiobutanoic acid containing less than about 4 wt. % water and at least about 96 wt. % 2-hydroxy-4-methylthiobutanoic acid.

80. The process as set forth in claim 1 wherein 2-hydroxy-4-methylthiobutanoic acid is recovered by neutralizing said finished aqueous hydrolyzate product and extracting with a solvent to form an organic phase containing 2-hydroxy-4-methylthiobutanoic acid and an aqueous phase, treating said organic phase with aqueous ammonia to form a second aqueous phase containing an ammonium salt of 2-hydroxy-4-methylthiobutanoic acid and a second organic phase, and recovering the ammonium salt of 2-hydroxy-4-methylthiobutanoic acid from said second aqueous phase.

81. The process as set forth in claim 1 wherein 2-hydroxy-4-methylthiobutanoic acid is recovered by subjecting said fnished aqueous hydrolyzate product to evaporation to obtain an HMBA-containing salt residue, treating said residue with an organic solvent to form a suspension, separating solids from said suspension to form an HMBA-contianing solution, removing said organic solvent from said HMBA-containing solution to obtain an HMBA residue, and adding water to said HMBA residue to form an HMBA solution.

82. The process as set forth in claim 21 wherein 2-hydroxy-4-methylthiobutanoic acid is recovered by extracting said finsihed aqueous hydrolyzate product with an organic solvent to form a 2-hydroxy-4-methylthiobutanoic acid-containing organic phase and an aqueous phase, and subjecting said 2-hydroxy-4-methylthiobutanoic acid-containing organic phase to evaportion to provide concentrated 2-hydroxy-4-methylthiobutanoic acid containing less than about 4 wt. % water and at least about 96 wt. % 2-hydroxy-4-methylthiobutanoic acid.

83. The process as set forth in claim 21 wherein 2-hydroxy-4-methylthiobutanoic acid is recovered by neutralizing said finished aqueous hydrolyzate product and extracting with a solvent to form an organic phase containing 2-hydroxy-4-methylthiobutanoic acid and an aqueous phase, treating said organic phase with aqueous ammonia to form a second aqueous phase containing an ammonium salt of 2-hydroxy-4-methylthiobutanoic acid and a second organic phase, and recovering the ammonium salt of 2-hydroxy-4-methylthiobutanoic acid from said second aqueous phase.

84. The process as set forth in claim 21 whrein 2-hydroxy-4-methylthiobutanoic acid is recovered by subjecting said finished aqueous hydrolyzate product to evaporation to obtain an HMBA-containing salt residue, treating said residue with an organic solvent to form a suspension, separating solids from said suspension to form an HMBA-containing solution, removing said organic solvent from said HMBA-containing solution to obtain an HMBA residue, and adding water to said HMBA residue to form an HMBA solution.

85. The process as set forth in claim 41 wherein 2-hydroxy-4-methylthiobutanoic acid is recovered by extracting said finished aqueous hydrolyzate product with an organic solvent to form a 2-hydroxy-4-methylthiobutanoic acid-containing organic phase and an aqueous phase, and sujecting said 2-hydroxy-4-methylthiobutanoic acid-containing organic phase to evaporation to provide concentrated 2-hydroxy-4-methylthiobutanoic acid containing less than about 4 wt. % water and at least about 96 wt. % 2-hydroxy-4-methylthiobutanoic acid.

86. The process as set forth in claim 41 wherein 2-hydroxy-4-methylthiobutanoic acid is recovered by neutralizing said finished aqueous hydrolyzate product and extracting with a solvent to form an organic phase containing 2-hydroxy-4-methylthiobutanoic acid and an aqueous phase, treating said organic phase with aqueous ammonia to form a second aqueous phase containing an ammonium salt of 2-hydroxy-4-methylthiobutanoic acid and a second organic phase, and recovering the ammonium salt of 2-hydroxy-4-methylthiobutanoic acid from said second aqueous phase.

87. The process as set forth in claim 41 wherein 2-hydroxy-4-methylthiobutanoic acid is recovered by subjecting said finished aqueous hydrolyzate product to evaporation to obtain an HMBA-containing salt residue, treating said residue with an organic solvent to form a suspension, separating solids from said suspension to form an HMBA-containing solution, removing said organic solvent from said HMBA-containing solution to obtain an HMBA residue, and adding water to said HMBA residue to form an HMBA solution.

88. A process for the preparation of 2-hydroxy-4-methylthiobutanoic acid or a salt thereof comprising:

concurrently introducing 2-hydroxy-4-methylthiobutanenitrile, concentrated sulfuric acid stream having a strength of between about 70% by weight and about 99% by weight, and water into a vessel in which 2-hydroxy-4-methylthiobutanenitrile is hydrolyzed;

hydrolyzing 2-hydroxy-4-methylthiobutanenitrile within said vessle to produce an intermediate aqueous hydrolyzate solution containing 2-hydroxy-4-methylthiobutanamide;

adding water to said intermediate solution;

hydrolyzing 2-hydroxy-4-methylthiobutanamide to produce an aqueous hydrolyzate product solution containing 2-hydroxy-4-methylthiobutanoic acid; and recovering 2-hydroxy-4-methylthiobutanoic acid by extracting said finished aqueous hydrolyzate product with an organic solvent to form a 2-hydroxy-4-methylthiobutanoic acid-containing organic phase and an aqueous phase, and subjecting said 2-hydroxy-4-methylthiobutanoic acid-containing organic phase to evaporation to provide concentrated 2-hydroxy-4-methylthiobutanoic acid containing less than about 4 wt. % water and at least about 96 wt. % 2-hydroxy-4-methylthiobutanoic acid.

89. A process for the preparation of 2-hydroxy-4-methylthiobutanoic acid or a salt thereof comprising:

concurrently introducing 2-hydroxy-4-methylthiobutanenitrile, concentrated sulfuric acid stream having a strength of between about 70% by weight and about 99% by weight, and water into a vessel in which 2-hydroxy-4-methylthiobutanenitrile is hydrolyzed;

hydrolyzing 2-hydroxy-4-methylthiobutanenitrile within said vessle to produce an intermdeiate aqueous hydrolyzate solution containing 2-hydroxy-4-methylthiobutanamide;

adding water to said intermediate solution;

hydrolyzing 2-hydroxy-4-methylthiobutanamide to produce an aqueous hydrolyzate product solution containing 2-hydroxy-4-methylthiobutanoic acid; and recovering 2-hydroxy-4-methylthiobutanoic acid by neutralizing said finished aqueous hydrolyzate product and extracting with a solvent to form an organic phase containing 2-hydroxy-4-methylthiobutanoic acid and an aqueous phase, treating said organic phase containing an ammonia salt of 2-hydroxy-4-methylthiobutanoic acid and a second organic phase, and recovering the ammonium salt of 2-hydroxy-4-methylthiobutanoic acid from said second aqueous phase.

90. A process for the preparation of 2-hydroxy-4-methylthiobutanoic acid or salt thereof comprising:

concurrently introducing 2-hydroxy-4-methylthiobutanenitrile, concentrated sulfuric acid stream having a strength of between about 70% by weight and about 99% by weight, and water into a vessel in which 2-hydroxy-4-methylthiobutanenitrile is hydrolyzed;

hydrolyzing 2-hydroxy-4-methylthiobutanenitrile within said vessel to produce an intermediate aqueous hydrolyzate solution containing 2-hydroxy-4-methylthiobutanamide;

adding water to said intermediate solution;

hydrolyzing 2-hydroxy-4-methylthiobutanamide to produce an aqueous hydrolyzate product soltuion containing 2-hydroxy-4-methylthiobutanoic acid; and recovering 2-hydroxy-4-methylthiobutanoic acid by subjecting said finished aqueous hydrolyzate product to evaporation to obtain an HMBA-containing salt residue, treating said residue with an organic solvent to form a suspension, separating solids from said suspension to form an HMBA-containing solution, removing said organic solvent from said HMBA-containing solution to obtain an HMBA residue, and adding water to said HMBA residue to form an HMBA solution.

91. A process for the preparation of 2-hydroxy-4-methylthiobutanoic acid or a salt thereof comprising:

contacting 2-hydroxy-4-methylthiobutanenitrile with mineral acid in a nitrile hydrolysis reactor to produce an intermediate hydrolyzate comprising 2-hydroxy-4-methylthiobutanamide;

mixing said intermediate hydrolyzate with water to produce a finishing reactor solution; and passing said finishing reactor solution through a plug flow reactor for hydrolysis of 2-hydroxy-4-methylthiobutanoic to form 2-hydroxy-4-methylthiobutanenitrile acid without liquid phase separation within said plug flow reactor.

92. The process as set forth in claim 91 wherein wherein 2-hydroxy-4-methylthiobutanoic acid is recovered by extracting said finished aqueous hydrolyzate product with an organic solvent to form a 2-hydroxy-4-methylthiobutanoic acid-containing organic phase and an aqueous phase, and subjecting said 2-hydroxy-4-methylthiobutanoic acid-containing organic phase to evaporation to provide concentrated 2-hydroxy-4-methylthiobutanoic acid containing less than about 4 wt. % water and at least about 96 wt. % 2-hydroxy-4-methylthiobutanoic acid.

93. The process as set forth in claim 91 wherien 2-hydroxy-4-methylthiobutanoic acid is recovered by neutralizing said finished aqueous hydrolyzate product and extracting with a solvent to form an organic phase containing 2-hydroxy-4-methylthiobutanoic acid and an aqueous phase, treating said organic phase with aqueous ammonia to form a second aqueous phase containing an ammonium salt of 2-hydroxy-4-methylthiobutanoic acid and a second organic phase, and recovering the ammonium salt of 2-hydroxy-4-methylthiobutanoic acid from said second aqueous phase.

94. The process as set forth in claim 91 wherein 2-hydroxy-4-methylthiobutanoic acid is recovered by subjecting said finished aqueous hydrolyzate product to evaporation to obtain an HMBA-containing salt residue, treating said residue with an organic solvent to form a suspension, separating solids from said suspension to form an HMBA-containing solution, removing said organic solvent from said HMBA-containing solution to obtain an HMBA residue, and adding water to said HMBA residue to form an HMBA solution.

95. A process for the preparation of 2-hydroxy-4-methylthiobutanoic acid or a salt thereof comprising:

contacting 2-hydroxy-4-methylthiobutanenitrile with mineral acid in a nitrile hydrolysis reactor to produce an intermediate hydrolyzate comprising 2-hydroxy-4-methylthiobutanamide;

mixing said intermediate hydrolyzate with water to produce a finishing reaction solution; and passing said finishing reaction solution through a plug flow reactor for hydrolysis of 2-hydroxy-4-methylthiobutanoic to form 2-hydroxy-4-methylthiobutanoic acid, said plug flow reactor being operated at a Peclet number of at least about 50, a peak temperature of between about 90 and about 120 degrees C., and a residue time of between about 30 and about 90 minutes.

96. The process as set forth in claim 95 wherein wherein 2-hydroxy-4-methylthiobutanoic acid is recovered by extracting said finished aqueous hydrolyzate product with an organic solvent to form a 2-hydroxy-4-methylthiobutanoic acid-containing organic phase and an aqueous phase, and subjecting said 2-hydroxy-4-methylthiobutanoic acid-containing phase to evaporation to provide concentrated 2-hydroxy-4-methylthiobutanoic acid containing less than about 4 wt. % water and at least about 96 wt. % 2-hydroxy-4-methylthiobutanoic acid.

97. The process as set forth in claim 91 wherein 2-hydroxy-4-methylthiobutanoic acid is recovered by neutralizing said finished aqueous hydrolyzate product and extracting with a solvent to form an organic phase containing 2-hydroxy-4-methylthiobutanoic acid and an aqueous phase, treating said organic phase with aqueous ammonia to form a second aqueous phase containing an ammonium salt of 2-hydroxy-4-methylthiobutanoic acid and a second organic phase, and recovering the ammonium salt of 2-hydroxy-4-methylthiobutanoic acid from said second aqueous phase.

98. The process as set forth in claim 95 wherein 2-hydroxy-4-methylthiobutanoic acid is recovered by subjecting said finished aqueous hydrolyzate product to evaporation to obtain an HMBA-containig salt residue, treating said residue with an organic solvent to form a suspension, separating solids from said suspension to form an HMBA-containing solution, removing said organic solvent from said HMBA-containing solution to obtain an HMBA residue, and adding water to said HMBA residue to form an HMBA solution.

99. A process as set forth in claim 95 wherein said plug flow reactor is operated at a Reynolds number greater than about 3000.

100. A process as set forth in claim 95 wherein said plug flow reactor is operated at a Reynolds number greater than about 5000.

101. A process as set forth in claim 99 wherein said reactor comprises a pipeline reactor.

102. A process for the preparation of 2-hydroxy-4-methylthiobutanoic acid or a salt thereof comprising:

contacting 2-hydroxy-4-methylthiobutanenitrile with mineral acid in a nitrile hydrolysis reactor to produce an intermediate hydrolyzate comprising 2-hydroxy-4-methylthiobutanamide;

mixing said intermediate hydrolyzate with water to produce a finishing reaction solution; and passing said finishing reaction solution through a plug flow reactor for hydrolysis of 2-hydroxy-4-methylthiobutanoic, thereby producing an aqueous hydrolyzate product solution comprising 2-hydroxy-4-methylthiobutanoic acid.

103. The process as set forth in claim 102 wherein 2-hydroxy-4-methylthiobutanoic acid recovered by extracting said finishd aqueous hydrolyzate product with an organic solvent to form a 2-hydroxy-4-methylthiobutanoic acid-containing organic phase and an aqueous phase, and sujecting said 2-hydroxy-4-methylthiobutanoic acid-containing organic phase to evaporation to provide concentrated 2-hydroxy-4-methylthiobutanoic acid containing less than about 4 wt. % water and at least about 96 wt. % 2-hydroxy-4-methylthiobutanoic acid.

104. The process as set forth in claim 102 wherein 2-hydroxy-4-methylthiobutanoic acid is recovered by neutralizing said finished aqueous hydrolyzate product and extracting with a solvent to form an organic phase containing 2-hydroxy-4-methylthiobutanoic acid and an aqueous phase, treating said organic phase with aqueous ammonia to form a second aqueous phase containing an ammonium salt of 2-hydroxy-4-methylthiobutanoic acid and a second organic phase, and recovering the ammonium salt of 2-hydroxy-4-methylthiobutanoic acid from said second aqueous phase.

105. The process as set forth in claim 102 wherein 2-hydroxy-4-methylthiobutanoic acid is recovered by subjecting said finished aqueous hydrolyzate product to evaporation to obtain an HMBA-containig salt residue, treating said residue with an organic solvent to form a suspension, separating solids from said suspension to form an HMBA-containing solution, removing said organic solvent from said HMBA-containing solution to obtain an HMBA residue, and adding water to said HMBA residue to form an HMBA solution.

* * * * *